United States Patent
Mazur et al.

(10) Patent No.: US 6,613,874 B1
(45) Date of Patent: Sep. 2, 2003

(54) MELANOCORTIN RECEPTOR LIGANDS

(75) Inventors: Adam Wieslaw Mazur, Cincinnati, OH (US); Feng Wang, Cincinnati, OH (US); Russell James Sheldon, Fairfield, OH (US); Frank Hallock Ebetino, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/537,789

(22) Filed: Mar. 29, 2000

Related U.S. Application Data

(60) Provisional application No. 60/126,673, filed on Mar. 29, 1999.

(51) Int. Cl.[7] .............................................. C07K 7/50
(52) U.S. Cl. ...................... 530/317; 530/329; 530/330; 514/11; 514/16
(58) Field of Search .................... 514/16, 11; 530/330, 530/317, 329

(56) References Cited

U.S. PATENT DOCUMENTS

| | | | |
|---|---|---|---|
| 5,462,927 A | 10/1995 | Moreau et al. ................ | 514/17 |
| 5,569,741 A | 10/1996 | Coy et al. .................... | 530/311 |
| 5,770,380 A | 6/1998 | Hamilton et al. ............. | 435/7.1 |
| 6,054,556 A * | 4/2000 | Huby et al. .................. | 530/312 |

FOREIGN PATENT DOCUMENTS

| | | |
|---|---|---|
| EP | 0 427 458 | 11/1990 |
| EP | 0 499 266 | 2/1992 |
| EP | 0 528 312 | 8/1992 |
| EP | 0 547 317 | 10/1992 |
| EP | 0 552 417 | 10/1992 |
| EP | 0 632 052 | 6/1994 |
| EP | 0 292 291 | 8/1994 |
| EP | 0 309 297 | 11/1994 |
| EP | 0 714 909 | 5/1996 |
| EP | 0 815 870 | 1/1998 |
| EP | 0 967 222 | 12/1999 |
| WO | WO 94/02163 | 7/1993 |
| WO | WO 96/17617 | 12/1995 |
| WO | WO 96/34012 | 4/1996 |
| WO | WO 97/47317 | 6/1997 |
| WO | WO 97/08203 | 8/1997 |
| WO | WO 98/22128 | 11/1997 |
| WO | WO 98/27113 | 12/1997 |
| WO | WO 98/37097 | 2/1998 |
| WO | WO 00/35952 | 12/1999 |

OTHER PUBLICATIONS

Torsello, Antonio (Endocrinology 143 (5) 1968, 2002).*
McFadyen (Journal of Peptide Research (Mar. 2000) 55 (3) 255–61).*
Keith, (Molecular Pharmacology 53 (3) 377–84, 1998).*
Lunec, (Melanoma Research (May 1992) 2 (1) 5–12).*
Bray (Endocrine Reviews 20, 805–875, 1999).*
Kordik, Journal of Medicinal Chemistry, 42, 181, 1999.*
Xiao, Biochemistry 40, 2860, 2001.*
Chen, Anal. Biochem, 226, 349, 1995.*

* cited by examiner

*Primary Examiner*—Christopher S. F. Low
*Assistant Examiner*—David Lukton
(74) *Attorney, Agent, or Firm*—Richard S. Echler, Sr.; Mary Pat McMahon

(57) ABSTRACT

Disclosed are cyclic peptide analogs that are MC-4 and/or MC-3 receptor ligands, the analogs having a structure according to Formula (I):

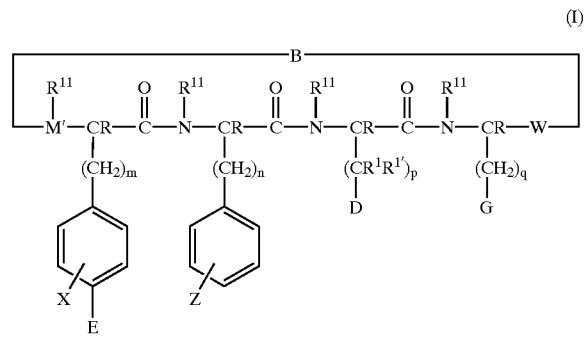

wherein B, X, E, Z, D, G, M', W, R, $R^1$, $R^{1'}$, $R^{11}$, m, n, p and q are as described in the specification. The peptide analogs are useful in treating diseases that are mediated by the MC-4 and/or the MC-3 receptor. As such, the invention is directed to methods of treating body weight disorders, such as obesity, anorexia, and cachexia. The invention also relates to the treatment of CNS depression, behavior-related disorders, memory-related disorders, cardiovascular function, inflammation, sepsis, septic shock, cardiogenic shock, hypovolemic shock, sexual dysfunction, erectile dysfunction, muscle atrophy, diseases associated with nerve growth and repair, and intrauterine fetal growth. Also disclosed are pharmaceutical compositions comprising the peptide analogs of Formula (I).

14 Claims, 6 Drawing Sheets

MELANOCORTIN RECEPTOR LIGANDS

CROSS REFERENCE TO RELATED APPLICATION

This application claims the benefit of U.S. Provisional Application No. 60/126,673, filed Mar. 29, 1999.

FIELD OF THE INVENTION

The present invention relates to new melanocortin receptor ligands. These ligands are cyclic peptide analogs that preferably exhibit selectivity for the MC-4 and/or the MC-3 receptors relative to the other melanocortin receptors (in particular the MC-1 receptor).

BACKGROUND OF THE INVENTION

Melanocortin peptides (melanocortins) are natural peptide hormones in animals and man that bind to and stimulate MC-receptors. Examples of melanocortins are α-MSH (melanocyte stimulating hormone), β-MSH, γ-MSH, ACTH (adrenocorticotropic hormone) and their peptide fragments. MSH is mainly known for its ability to regulate peripheral pigmentation (Eberle 1988), whereas ACTH is known to induce steroidoneogenesis (Simpson and Waterman, 1988). The melanocortin peptides also mediate a number of other physiological effects. They are reported to affect motivation, learning, memory, behavior, inflammation, body temperature, pain perception, blood pressure, heart rate, vascular tone, natriuresis, brain blood flow, nerve growth and repair, placental development, aldosterone synthesis and release, thyroxin release, spermatogenesis, ovarian weight, prolactin and FSH secretion, uterine bleeding in women, sebum and pheromone secretion, sexual activity, penile erection, blood glucose levels, intrauterine fetal growth, food motivated behavior, as well as other events related to parturition.

ACTH and the various MSH peptides share the tetrapeptide core His-Phe-Arg-Trp. All of the peptides are derived from the proteolytic processing of the pro-peptide pre-opiomelanocortin (POMC). In the past several years, five distinct melanocortin receptor subtypes have been identified. These MC receptors belong to the class of 7 transmembrane domain G-protein coupled receptors. The five MC receptors, termed MC-1, MC-2, MC-3, MC-4 and MC-5, all couple in a stimulatory fashion to cAMP. Of these, the MC-2 receptor is the ACTH receptor, whereas the others constitute subtypes of MSH receptors. The MC-1receptor is present on melanocytes and melanoma. The MC-2 receptor is present predominantly in the adrenal gland. The mRNA for the MC-3 receptor has been found in the brain, as well as in placental and gut tissues (Gantz et al. 1993a, Desamaud et al. 1994, Roselli Rehfuss et al. 1993). The MC-4 receptor has been found primarily in the brain (Gantz et al. 1993b; Mountjoy et al 1994). The MC-5 receptor is expressed in the brain, as well as in several peripheral tissues (Chhajlani et al 1993; Gantz et al 1994; Griffon et al 1994; Labbu et al. 1994; Barrett et al. 1994; Fathi et al.1995). More recent data from humans indicate that all of the cloned MC-receptors have a wider tissue distribution (Chhajlani, 1996) than originally thought.

As discussed above, the members of the melanocortin receptor family can be differentiated on the basis of their tissue distribution. Both the MC-4 and MC-3 receptors have been localized to the hypothalamus, a region of the brain believed to be involved in the modulation of feeding behavior. Compounds showing selectivity for the MC-4/MC-3 receptors have been shown to alter food intake following intracerebroventricular and peripheral injection in rodents. Specifically, agonists have been shown to reduce feeding, while antagonists have been shown to increase feeding. See, Fan, W. et al., "Role of Melanocortinergic Neurons in Feeding and the Agouti Obesity Syndrome", *Nature*, 385 (6612), pp. 165–8 (Jan. 9, 1997).

The role of the MC-4 receptor subtype has been more clearly defined in the control of eating and body weight regulation in mammals. See, e.g., Huszer, D. et al., "Targeted Disruption of the Melanocortin-4 Receptor Results in Obesity in Mice", *Cell*, pp. 131–141 (1997); Klebig, M. L. et al., "Ectopic Expression of the Agouti Gene in Transgenic Mice Causes Obesity, Features of Type II Diabetes, and Yellow Fur", *Proc. Natl Acad Sci.*, Vol. 92, pp. 4728–32 (1995); Karbon, W. et al., "Expression and Function of Argt, a Novel Gene Related to Agouti", Abstract from the Nineteenth Annual Winter Neuropeptide Conference (1998); Fan, W. et al., "Role of Melanocortinergic Neurons in Feeding and the Agouti Obesity Syndrome", *Nature*, Vol. 385, pp. 165–168 (1997); Seely, R. J., "Melanocortin Receptors in Leptin Effects", *Nature*, Vol. 390, p. 349 (1997); Comuzzie, A. G., "A Major Quantitative Trait Locus Determining Serum Leptin Levels and Fat Mass is Located on Human Chromosome 2", *Nat. Gen.*, Vol. 15, pp. 273–276 (1997); Chagnon, Y. C. et al., "Linkage and Association Studies Between the Melanocortin Receptors 4 and 5 Genes and Obesity-Related Phenotypes in the Quebec Family Study", *Mol. Med.*, Vol 3(10), pp. 663–673 (1997); Lee, F. and Huszar, D, "Screening Methods for Compounds Useful in the Regulation of Body Weight", World Patent Publication WO 97/47316 (1997); and Shutter, J. R. et al., "Hypothalamic Expression of ART, a Novel Gene Related to Agouti, is Up-Regulated in Obese and Diabetic Mutant Mice", *Gen. & Dev.* Vol. 11, pp. 593–602 (1997). Stimulation of the MC-4 receptor by its endogenous ligand, CCMSH, produces a satiety signal and may be the downstream mediator of the leptin satiety signal. It is believed that by providing potent MC-4 receptor agonists, appetite may be suppressed and weight loss benefits may be achieved.

Applicants have discovered a class of compounds that surprisingly have high affinity for the MC-4 and/or the MC-3 receptor subtypes, and that are typically selective for these MC receptors relative to the other melanocortin receptor subtypes, particularly the MC-1 subtype. It is therefore an object of this invention to provide chemical compounds that activate or antagonize the MC-4 and/or the MC-3 receptor subtypes. It is a further object of the invention to provide means for administration of said compounds to animals or man. Still other objects of the invention will be evident from the following disclosure of the invention.

DISCLOSURE OF THE INVENTION

Applicants have discovered certain structural requirements for a class of cyclic peptide analogs that are ligands for receptors of the MC-4 and/or the MC-3 subtype. The structural requirements constitute an optimal ring size of the peptide analog cycle at the proper location in the analog, as is described below. Thus, the present invention relates to a cyclic peptide analog having a structure according to Formula (I):

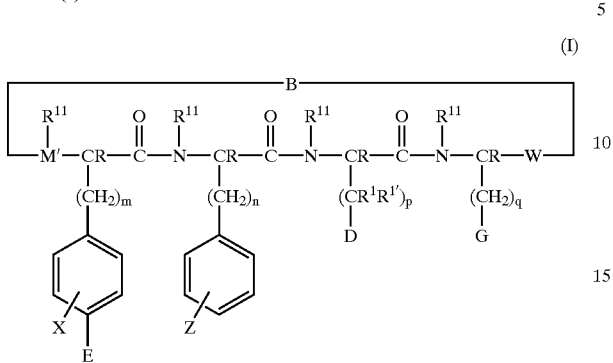

wherein
(A) each of m, n, and q is independently selected from 0 to about 4 and p is from 0 to about 5;
(B) X, which represents the four substituents on the phenyl ring other than E and $(CH_2)_m$, is independently selected from hydrogen; halo; $OR^8$; $-SR^8$; $-NR^8R^{8'}$; $-N(R^8)SO_2R^{8''}$; $-SO_2R^{8''}$; $-SO_2-NR^8R^{8'}$; alkyl; alkene; alkyne; cyano; nitro; $CF_3$; aryl; heteroaryl; cycloalkyl; heterocycloalkyl; and $-(CH_2)_r-PO_2HR^{14}$ where r is 0 to about 10 and $R^{14}$ is selected from $-OH$, hydrogen and alkyl; where each $R^8$ and $R^{8'}$ is independently selected from hydrogen, alkyl, acyl, heteroalkyl, aryl, heteroaryl, cycloalkyl, and heterocycloalkyl and $R^{8''}$ is selected from hydrogen, alkyl, heteroalkyl, aryl, heteroaryl, cycloalkyl, and heterocycloalkyl; or two X moieties can together form a fused ring with the depicted phenyl ring;
(C) E is selected from hydrogen; halo; $-OR^{13}$; $-SR^{13}$; $-NR^{13}R^{13'}$; $-N(R^{13})SO_2R^{13''}$; $-SO_2R^{13''}$; $-SO_2-NR^{13}R^{13'}$; $-(CH_2)_r-PO_2HR^{15}$ where r is 0 to about 10 and $R^5$ is selected from $-OH$, hydrogen and alkyl; alkyl; alkene; alkyne; cyano; nitro; $CF_3$; aryl; heteroaryl; cycloalkyl; and heterocycloalkyl; provided that when each X is hydrogen, E is not hydrogen; where each $R^{13}$ and $R^{13'}$ is independently selected from hydrogen, alkyl, acyl, heteroalkyl, aryl, heteroaryl, cycloalkyl, and heterocycloalkyl and $R^{13''}$ is selected from hydrogen, alkyl, heteroalkyl, aryl, heteroaryl, cycloalkyl, and heterocycloalkyl;
(D) Z is one or more substituents independently selected from hydrogen, hydroxy, halo, thiol, $-OR^9$, $-SR^9$, $-NR^9R^{9'}$, alkyl, acyl, alkene, alkyne, cyano, nitro, aryl, heteroaryl, cycloalkyl, and heterocycloalkyl; where each $R^9$ and $R^{9'}$ is independently selected from hydrogen, alkyl, acyl, heteroalkyl, aryl, heteroaryl, cycloalkyl, and heterocycloalkyl; or some Z moieties can form a fused ring with the depicted phenyl ring;
(E) D is selected from $-N(R^2)C(=NR^3)NR^4R^5$, an optionally substituted imidazole ring, and $-NR^4R^5$, wherein
(1) $R^2$ and $R^3$ are independently selected from hydrogen, alkyl, and alkyne; or $R^2$ and $r^3$, together with the atoms to which they are bondded, joint to from a heterocycloalkyl or a heteroaryl; or $R^2$ and $R^4$, together with the atoms to which they are bonded, joint to form a heteropcycloalkyl or a heteroaryl; or $R^3$ and $R^4$, together with the atoms to which they are bonded, joint to form a heterocycloalkyl or a heteroaryl; and
(2) $R^4$ and $R^5$ are independently selected from hydrogen, alkyl, alkene, and alkyne; or $R^4$ and $R^5$, together with the atoms to which they are bonded, join to form a heterocycloalkyl or a heteroaryl;
(F) each $R^1$ and $R^{1'}$ is independently selected from hydrogen, alkyl, aryl and heteroaryl; or two $R^1$ moieties, together with the carbon atoms to which they are bonded, join to form a cycloalkyl or aryl ring; or an $R^1$ and $R^2$ (if present), together with the atoms to which they are bonded, join to form a heterocycloalkyl or a heteroaryl; or an $R^1$ and $R^3$ (if present), together with the atoms to which they are bonded, join to form a heterocycloalkyl or a heteroaryl; or an $R^1$ and $R^4$ (if present), together with the atoms to which they are bonded, join to form a heterocycloalkyl or a heteroaryl;
(G) G is selected from an optionally substituted bicyclic aryl ring and an optionally substituted bicyclic heteroaryl ring;
(H) each $R^{11}$ is independently selected from hydrogen, alkyl, alkene, alkyne, aryl, heteroaryl, and cycloalkyl; and each R is independently selected from hydrogen, alkyl, alkene, alkyne, aryl, heteroaryl, and cycloalkyl; or an $R^{11}$ moiety can join with an adjacent R moiety to form a ring;
(I) W is selected from covalent bond, $-CH_2-$ and $-C(=O)-$;
(J) M' is selected from covalent bond, $-N-$ and $-CH-$; and
(K) B is an optionally substituted bridge moiety that links M' and W to form a ring and comprises either a covalent bond or an ionic bond, wherein when the bridge moiety comprises an ionic bond it is unsubstituted or is substituted with not more than 3 amino acid residues;
provided that when the compound comprises less than 25 ring atoms, then the phenyl ring substituted with Z is of the D-configuration ("D-Phe" or "f") and further provided that when B comprises two or more Cys residues that form one or more disulfide bonds, said disulfide bond(s) is not necessary for the existence of the cyclic peptide analog of Formula (I).

The invention also relates to pharmaceutical compositions comprising the above compounds, and to methods of treating disorders mediated by the MC-3 or MC-4 receptor by administering these compounds.

DESCRIPTION OF THE FIGURES

FIG. 1 shows the % cAMP activity at various concentrations for Ac-a[DYfRWGK]-NH$_2$ thereby demonstrating the selectivity of this analog for MC-4R over the MC-3R and MC-1R.

FIG. 2 shows the % cAMP activity at various concentrations for Ac-a[EYfRWG(Orn)]—NH$_2$ thereby demonstrating the selectivity of this analog for MC-4R over the MC-3R and MC-1R.

FIG. 3 shows the % cAMP activity at various concentrations for Ac-a[DyfRWGK]-NH$_2$ thereby demonstrating the selectivity of this analog for MC-4R over the MC-3R and MC-1R.

FIG. 4 shows the % cAMP activity at various concentrations for Ac-a[EYfRWGKl-NH$_2$ thereby demonstrating the selectivity of this analog for MC-4R over the MC-3R and MC-1R.

FIG. 5 shows the % cAMP activity at various concentrations for Ac-aDYfRWGK-NH$_2$ thereby demonstrating the selectivity of this analog for MC-4R over the MC-3R and MC-1R.

FIG. 6 shows the % cAMP activity at various concentrations for Ac-a[DYtRWG(Orn)]-NH$_2$ thereby demonstrating the selectivity of this analog for MC-4R over MC-1R.

FIG. 7 shows the % cAMP activity at various concentrations for Ac-aDYfRWG(Orn)-NH$_2$ thereby demonstrating the selectivity of this analog for MC-4R over MC-1R.

FIG. 8 shows the % cAMP activity at various concentrations for Ac-aEYfRWG(Orn)-NH$_2$ thereby demonstrating the selectivity of this analog for MC-4R over MC-1R.

FIG. 9 shows the % cAMP activity at various concentrations for Ac-aDYflZWK-NH$_2$ thereby demonstrating the selectivity of this analog for MC-4R over MC-1R.

FIG. 10 shows the % cAMP activity at various concentrations for Ac-DYtRWGK-NH$_2$ thereby demonstrating the selectivity of this analog for MC-4R over the MC-3R and MC-1R.

FIG. 11 shows the % cAMP activity at various concentrations for Ac-SYSNIeEHfRWGKPV-NH$_2$, a non-selective agonist, thereby demonstrating how the compounds of FIGS. 1–10 demonstrate selectivity for MC-4R over the MC-3R and MC-1R.

FIG. 12 shows the % cAMP activity at various concentrations for Ac-NIeDHfRWGK-NH$_2$, a non-selective agonist, thereby demonstrating how the compounds of FIGS. 1–10 demonstrate selectivity for MC-4R, over the MC-3R and MC-1R.

DETAILED DESCRIPTION OF THE INVENTION

1. Definitions

Figure 1:
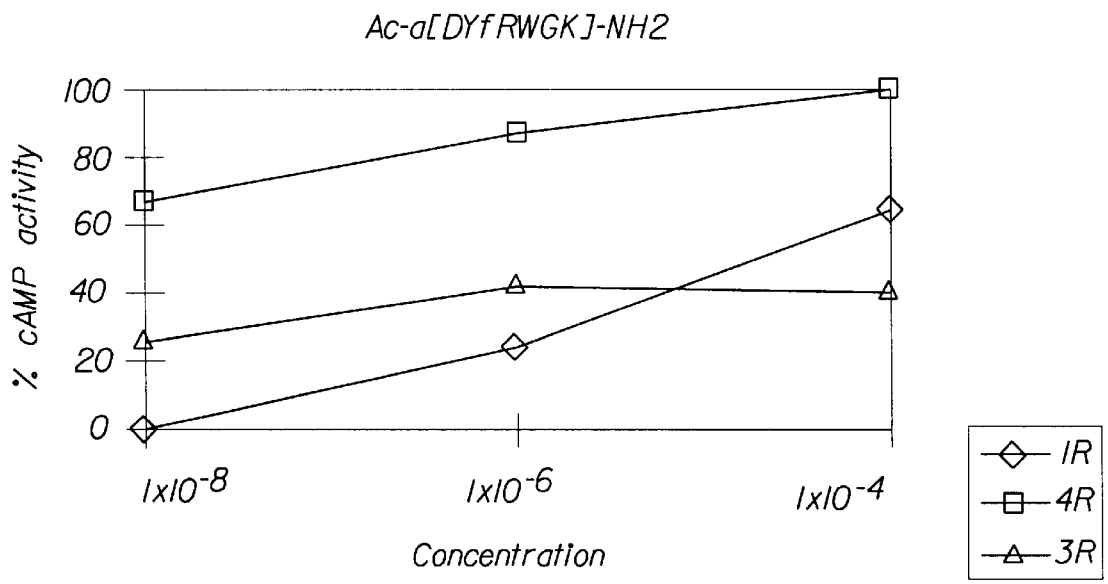
FIGS. 1–12 describe the relative selectivity of 10 analogs of the present invention (FIGS. 1–10) and two known non-selective agonists (FIGS. 11 and 12). The relative affinities of the 10 analogs and 2 standards for each melanocortin receptor, are expressed as a per cent of c-AMP production relative to a standard c-AMP producing non-selective agonist, norleucine-4-D-phenylalanine-7-melanociyte stimulating hormone (NDP-MSH). The NDP-MSH standard was evaluated for the level of c-AMP release at each receptor and the values for the test samples were expressed as a % of the maximal amount produced by NDP-MSH. 1R, 3R, and 4R correspond respectively to the MC-1, MC-3, and MC-4 receptors. The % c-AMP produced by each compound was measured at concentrations from $1 \times 10{-8}$ to $1 \times 10^{-4}$ molar.
Figure 2:
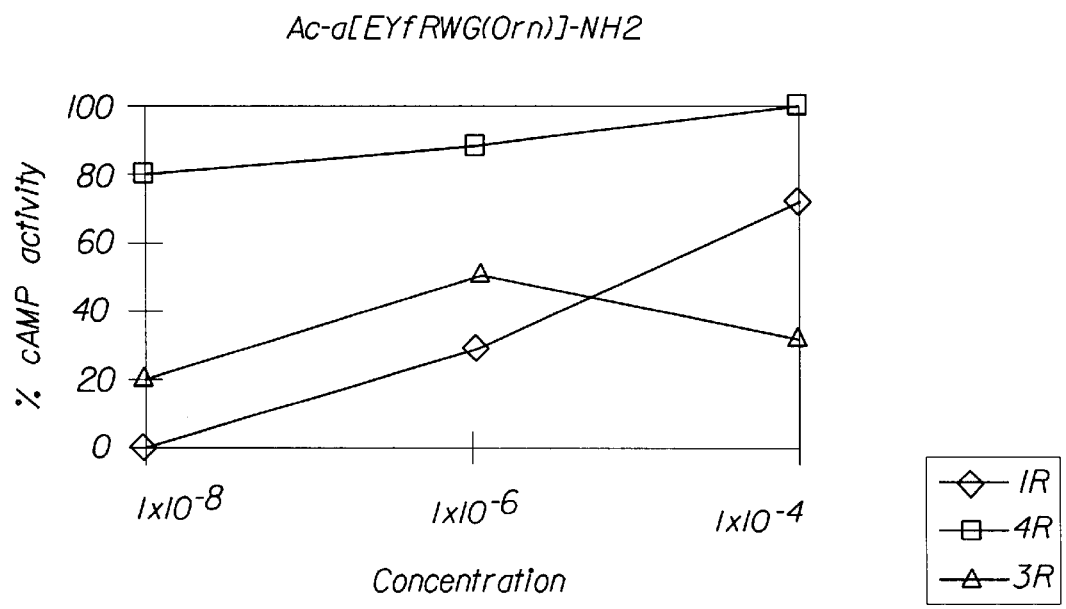
Figure 3:
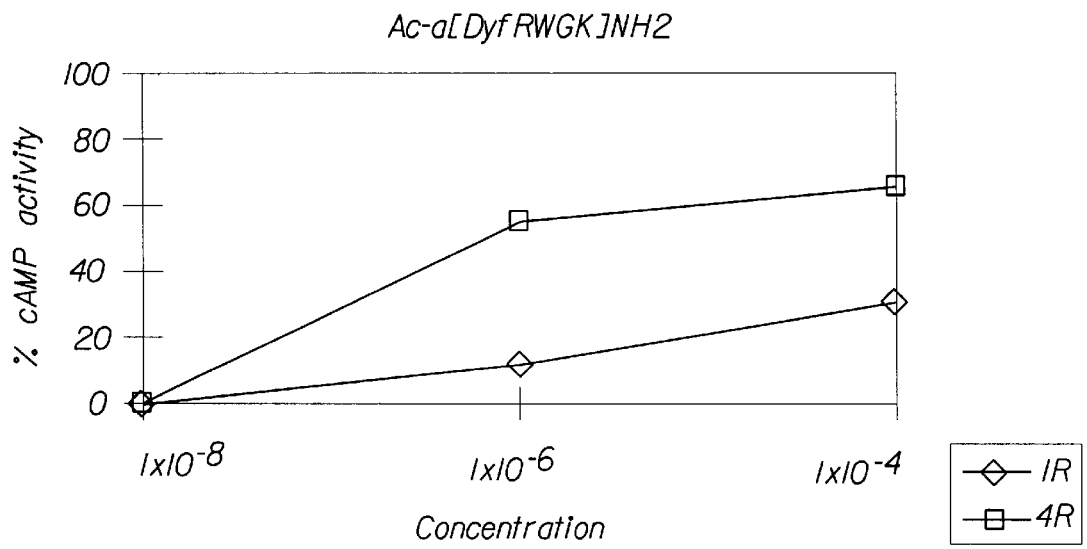
Figure 4:
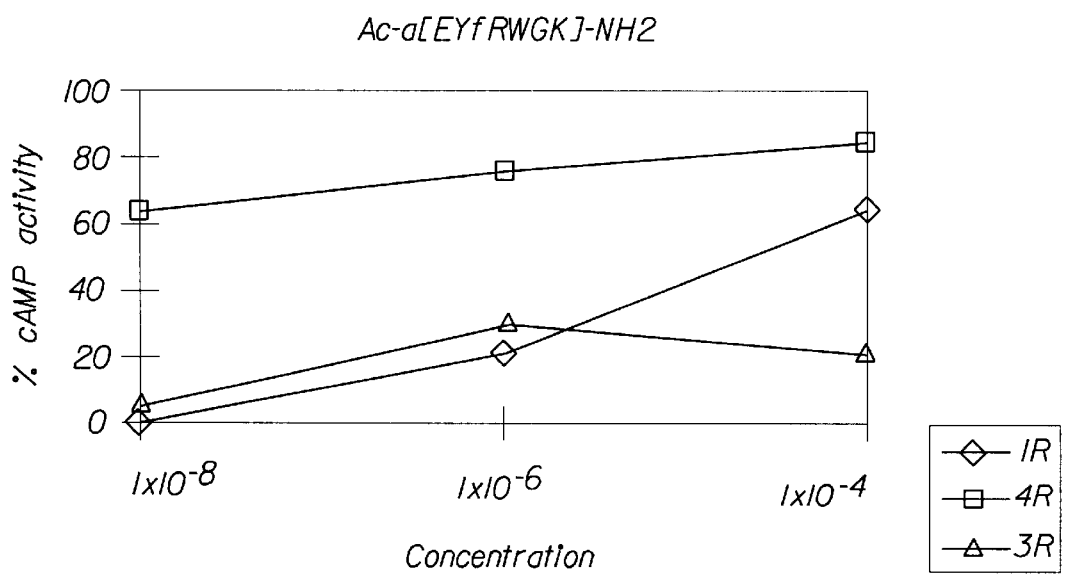
Figure 5:
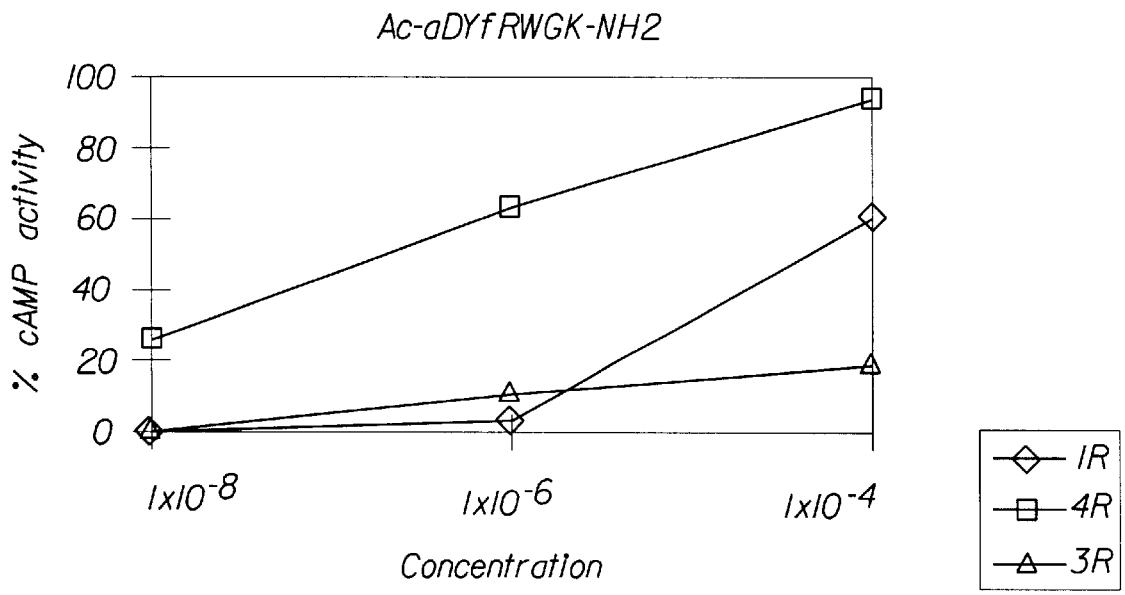
Figure 6:
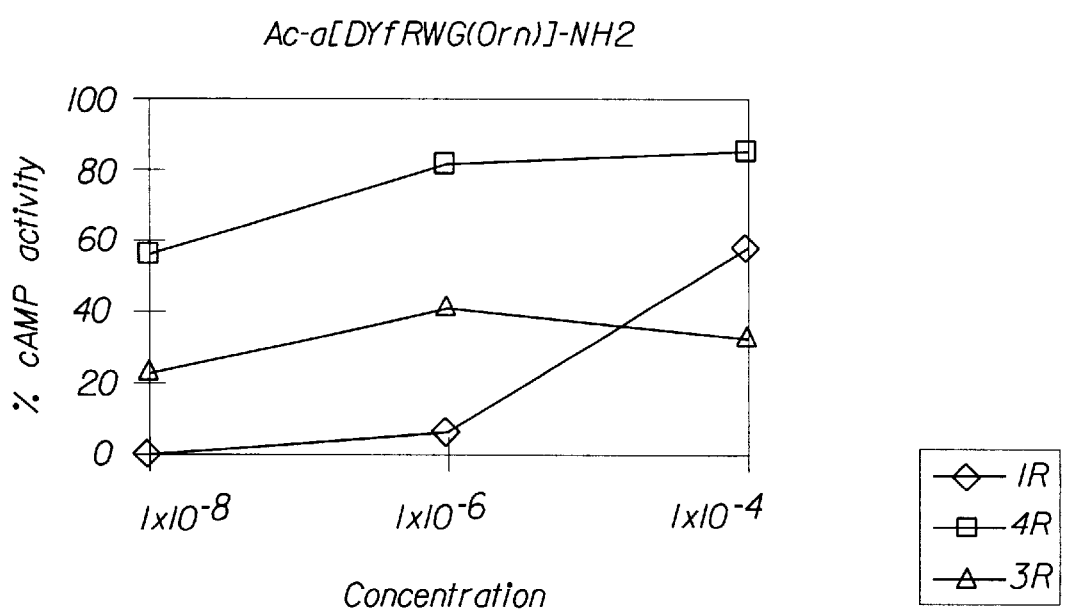
Figure 7:
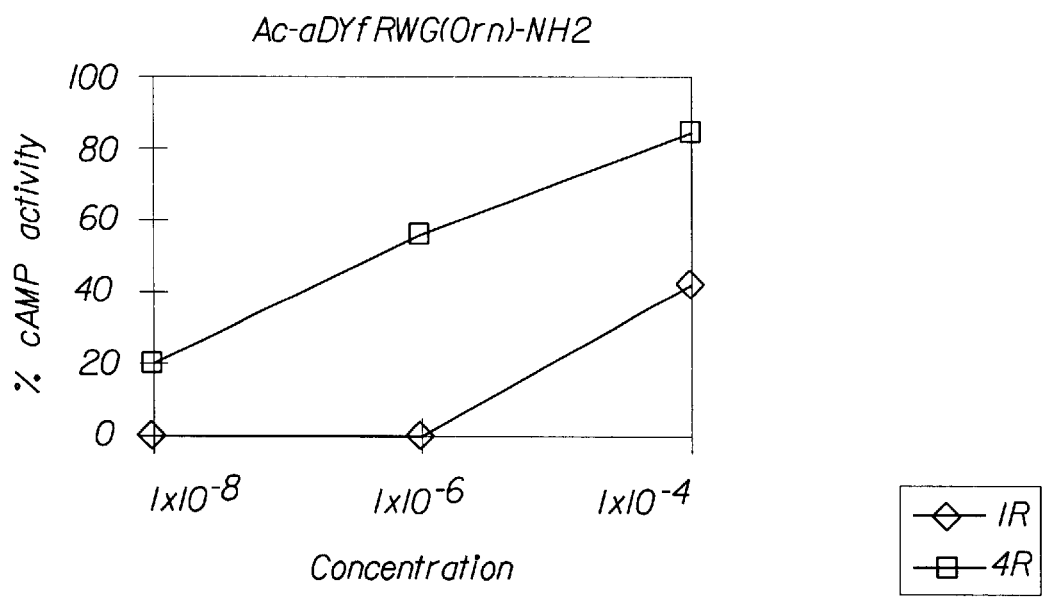
Figure 8:
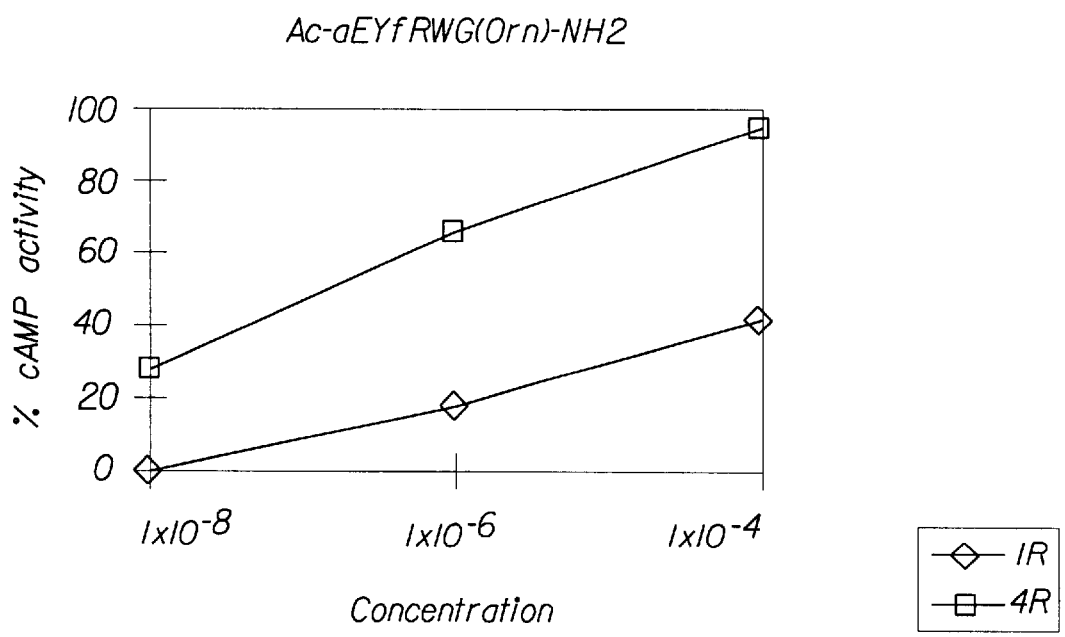
Figure 9:
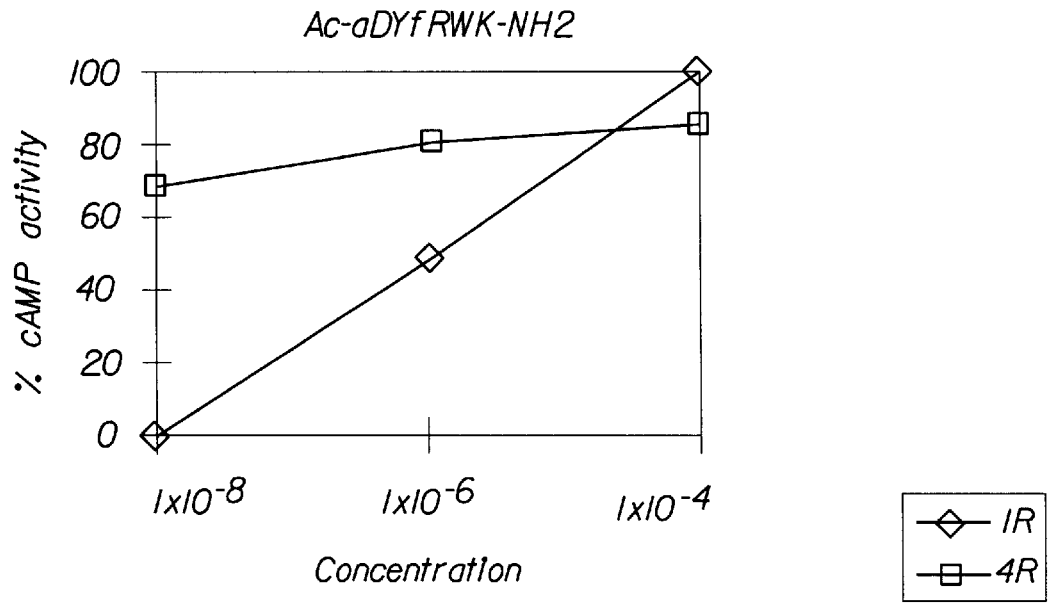
Figure 10:
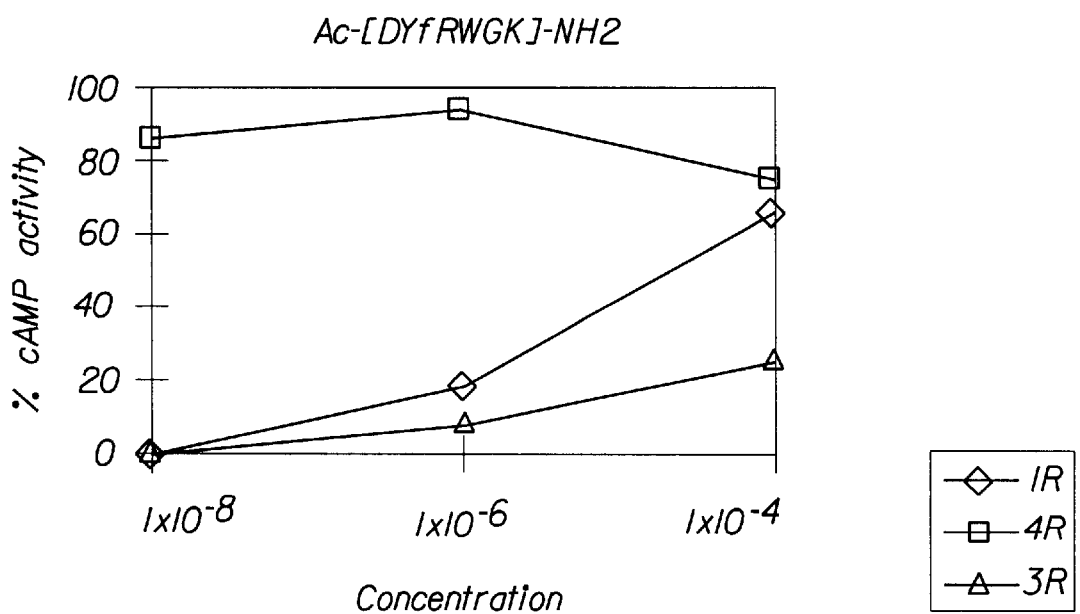
Figure 11:
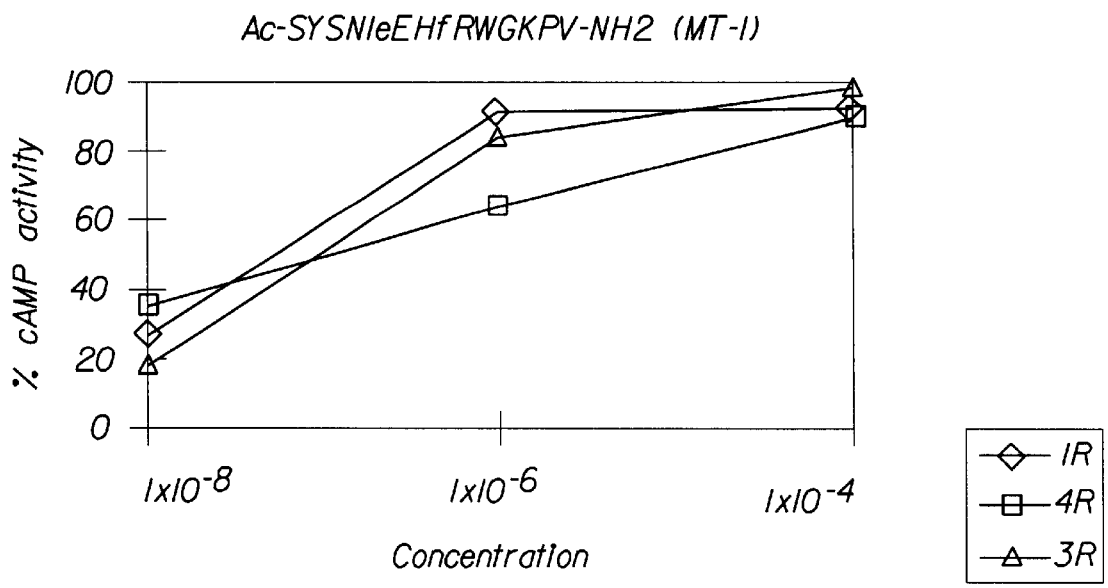
Figure 12:
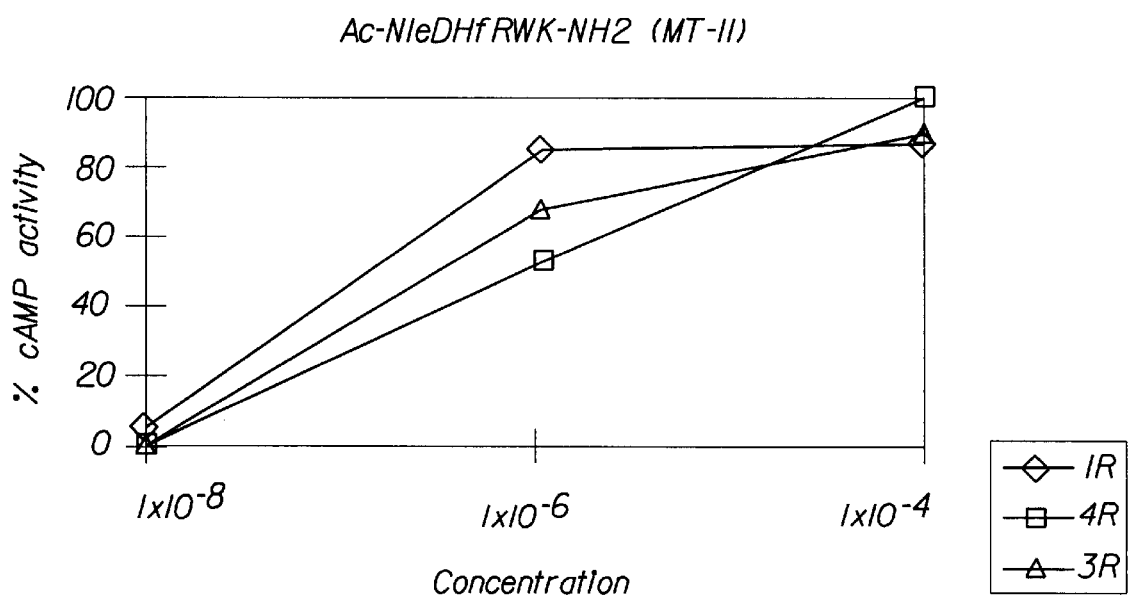

"Amino acid" refers to alanine (Ala; A), arginine (Arg; R), asparagine (Asn; N), aspartic acid (Asp; D), cysteine (Cys; C), glutamic acid (Glu; Q), glutamine (Gln; E), glycine (Gly; G), histidine (His; H), isolcucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). The common 3-letter and 1-letter abbreviations are indicated parenthetically. Modified amino acids also useful herein are the following (the 3-letter abbreviation for each moiety is noted parenthetically): p-Benzoyl-phenylalanine (Bpa); β-(2-Naphthyl)-alanine (Nal); β-Cyclohexylalanine (Cha), 3,4-Dichlorophenylalanine (3,4-Dcp); 4-Fluorophenylalanine (4-Fpa); 4-Nitrophenylalanine (4-Npa); 2-Thienylalanine (Tha); 1,2,3,4-Tetrahydroisoquinoline-3-carboxylic acid (Tic); 3-Benzothienylalanine (3-Bal); 4-Cyanophenylalanine (4-Ypa); 4-Iodophenylalanine (4-lpa); 4-Bromophenylalanine (4-Rpa); 4,4'-Biphenylalanine (Bip); Pentafluorophenylalanine (Pfp); and β,β-Diphenylalanine (Dip). With respect to moieties depicted on Formula (I) and Formula (A), moieties referred to using a single letter designation are as defined and do not refer to the single letter amino acids corresponding to those letters.

The letter "D" preceding the above three-letter abbreviations, e.g. as in "D-Nal" or "D-Phe", denotes the D-form of the amino acid. The letter "L" preceding an amino acid three-letter abbreviation denotes the natural L-form of the amino acid. For purposes of this disclosure, unless otherwise indicated, absence of a "D" or "L" designation indicates that the abbreviation refers to both the D- and L-forms. Where the common single-letter abbreviation is used, capitalization refers to the L-form and small letter designation refers to the D-form, unless otherwise indicated.

"Ac" refers to acetyl (i.e., $CH_3C(=O)—$).

"Alkoxy" is an oxygen radical having a hydrocarbon chain substituent, where the hydrocarbon chain is an alkyl or alkene (i.e., —O-alkyl or —O-alkene). Preferred alkoxy groups include (for example) methoxy (MeO), ethoxy, propoxy and allyloxy.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl (Me), ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne. "Alkylthio" is a sulfur radical having a hydrocarbon chain substituent, where the hydrocarbon chain is an alkyl or alkene (i.e., —S-alkyl or —S-alkene). Preferred alkylthio groups include (for example) methylthio (MeS) and ethylthio.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from about 8 to about 17 carbon atoms, preferably about 9 to about 12 carbon atoms in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, naphthyloxy, methoxyphenoxy, and methylenedioxyphenoxy.

As used herein, "basic amino acids" refers to His, Lys, and Arg.

"Bc" refers to butyryl (i.e., $CH_3CH_2CH_2C(=O)$—).

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms in the ring. Bicyclic cycloalkyl rings contain from 7 to 17 carbon atoms, preferably from about 7 to about 12 carbon atoms in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof Preferred cycloalkyl rings include cyclopropyl, cyclopentyl, and cyclohexyl.

"Fused" refers to cyclic moieties having at least two common ring atoms, the preferred maximum number of fused cycles being three.

"Halo" is fluoro (F), chloro (Cl), bromo (Br) or iodo (I).

"Heteroatom" is a nitrogen, sulfur, or oxygen atom, to which one or more moieties may be connected according to heteroatom valence; in the case of nitrogen, one oxygen atom may be optionally connected to it by a donor or acceptor bond, such as forming an N-oxide. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to about 15 member atoms (carbon and heteroatoms) in the chain, preferably 2 to about 10, more preferably 2 to about 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more double bonds (also referred to herein as "heteroalkenyl") and/or one or more triple bonds (also referred to herein as "heteroalkynyl"). Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heterocycloalkyl" is a saturated or unsaturated, non-aromatic ring containing carbon and from 1 to about 4 (preferably 1 to 3) heteroatoms in the ring, wherein no two heteroatoms are adjacent in the ring and no carbon in the ring that has a heteroatom attached to it also has a hydroxyl, amino, or thiol radical attached to it. Heterocycloalkyl rings are monocyclic, or are fused, bridged, or spiro bicyclic ring systems. Monocyclic heterocycloalkyl rings contain from about 4 to about 9 member atoms (carbon and heteroatoms), preferably from 5 to 7 member atoms in the ring. Bicyclic heterocycloalkyl rings contain from about 7 to about 17 atoms, preferably from 7 to 12 atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, phenoxy or any combination thereof. Preferred substituents on heterocycloalkyl include halo and haloalkyl.

"Heteroaryl" is an aromatic ring containing carbon and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms in the ring. Bicyclic heteroaryl rings contain from about 8 to about 17 member atoms, preferably about 8 to about 12 member atoms in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, aryloxy, heteroaryloxy, or any combination thereof. Preferred heteroaryl rings include thienyl, thiazolo, imidazyl, purinyl, pyrimidyl, pyridyl, and furanyl.

As used herein, "MC-4 agonist" and "MC-3 agonist" refers to a compound with affinity for the MC-4 receptor or MC-3 receptor, respectively, that results in measurable biological activity in cells, tissues, or organisms which contain the MC-4 or MC-3 receptor. Assays which demonstrate MC-4/MC-3 agonistic activity of compounds are well known in the art. One particularly useful assay is the BioTrak TM cAMP direct enzymeimmunoassay (EIA) system from Amersham Pharmacia Biotech, which quantitates the cAMP response of cells to MC ligands. This system allows the simple quantitation of total cellular cAMP measurement in cells exposed to selective ligands. Briefly summarized: HEK cells stably transfected with the MC-1, MC-3 or MC-4 receptors are plated into 96 well microtiter plates and grown overnight. Cells are dosed with the appropriate MC ligand for 1 hour and then lysed. A fraction of the lysed cell extract is transferred to the assay plate. The ELISA assay is performed according to kit instructions. Each plate contains a series of cAMP standards for calculating a standard curve, as well as a full MC agonist as a positive control for each MC receptor. cAMP activity is calculated as a % of the maximum cAMP activity of the full MC agonist control.

As used herein, "MC-4 antagonist" and "MC-3 antagonist" refer to compounds with affinity for the MC-4 receptor or MC-3 receptor, respectively, and blocks stimulation by a known MC agonist. Assays which demonstrate MC-4/MC-3 antagonistic activity of compounds are well known in the art.

As used herein, "MC-3 receptor" and "MC-4 receptor" mean the known MC-3 and MC-4 receptors, their splice variants, and undescribed receptors. MC-3 receptors are described by Gantz et al., supra (human MC-3); Desarnaud et al., supra (mouse MC-3) and L. Reyfuss et al., "Identification of a Receptor for Gamma Melanotropin and Other Proopiomelanocortin Peptides in the Hypothalamus and Limbic System», *Proc. Natl. Acad. Sci. USA*, vol. 90, pp. 8856–8860 (1993) (rat MC-3). MC-4 receptors are described by Gantz et al., supra (human MC-4), J. D. Alvaro et al., "Morphine Down-Regulates Melanocortin-4 Receptor Expression in Brain Regions that Mediate Opiate Addiction", *Mol-Pharmacol. Sep*, vol. 50(3), pp. 583–91 (1996) (rat MC-4) and Takeuchi, S. and Takahashi, S., "Melanocortin Receptor Genes in the Chicken—Tissue Distributions", *Gen-Comp-Endocrinol.*, vol. 112(2), pp 220–31 (Nov. 1998) (chicken MC-4).

As used herein, "measurable" means the biologic effect is both reproducible and significantly different from the baseline variability of the assay.

A "pharmaceutically-acceptable salt" is a cationic salt formed at any acidic (carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there is none. For example, a chiral tartrate salt may be prepared from the compounds of the invention, and this definition includes such chiral salts.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

As used herein, "selective" means having an activation preference for a specific receptor over other receptors which can be quantified based upon whole cell, tissue, or organism assays which demonstrate receptor activity, such as the cAMP enzyme immunoassay (EIA) system discussed above. A compound's selectivity is determined from a comparison of its $EC_{50}$ values at the relevant receptors being referenced. As used herein, use of the term "selective over the other MC receptors" means selective with respect to all of the MC-1, MC-2 and MC-5 receptors. For example, a compound having an $EC_{50}$ of 8 nM at the MC-4 receptor and an $EC_{50}$ of $\geq 80$ nM at the MC-1, MC-2 and MC-5 receptors has a selectivity ratio for the MC-4 receptor over the other MC receptors of at least 1:10. Additionally, it will be recognized that selectivity may also refer to one of the MC-1, MC-2 or MC-5 receptors individually. For example, a compound having an $EC_{50}$ of 8 nM at the MC-4 receptor and an $EC_{50}$ of 80 nM at the MC-1 receptor has a selectivity ratio for the MC-4 receptor over the MC-1 receptor of 1:10. Such a compound is selective over the MC-1 receptor, regardless of its $EC_{50}$ value for MC-2 or MC-5. Selectivity is described in more detail below and may be determined by using, for example, the software Prism v 2.0 which is available from GraphPad, Inc.

"Spirocycle" is an alkyl or heteroalkyl diradical substituent of an alkyl or heteroalkyl, wherein said diradical substituent is attached geminally and wherein said diradical substituent forms a ring, said ring containing about 4 to about 8 member atoms (carbon or heteroatoms), preferably 5 or 6 member atoms.

"Substituted" refers to one or several hydrogens being substituted, independently, by alkyl, haloginated alkyl, alkenyl, halogenated alkenyl, alkynyl, halogenated alkynyl, cycloalkyl, halogenated cycloalkyl, cycloheteroalkyl, halogenated cycloheteroalkyl, cycloalkenyl, halogenated cycloalkenyl, cycloheteroalkenyl, halogenated cycloheteroalkenyl, aryl, halogenated aryl, heteroaryl, halogenated heteroaryl and/or functional group. Moreover, if a "substituted" structure is a cyclic structure fused with other cyclic structure(s) these latter cyclic structure(s) may also be substituted.

A "solvate" is a complex formed by the combination of a solute (e.g., a cyclic MC-4/MC-3 receptor ligand of the present invention) and a solvent (e.g., water). See J. Flonig et al., *The Van Nostrand Chemist's Dictionary*, p. 650 (1953). Pharmaceutically-acceptable solvents used according to this invention include those that do not interfere with the biological activity of the compound (e.g., water, ethanol, acetic acid, N,N-dimethylformamide and others known or readily determined by the skilled artisan).

II. The Compounds

The compounds of the present invention are MC-4 and/or MC-3 receptor ligands having a structure according to Formula (I):

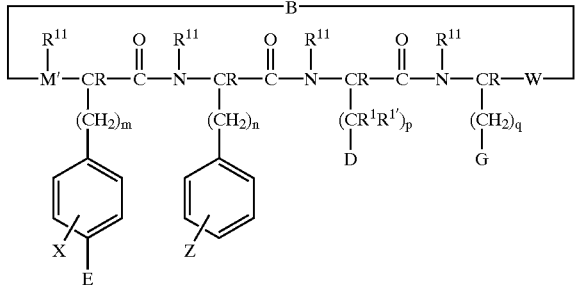

(I)

wherein B, X, E, Z, D, G, R, $R^1$, $R^{1'}$, $R^{11}$, m, n, p, and q are as described in the Disclosure of the Invention section above.

With reference to Formula (I), it is seen that the compounds comprise an important backbone based on the natural amino acid sequence Tyr (or substituted Phe)-Phe-J-M (per the description above, when the first amino acid is Phe it should be substituted and is preferably Tyr), where J is an amino acid whose side chain is a nitrogen containing group (e.g., Arg, His or Lys) or a derivative thereof, and M is a bicyclic aromatic moiety (e.g., Trp or naphthylalanine, or a derivative thereof). Preferred are those compounds wherein J is Arg or a derivative of Arg and M is Trp or a derivative of Trp. It is noted, as is depicted in Formula (I), that substitution of the natural amino acids is possible without losing the MC-3/MC-4 ligand properties. In this regard, while reference is made herein to the Phe(Tyr)-Phe-J-M sequence, it is understood that substitution is allowed per the description of Formula (I).

Applicants have found that to obtain optimum agonistic or antagonistic activity, the ring moiety of the compound will preferably comprise from 25 to 27 ring atoms. That is, the ring comprising the depicted residues and the bridging moiety, B, preferably contains from 25 to 27 ring atoms. It will be recognized that additional amino acids or other chemical entities may be included as substituents on the cyclic structure depicted in Formula (I) without negatively impacting interaction with MC-3/MC-4 receptor.

That the compounds of Formula (I) have affinity for the MC-4 and/or the MC-3 receptor is surprising, given that the linear compound BIM-22015 exhibits essentially no affinity for any of the melanocortin receptors, including MC-3 and MC-4, while differing from endogenous α-MSH in the 6-9 region by only the substitution of Tyr for His at position 6 (using natural α-MSH numbering). See, e.g., Schioth, H. B. et al., "Selectivity of [Phe-17], [Ala6] and [D-Ala4, Gln5, Tyr6] Substituted ACTH (4–10) Analogues for the Melanocortin Receptors", Peptides, vol. 18(5), pp. 761–3 (1997).

```
                              BIM-22015
      -Tyr-Phe-Arg-Trp-
        6    7    8   9
```

```
                              alpha-MSH
      -His-Phe-Arg-Trp-
        6    7    8   9
```

One would have also predicted that Applicants' compounds would lack affinity for these receptors given the common -Tyr-Phe-Arg-Trp- domain the preferred compounds share with BIM-22015. That is, the logical conclusion is that the His at position 6 is critical, or at a minimum that His at position 6 cannot be replaced with a substituted Phe or Tyr. Surprisingly, this is not the case, as Applicants compounds exhibit significant affinity for one or both of the MC-3 and MC-4 receptors. Without being bound by theory, Applicants believe the surprisingly high affinity of the present compounds is due to the shape of these residues induced by the cyclic nature of the molecules. That is, the cyclic aspect of the compounds provides rigidity which allows them to effectively interact with the relevant binding sites of the MC-4/MC-3 receptor. Moreover, it appears that the surprising ability to retain the preferred Tyr-like residue provides desired selectivity relative to the other MC receptors, particularly the MC-1 receptor.

With respect to B, this bridge can be in the form of covalent bond linkages or alternatively can include a salt bridge resulting from the formation of ionic bonds. The bridging moiety can be wholly peptidic in nature (i.e., containing amino acids only), non- peptidic (i.e., containing no amino acids) in nature, or it can include both peptidic and non- peptidic moieties introduced using well known chemistry. The bridge can comprise aliphatic residues, aromatic residues or heteroaromatic residues, or any combination thereof. The bridge preferably comprises at least 2 amino acids, such that the compounds of the present invention comprise at least 6 amino acid residues. Preferably, B will not contain 3 adjacent amino acids that are all are basic amino acids. In addition, when B comprises two or more Cys residues that form one or more disulfide bonds, said disulfide bond(s) is not necessary for the existence of the cyclic molecule of Formula (I). In other words, cleavage of such disulfide bond(s) does not result in the loss of the ring formed by joining M' and W of Formula (I).

In one embodiment, the bridge will preferably comprise long chain omega-amino acids in which amino and carboxyl groups are separated by from about 4 to about 6 methylene groups or a combination of said omega-amino acids and aminobenzoic acids.

In another embodiment, which is a preferred embodiment, the bridging moiety will contain all covalent bonds, such as an amide bond. For example, the bridge can comprise an amide formed through the chemical coupling of a side-chain amino group of amino acids such as Lys or Orn, and a side-chain carboxyl group of the amino acid residue such as Asp or Glu. Alternatively, the bridging moiety can comprise an amide formed between the amino and carboxylate groups attached to the α-carbon of the bridging moiety amino acids. (Hereafter referred to as the "α-amino" moiety of an amino acid or the "α-carboxyl" moiety of an amino acid.) In another alternative, the bridging moiety can comprise an amide formed between any combination of the side-chain amino group or side-chain carboxyl group and the α-amino and the α-carboxyl moieties. The bridging residues may be amine- or carboxyl-containing structures other than natural amino acids, including, e.g., 6-aminohexanoic acid as an amine-containing residue and succinic acid as a carboxyl-containing residue. Furthermore, the invention allows for bridging of the Tyr-Phe-Arg-Trp core sequence using other types of chemical functionalities. In this case, these bridging residues may contain a variety of groups and substituents, including aliphatic, aromatic and heterocyclic moieties. When covalently linked, the bridge can be connected through a variety of linkages including but not limited to amide, ester, ether, thioether, aminoalkyl or aminoaryl bonds. When B is a covalent bond, preferred are compounds having from about 24 to about 30 ring atoms, more preferred are compounds having from about 25 to about 27 ring atoms.

The bridging moiety can alternatively be an ionic bond/association that favors a cyclic structure. This "ionic" bridge is comprised of salt-forming basic and acid functionalities. For example, the bridge can comprise an ionic bond formed between the side-chain amino group of amino acids such as Lys or Orn, and the side-chain carboxyl group of the amino acid residue such as Asp or Glu. Alternatively, the bridging moiety can comprise an ionic bond formed between the amino and carboxylate groups attached to the α-carbon of the bridging moiety amino acids. In another alternative, the bridging moiety may comprise an amide formed between any combination of the side-chain amino group or side-chain carboxyl and the α-amino and the α-carboxyl moieties. Since an ionic bond is typically weaker than a covalent bond, it is easier to distort the topography of a cyclic structure based on such an ionic bond. This distortion may occur when additional groups are attached to the bridging moiety, thereby negatively impacting interaction with the receptor. Thus, the bridging moiety preferably will not be substituted with more than 3 amino acid residues when the moiety is in the form of an ionic bond. In one particularly preferred aspect, when B is an ionic bond, the compounds will have from about 26 to about 29 ring atoms.

It will be recognized that any free peptidic α-carboxy and α-amino groups (i.e., amino acid α-carboxy and α-amino groups) not involved in formation of the ring can optionally be in the form of a carboxyamide or an acylamino moiety, respectively.

In addition to the compounds described by Formula (I), it is envisioned that the core peptide residues can be pegylated to provide enhanced therapeutic benefits such as, for example, increased efficacy by extending half life in vivo. Peptide pegylation methods are well known in the literature. For example pegylation of peptides is described in the following references, the disclosure of each of which is incorporated herein by reference: Lu, Y. A. et al., "Pegylated peptides. II. Solid-phase synthesis of amino-, carboxy- and side-chain pegylated peptides", *Int. J. Pept. Protein Res.*, Vol. 43(2), pp. 127–38 (1994); Lu, Y. A. et al., "Pegylated peptides. 1. Solid-phase synthesis of N alpha-pegylated peptides using Fmoc strategy", *Pept. Res.*, Vol. 6(3), pp. 140–6 (1993); Felix, A. M. et al., "Pegylated peptides. IV. Enhanced biological activity of site-directed pegylated GRF analogs.", *Int. J. Pept. Protein Res.*, Vol. 46(3–4), pp. 253–64 (1995); Gaertner, H. F. et al., "Site-specific attachment of functionalized poly(ethylene glycol) to the amino terminus of proteins", *Bioconjug Chem.*, Vol. 7(1), pp. 38–44 (1996); Tsutsumi, Y. et al., "PEGylation of interleukin-6 effectively increases its thrombopoietic potency", *Thromb Haemost*, Vol. 77(1), pp. 168–73 (1997); Francis, G. E. et al., "PEGylation of cytokines and other therapeutic proteins and peptides: the importance of biological optimisation of coupling techniques", *Int. J. Hematol.*, Vol. 68(1), pp. 1–18 (1998); Roberts, M. J. et al., "Attachment of degradable poly(ethylene glycol) to proteins has the potential to increase therapeutic efficacy", *J. Pharm. Sci.*, Vol 87(11), pp. 1440–45 (1998); and Tan, Y. et al., "Polyethylene glycol conjugation of recombinant methioninase for cancer therapy", *Protein Expr. Purif.*, Vol. 12(1), pp. 45–52 (1998). The compounds of Formula (I) can be pegylated directly, or a "linker arm" may be added to the compounds to facilitate pegylation.

With reference to Formula (I), the following is a non-limiting list of preferred substituents:

For m, n, and q, preferred is 1. For p, preferred is 3.

For X, preferred substituents are hydrogen, hydroxy, halo, —$OR^8$, —$NR^8R^{8'}$, alkyl, cyano, nitro, aryl, heteroaryl, cycloalkyl, and heterocycloalkyl; more preferred is where X is hydrogen, hydroxy, halo, —$OR^8$, —$NR^8R^{8'}$, alkyl, cyano or nitro; most preferred is where X is hydrogen. For $R^8$ and $R^{8'}$ preferred are hydrogen, alkyl, acyl, aryl, and cycloalkyl; more preferred is where $R^8$ is hydrogen and $R^{8'}$ is hydrogen, alkyl or acyl. Also preferred is where two X moieties form a fused ring with the depicted phenyl ring.

For E, preferred substituents are halo, especially fluoro, chloro and bromo; —OH; —SH; —$OR^{13}$; —$SR^{13}$; —$NHR^{13}$, where $R^{13}$ is preferably acyl; —$NHSO_2R^{13'}$; —$(CH_2)_r$—$PO_2HR^{15}$ where r is 0 to about 10 and $R^{15}$ is selected from —OH, hydrogen and alkyl; alkyl; cyano; nitro; and $CF_3$, $R^{13''}$ is preferably selected from hydrogen and alkyl. Most preferred is —OH.

For Z, preferred substituents are hydrogen, hydroxy, halo, —$OR^9$, —$NR^9R^{9'}$, alkyl, cyano, nitro, aryl, heteroaryl, cycloalkyl, and heterocycloalkyl; more preferred is where Z is hydrogen, hydroxy, halo, —$OR^9$, —$NR^9R^{9'}$, alkyl, cyano or nitro; most preferred is where Z is hydrogen. For $R^9$ and $R^{9'}$ preferred are hydrogen, alkyl, acyl, aryl, and cycloalkyl; more preferred is where $R^9$ is hydrogen and $R^{9'}$ is hydrogen, alkyl or acyl. Also preferred is where two Z moieties form a fused ring with the depicted phenyl ring.

For each existence of $R^1$ and $R^{1'}$, preferred are hydrogen and alkyl. Alternative preferred compounds are those where an $R^1$ and $R^2$, together with the atoms to which they are bonded, join to form a heterocycloalkyl or a heteroaryl ring.

For D, preferred is —$N(R^2)C(=NR^3)NR^4R^5$.

For each of $R^2$ and $R^3$, when present, preferred are hydrogen and alkyl, more preferred is hydrogen. Alternative preferred compounds are those where $R^2$ and $R^4$, together with the atoms to which they are bonded, join to form a heterocycloalkyl or a heteroaryl ring.

For each $R^4$ and $R^5$, when present, preferred are hydrogen and alkyl, most preferred is hydrogen.

For G, preferred are optionally substituted naphthylene rings and optionally substituted indoles (i.e., the residue of Formula (I) is Trp); more preferred is an optionally substituted indole.

For each $R^{11}$ preferred are hydrogen and alkyl, more preferred is hydrogen.

For each R, preferred are hydrogen, alkyl and cycloalkyl; most preferred is hydrogen.

For B, preferred is where B results in a compound having greater than about 25 ring atoms. In one aspect, preferred are compounds having greater than about 25 ring atoms and B consists of amino acid (natural or unnatural, e.g., α, β, γ, etc.) residues, preferably 3–5 residues, more preferably 3 or 4 residues. Preferred are compounds where B is a covalently bonded bridge. Most preferred is where B comprises three amino acids wherein an intramolecular amide is formed through the chemical coupling of a side-chain amino group of one of the amino acids (e.g. Lys or Orn), and a side-chain carboxyl group of a second amino acid residue (e.g. Asp or Glu).

A preferred subclass of compounds of Formula (I) are compounds having a structure of Formula (A) as follows:

(A)

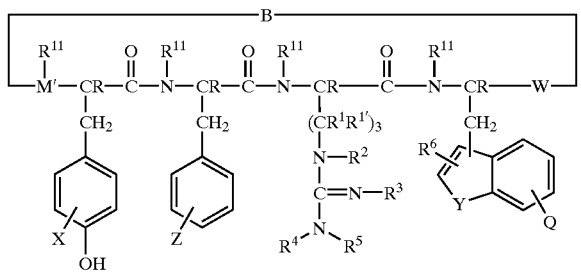

where B, X, Z, M', W, R, R$^1$, R$^{1'}$, R$^2$, R$^3$, R$^4$, R$^5$ and R$^{11}$ are as described above; R$^6$ is selected from hydrogen, alkyl, hydroxy, alkoxy, aryl, heteroaryl, halogen, and SO$_x$R$^{12}$ where x is 0, 1 or 2 and R$^{12}$ is aryl; Y is selected from —NR$^7$—, —CR$^7$R$^{7'}$, —CR$^7$=CR$^{7'}$, —CR$^7$=N— and —N=CR$^{7'}$—, wherein R$^7$ and R$^{7'}$ are independently selected from hydrogen, alkyl, aryl, and heteroaryl, or R$^7$ or R$^{7'}$ is a covalent bond that links Y to the R$^6$ or —CH$_2$— moiety depicted in Formula (A); and Q is one or more substituents independently selected from hydrogen, hydroxy, halo, thiol, —OR$^{10}$, —SR$^{10}$, —NR$^{10}$R$^{10'}$, alkyl, alkene, alkyne, cyano, nitro, aryl, heteroaryl, cycloalkyl, and heterocycloalkyl; where each R$^{10}$ and R$^{10'}$ is independently selected from alkyl, heteroalkyl, aryl, heteroaryl, cycloalkyl, and heterocycloalkyl; or two Q moieties can form a fused ring with the depicted phenyl ring. With reference to Formula (I), in this subclass of Formula (A), m, n and q are all 1, p is 3, D is an optionally substituted guanidino moiety and G is an optionally substituted 11 or 12 membered bicyclic aryl or heteroaryl.

Another preferred sub-class of compounds of Formula (I) are compounds having a structure according to Formula (B), as follows:

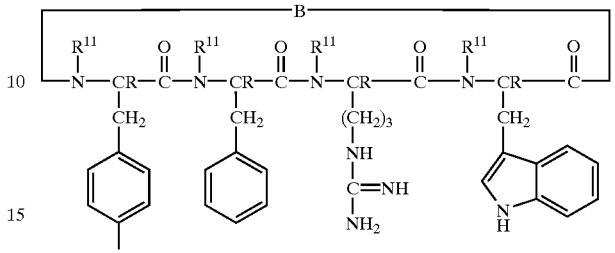

where R, R$^{11}$ and B are as defined above.

The following is a non-limiting list of preferred substituents for the moieties of the Formula (A) compounds:

For Q, preferred substituents are hydrogen, hydroxy, halo, —OR$^{10}$, —NR$^{10}$R$^{10'}$, alkyl, cyano, nitro, aryl, heteroaryl, cycloalkyl, and heterocycloalkyl; more preferred are hydrogen, hydroxy, halo, —OR$^{10}$, —NR$^{10}$R$^{10'}$, alkyl, cyano, and nitro; most preferred is where Q is hydrogen. For R$^{10}$ and R$^{10'}$, preferred are hydrogen, alkyl, acyl, heteroalkyl, aryl, heteroaryl, cycloalkyl, and heterocycloalkyl; more preferred is where R$^{10}$ is hydrogen and R$^{10'}$ is hydrogen, alkyl or acyl. Also preferred is where two Q moieties form a fused ring with the depicted bicyclic ring.

For R$^6$, preferred are hydrogen and alkyl, more preferred is hydrogen.

For R$^7$, preferred are hydrogen, alkyl and aryl, more preferred is hydrogen.

The following is a non-limiting list of preferred cyclic compounds of the present invention. (The use of brackets ([ ]) denotes amino acid points of cyclization, where possible, via side-chain moieties. Where typical amino acid termini capping groups are indicated, e.g Ac— or —NH$_2$ (carboxamide capping group), these capping groups are utilized on the peptidic α-carboxy or α-amino groups.) In this list, "Nal" refers to naphthylalanine and "Orn" refers to ornithine.

aDYfRWK—NH$_2$
a[DY(D-2-Nal)RWK]—NH$_2$
Ac-a[DYfRWK]—NH$_2$
Ac-a[DY(D-1-Nal)RWK]—NH$_2$
Ac-a[EYfRWG(Orn)]-NH$_2$
Ac-GGGa[DYfRWGK]—NH$_2$
AC-aEYfRWGK—NH$_2$
Ac-a[DYfRWGK]—NH$_2$
Ac-aDYfRWG(Orn)-NH$_2$
Ac-aEYfRWG(Orn)-NH$_2$
Ac-a[EFfRWGK]—NH$_2$
Ac-a[DyfRWGK]—NH$_2$
Ac-a[DYyRWGK]—NH$_2$
Ac-a[DY(D-Phe(4-I))RWGK]—NH$_2$
Ac-a[DY(D-Phe(4-I))RWG(Orn)]-NH$_2$
Ac-[DY(D-Phe(4-I))RWG(Orn)]-NH$_2$
Ac-[EYfRWG(Orn)]-NH$_2$
[GYfRWGGG]
[GGYfRWGGGG]

a[DYfRWK]—NH$_2$
Ac-aDYfWK—NH$_2$
Ac-a[DY(D-Phe(4-Cl))RWK]—NH$_2$
Ac-[EYfRWGK]—NH$_2$
Ac-SYSa[DYfRWGK]—NH$_2$
Ac-[DY(D-1-Nal)RWGK]—NH$_2$
Ac-aDYfRWGK—NH$_2$
Ac-a[EYfRWGK]—NH$_2$
Ac-a[DYfRWG(Orn)]-NH$_2$
Ac-a[EYfRWG(Orn)]-NH$_2$
Ac-a[DFfRWGK]—NH$_2$
Ac-[DYfRWGK]—NH$_2$
Ac-a[DY(D-Phe(4-1))RWGK]—NH$_2$
Ac-a[EY(D-Phe(4-1))RWGK]—NH$_2$
Ac-[EY(D-Phe(4-1))RWGK]—NH$_2$
Ac-[EYfRWGK]—NH$_2$
Ac-[DYfRWG(Orn)]-NH$_2$
[GGYfRWGGG]
[GGYfRWGK]—NH$_2$

-continued

[GGYfRWGK]—OH
[GGYfRWGLAG]
[AGYfRWGGG]
Ac-[D(Tyr(3-OH)fRWGK]—NH$_2$
Ac-DYfWK—NH$_2$
Ac-EYfRWGOrn-NH$_2$
Ac-[DY(D-Phe(4-Cl))RWK]—NH$_2$
Ac-[DY(D-Phe(4-Cl)))RWGK]—NH$_2$
Ac-a[DYfR(Trp(5-Br)GK]—NH$_2$
Ac-a[DYfR(Trp(5-OMe)GK]—NH$_2$
Ac-a[DYfR(Trp(6-F)GK]—NH$_2$
Ac-a[DYfR(Trp(4-F)GK]—NH$_2$
Ac-a[DYfR(Trp(7-Me)GK]—NH$_2$
Ac-a[EYfR(Trp(6-OH))G(Orn)]-NH$_2$
Ac-a[E(Tyr(Me))fRWG(Orn)]-NH$_2$
Ac-[E(Tyr(2-Br))fRWG(Orn)]-NH$_2$
Ac-[E(Tyr(3-I))fRWG(Orn)]-NH$_2$
Ac-[D(Tyr(3-NO$_2$))fRWGK]—NH$_2$
Ac-[D(Tyr(3-MeO))fRWGK]—NH$_2$
Ac-a[DY(D-Phe(5-Br))RWGK]—NH$_2$
Ac-a[DY(D-Phe(4-NO$_2$))RWGK]—NH$_2$
Ac-[DY(D-Phe(2,5-OH))RWGK]—NH$_2$
Ac-[DY(D-Phe(5-F))RWGK]—NH$_2$
Ac-[EY(D-Phe(3-NH$_2$))RWGOrn]-NH$_2$
Ac-[EY(D-Phe(3-I))RWGOrn]-NH$_2$
Ac-[DYfRW(Gly-N—CH$_3$))K]-NH$_2$
Ac-[E(Phe(4-Br))fRWGK]—NH$_2$
Ac-a[DYFRW(Gly-(N—CH$_3$))K]—NH$_2$
Ac-a[D(Phe(4-Cl))FRWGK]—NH$_2$
Ac-[D(Phe(4-Br))FRWGK]—NH$_2$
Ac-[D(Phe(4-F))fRWGK]—NH$_2$
Ac-[D(Phe(4-F))FRWGK]—NH$_2$
Ac-[D(Phe(4-NO$_2$))fRWGK]—NH$_2$
Ac-[D(Phe(4-NH$_2$))fRW(Gly-(N—CH$_3$))K]—NH$_2$
Ac-[D(Phe(4-Cl))fRW(Gly-(N—CH$_3$))K]—NH$_2$
[D(Phe(4-NO$_2$))fRW(Gly-(N—CH$_3$))K]—NH$_2$
Ac-[D(Phe(4-NHCOCH$_3$))fRW(Gly-(N—CH$_3$))K]—NH$_2$
Ac-a[E(Phe(4-Cl))fRW(Gly-(N—CH$_3$))K]—NH$_2$
Ac-a[E(Phe(4-Cl))fRW(Gly-(N—CH$_3$))(Orn)]-NH$_2$
Ac-[E(Phe(4-Cl))fRW(Gly-(N—CH$_3$))(Orn)]-NH$_2$
Ac-a[D(Phe(4-F))fRW(Gly-(N—CH$_3$))K]—NH$_2$
Ac-a[D(Phe(4-F))FRW(Gly-(N—CH$_3$))K]—NH$_2$
Bc-DYfRW(Gly-(N—CH$_3$))K—NH$_2$
Bc-EYfRW(Gly-(N—CH$_3$))K—NH$_2$
Bc-EYfRWGK—NH$_2$
Bc-D(Phe(4-Cl))fRW(Gly-(N—CH$_3$))K—NH$_2$
Bc-D(Phe(4-Cl))fRWGK—NH$_2$
Bc-E(Phe(4-Cl))fRW(Gly-(N—CH$_3$))K—NH$_2$
Bc-[D(Phe(4-Cl))fRW(Gly-(N—CH$_3$))K]—NH$_2$
Bc-[DY(D-2-Nal)RWGK]—NH$_2$
Bc-[DY(L-2-Nal)RWGK]—NH$_2$
Bc-[DY(D-1-Nal)RWGK]—NH$_2$
BC-[DY(Phe(4-Br))RWGK]—NH$_2$
Ac-[DY(D-2-Nal)RWGK]—NH$_2$
Bc-EY(D-2-Nal)RWGK—NH$_2$
Bc-EY(D-2-Nal)RW(Gly-(N—CH$_3$))K—NH$_2$
Ac-[DYf(homo-Arg)WGK]—NH$_2$
Ac-[DYyRWGK]—NH$_2$
Ac-[DYYRWGK]—NH$_2$
DYfRWGK—NH$_2$
Ac-a[DY(D-2-Nal)RWGK]—NH$_2$
Ac-DYfRWGK—NH$_2$
Ac-EYfRWGK—NH$_2$
Ac-EY(D-2-Nal)RWGK—NH$_2$
Ac-[EY(D-2-Nal)RWGK]—NH$_2$
Ac-a[DY(D-2-Nal)RWK]—NH$_2$
a[DY(D-1-Nal)RWK]—NH$_2$
[GGYfRWGGAG]
[GGYfRWGFAG]
[GGYfRWAAA]
Ac-[DF(D-Phe(4-I))RWGK]—NH$_2$
Ac-DYfRWGK—NH$_2$
Ac-a[DY(D-Phe(4-I))RWGK]—NH$_2$
Ac-[D(Tyr(3-OH))fRWGK]—NH$_2$
Ac-a[D(Tyr(Me))fRWGK]—NH$_2$
Ac-a[DYfR(Trp(5-F)GK]—NH$_2$
Ac-a[DYfR(Trp(5-Me)GK]—NH$_2$
Ac-a[DYfR(Trp(1-Me)GK]—NH$_2$
Ac-a[DYfR(Trp(6-Br)GK]—NH$_2$
Ac-a[EYfR(Trp(5-OH))G(Orn)]-NH$_2$
Ac-a[EYfR(Trp(6-Cl))G(Orn)]-NH$_2$
Ac-a[E(Tyr(CH$_2$Ph))fRWG(Orn)]-NH$_2$
Ac-[E(Tyr(3-F))fRWG(Orn)]-NH$_2$
Ac-[E(Tyr(2,5-OH))fRWG(Orn)]-NH$_2$
Ac-[D(Tyr(3-NH$_2$))fRWGK]—NH$_2$
Ac-[D(Tyr(3-Cl))fRWGK]—NH$_2$
Ac-a[DY(D-Phe(4-NH$_2$))RWGK]—NH$_2$
Ac-[DY(D-Phe(4-F))RWGK]—NH$_2$
Ac-[DY(D-Phe(3-F))RWGK]—NH$_2$
Ac-[EY(D-Phe(3-MeO))RWGOrn]-NH$_2$
Ac-[EY(D-Phe(3-NO$_2$))RWGOrn]-NH$_2$
Ac-[D(Phe(4-Cl))fRWGK]—NH$_2$
Ac-[D(Phe(4-NH$_2$))fRWGK]—NH$_2$
Ac-a[D(Phe(4-Cl))fRWGK]—NH$_2$
Ac-[DYFRW(Gly-(N—CH$_3$))K]—NH$_2$
Ac-[D(Phe(4-Cl))FRWGK]—NH$_2$
Ac-[D(Phe(4-CN))fRWGK]—NH$_2$
Ac-[E(Phe(4-F))fRWG(Orn)]-NH$_2$
Ac-[DYf(Arg-(N—CH$_3$))WGK]—NH$_2$
Bc-[DYfRWGK]—NH$_2$
Bc-DYfRWGK—NH$_2$
Bc-[DYfRW(Gly-(N—CH$_3$))K]—NH$_2$Ac—
Bc-aEYfRWGK—NH$_2$ In the following specific examples of compounds of the present invention, absence of a "D" or "L" designation refers to the L-form.
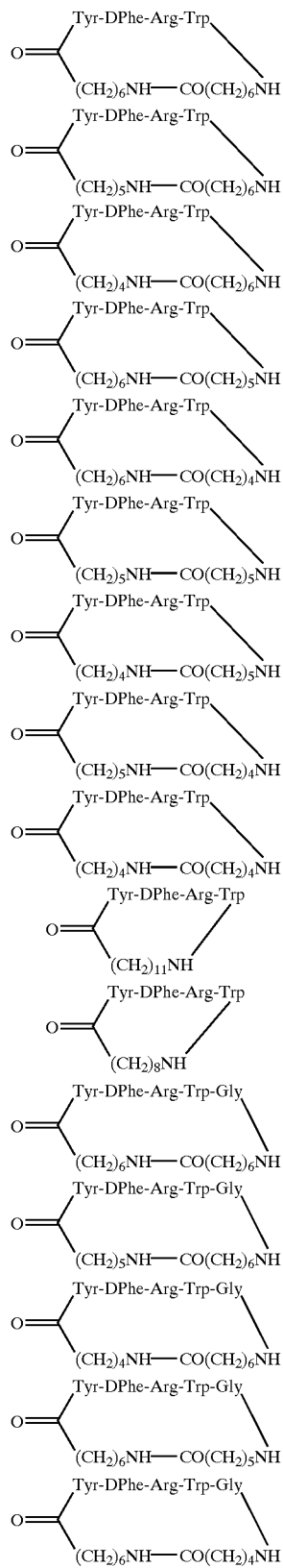
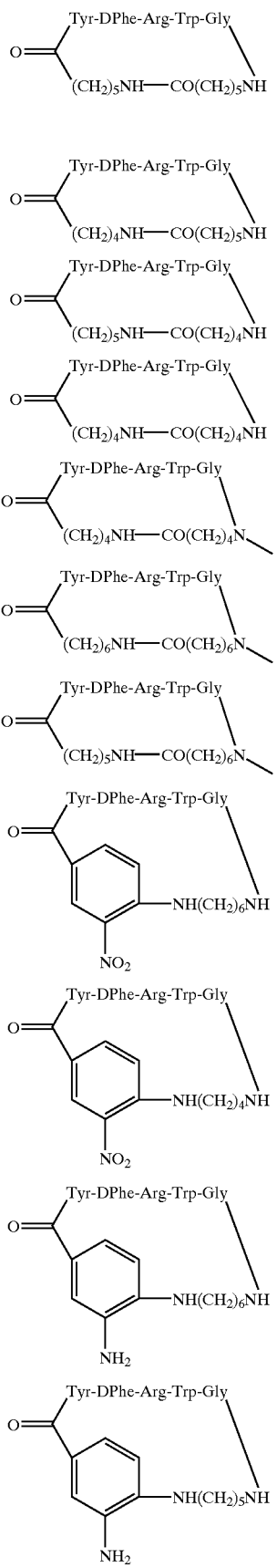

-continued
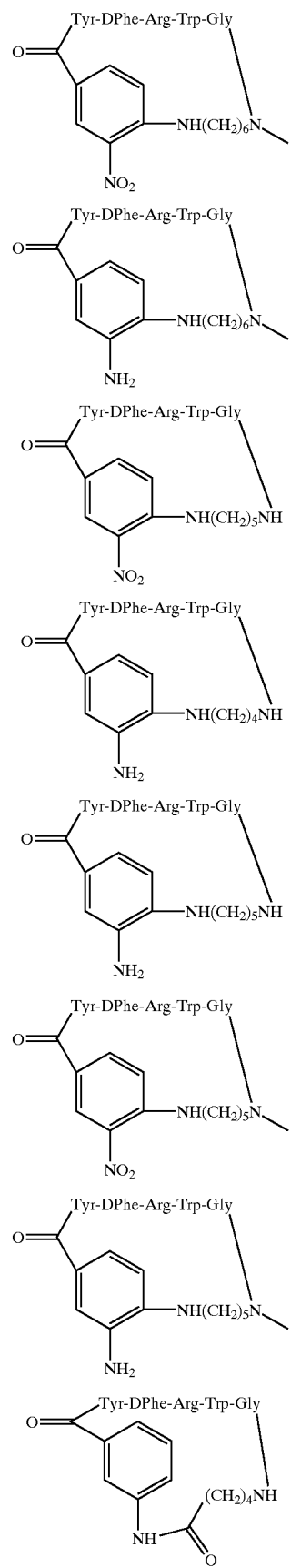
-continued
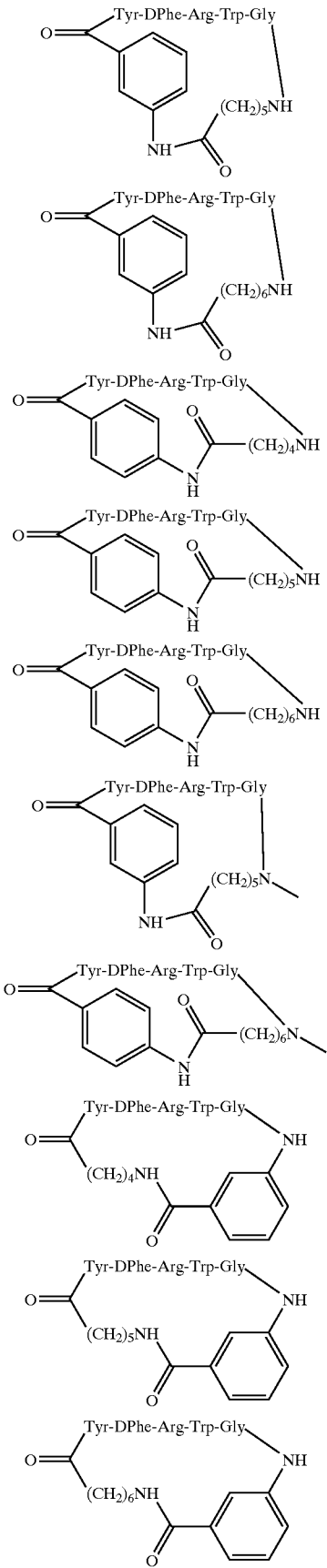

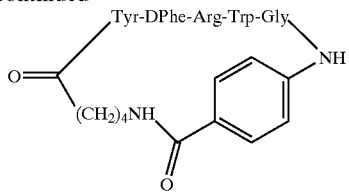
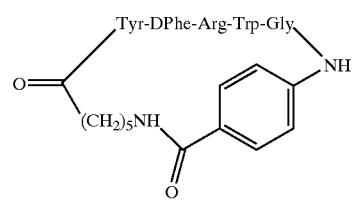
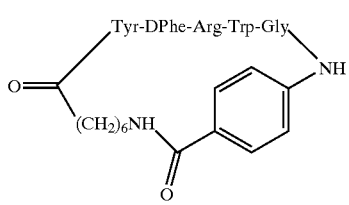
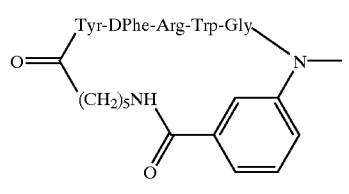
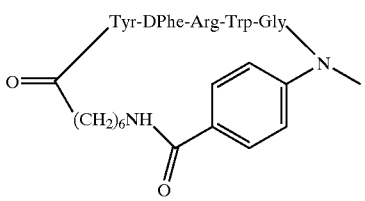
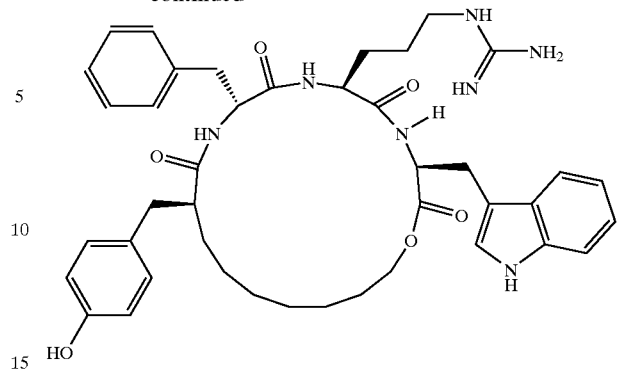
N-{3-[9-Benzyl-12-(4-hydroxy-benzyl)-3-(1H-indol-3-ylmethyl)-2,5,8,11-tetraoxo-1-oxa-4,7,10-triaza-cyclononadec-6-yl]-propyl}-guanidine
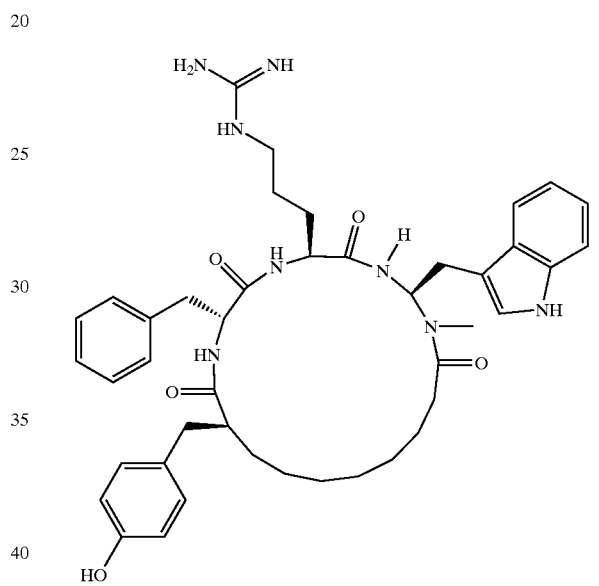
N-{3-[2-Benzyl-24-(4-hydroxy-benzyl)-8-(1H-indol-3-ylmethyl)-10-methyl-3,6,11,25-tetraoxo-1,4,7,10-tetraaza-cyclopentacos-5-yl]-propyl}-guanidine
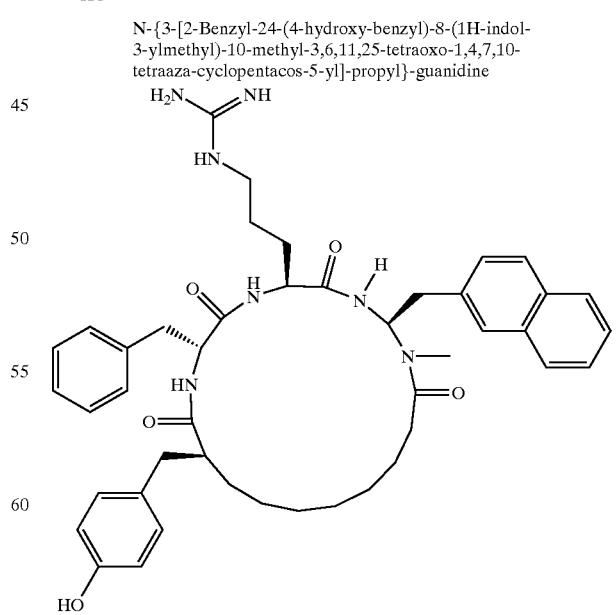
N-{3-[2-Benzyl-24-(4-hydroxy-benzyl)-10-methyl-8-naphthalen-2-ylmethyl-3,6,11,25-tetraoxo-1,4,7,10-tetraaza-cyclopentacos-5-yl]-propyl}-guanidine

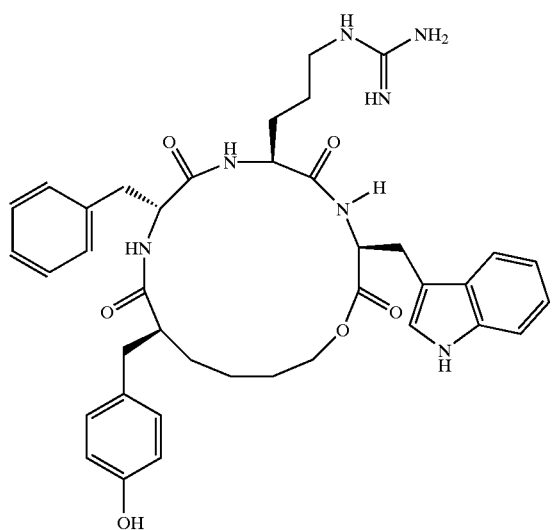

N-{3-[9-Benzyl-12-(4-hydroxy-benzyl)-3-(1H-indol-3-ylmethyl)-2,5,8,11-tetraoxo-1-oxa-4,7,10-triaza-cyclohexadec-6-yl]-propyl}-guanidine

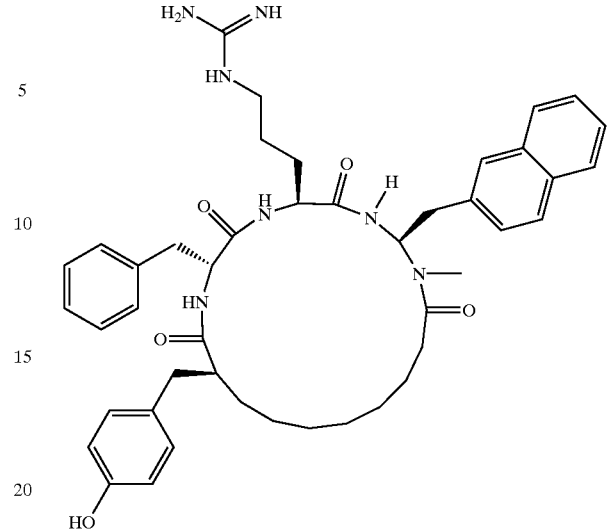

N-{3-[9-Benzyl-12-(4-hydroxy-benzyl)-3-naphthalen-2-ylmethyl-2,5,8,11-tetraoxo-1-oxa-4,7,10-triaza-cyclopentacos-6-yl]-propyl}-guanidine

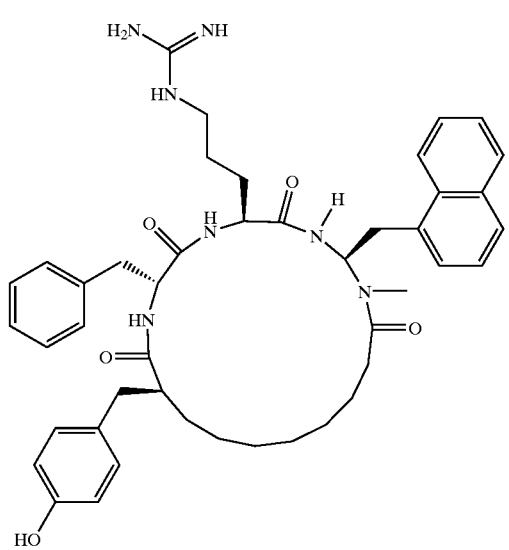

N-{3-[2-Benzyl-24-(4-hydroxy-benzyl)-10-methyl-8-naphthalen-1-ylmethyl-3,6,11,25-tetraoxo-1,4,7,10-tetraaza-cyclopentacos-5-yl]-propyl}-guanidine

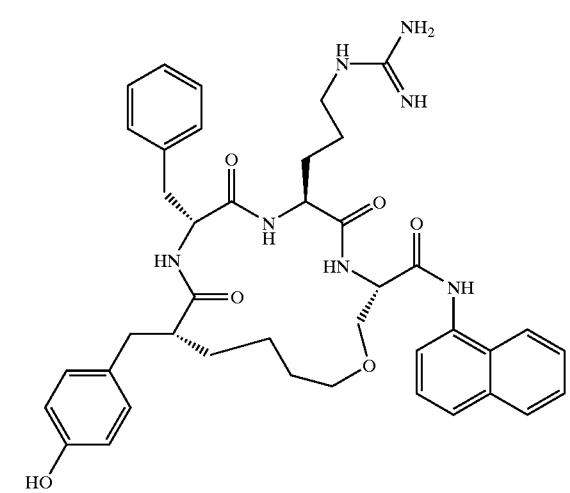

9-Benzyl-6-(3-guanidino-propyl)-12-(4-hydroxy-benzyl)-5,8,11-trioxo-1-oxa-4,7,10-triaza-cyclohexadecane-3-carboxylic acid naphthalen-1-ylamide

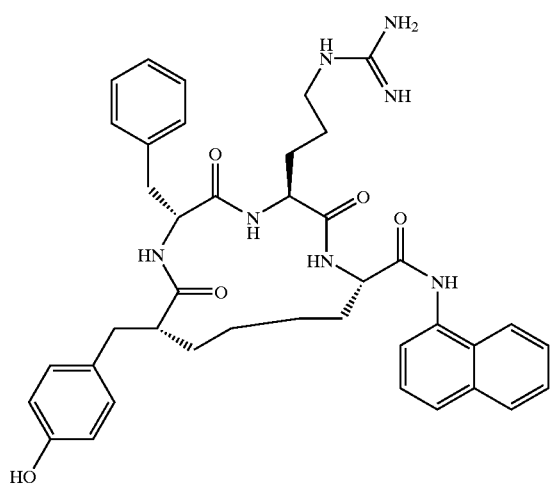

2-Benzyl-5-(3-guanidino-propyl)-13-(4-hydroxy-benzyl)-3,6,14-trioxo-1,4,7-triaza-cyclotetradecane-8-carboxylic acid naphthalen-1-ylamide

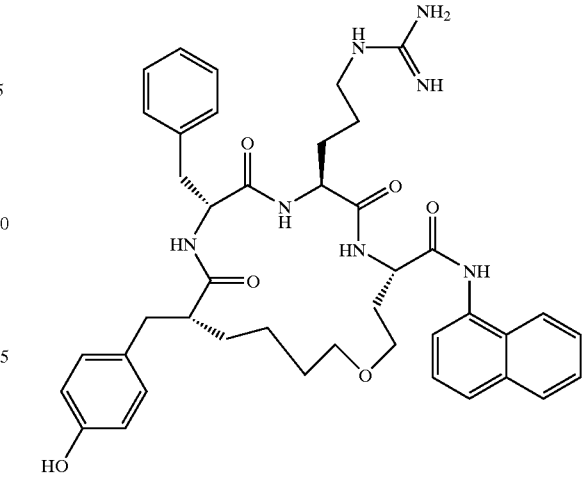

10-Benzyl-7-(3-guanidino-propyl)-13-(4-hydroxy-benzyl)-6,9,12-trioxo-1-oxa-5,8,11-triaza-cyclopentadecane-4-carboxylic acid naphthalen-1-ylamide

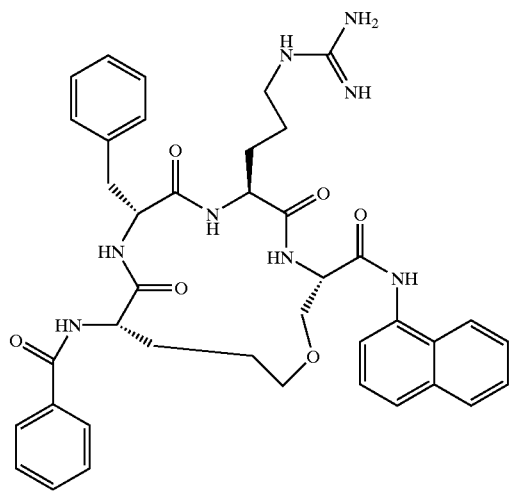

12-Benzoylamino-9-benzyl-6-(3-guanidino-propyl)-5,8,11-trioxo-1-oxa-4,7,10-triaza-cyclopentadecane-3-carboxylic acid naphthalen-1-ylamide

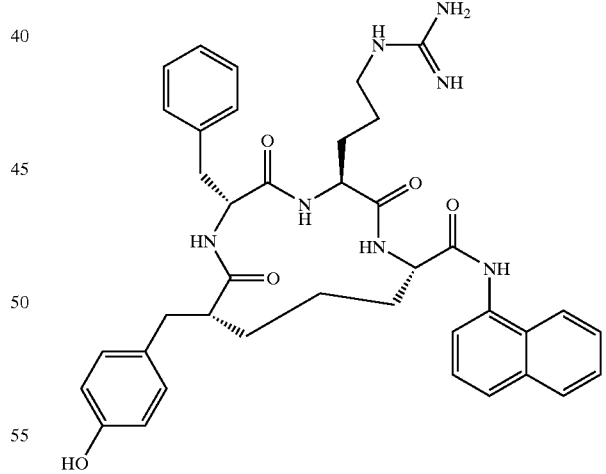

2-Benzyl-5-(3-guanidino-propyl)-12-(4-hydroxy-benzyl)-3,6,13-trioxo-1,4,7-triaza-cyclotridecane-8-carboxylic acid naphthalen-1-ylamide

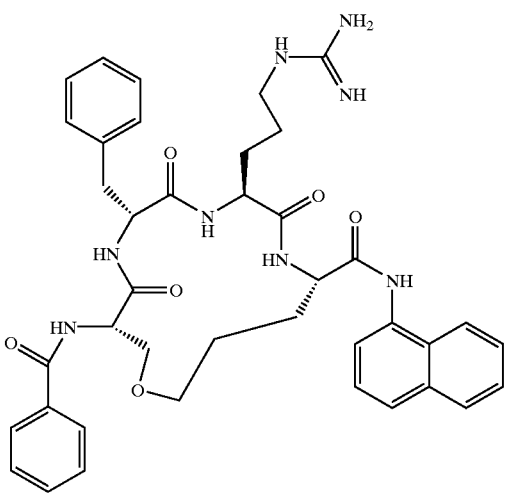

3-Benzoylamino-6-benzyl-9-(3-guanidino-propyl)-4,7,10-trioxo-1-oxa-5,8,11-triaza-cyclopentadecane-12-carboxylic acid naphthalen-1-ylamide

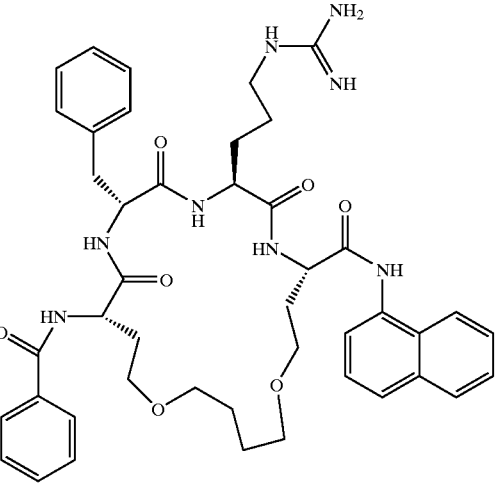

13-Benzoylamino-10-benzyl-7-(3-guanidino-propyl)-6,9,12-trioxo-1,16-dioxa-5,8,11-triaza-cycloeicosane-4-carboxylic acid naphthalen-1-ylamide

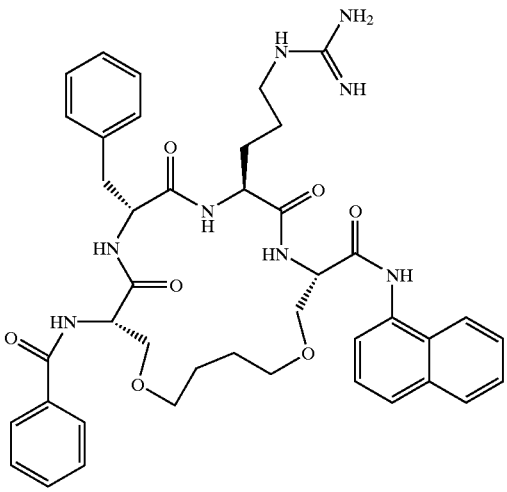

12-Benzoylamino-9-benzyl-6-(3-guanidino-propyl)-5,8,11-trioxo-1,14-dioxa-4,7,10-triaza-cyclooctadecane-3-carboxylic acid naphthalen-1-ylamide

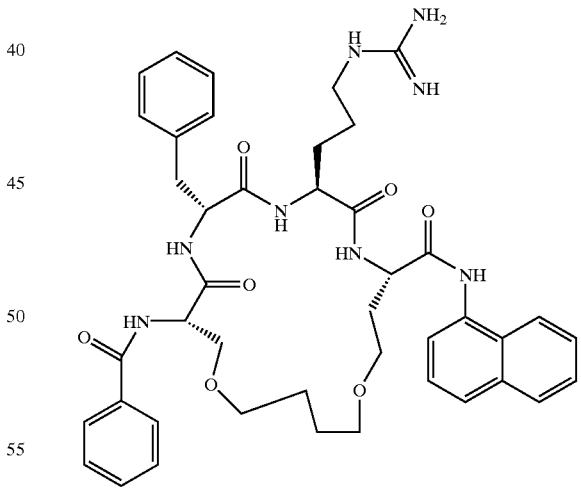

13-Benzoylamino-10-benzyl-7-(3-guanidino-propyl)-6,9,12-trioxo-1,15-dioxa-5,8,11-triaza-cyclononadecane-4-carboxylic acid naphthalen-1-ylamide -continued

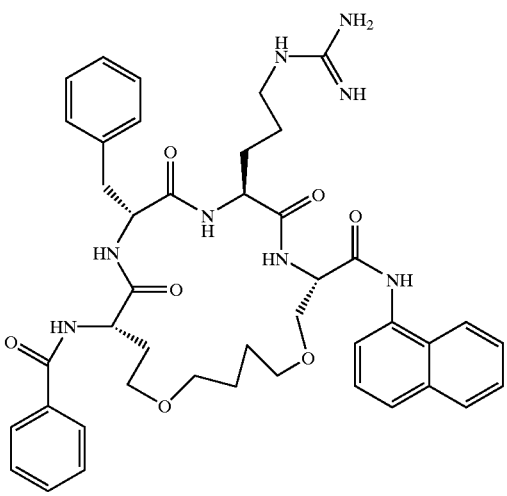

12-Benzoylamino-9-benzyl-6-(3-guanidino-propyl)-5,8,11-trioxo-1,15-dioxa-4,7,10-triaza-cyclononadecane-3-carboxylic acid naphthalen-1-ylamide

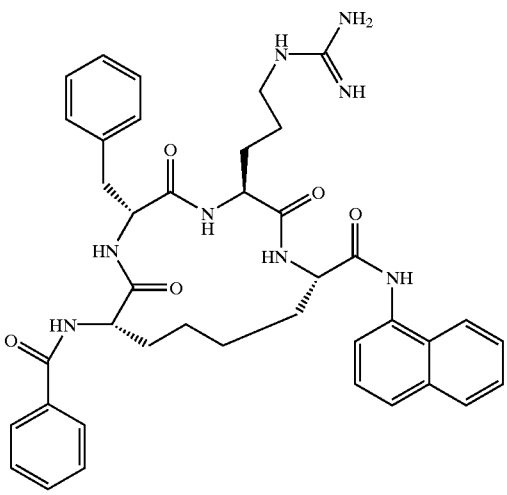

13-Benzoylamino-2-benzyl-5-(3-guanidino-propyl)-3,6,14-trioxo-1,4,7-triaza-cyclotetradecane-8-carboxylic acid naphthalen-1-ylamide -continued

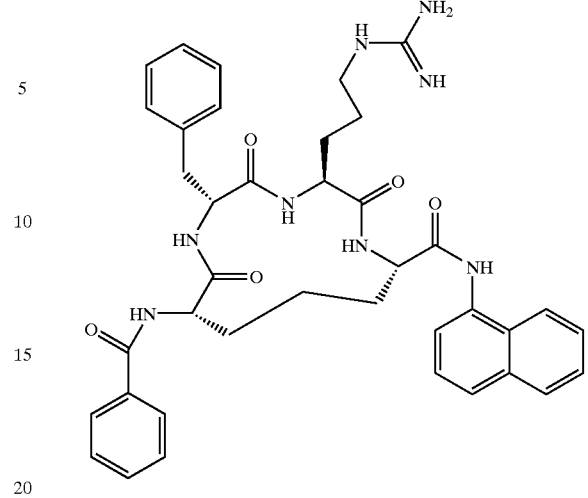

12-Benzoylamino-2-benzyl-5-(3-guanidino-propyl)-3,6,13-trioxo-1,4,7-triaza-cyclotridecane-8-carboxylic acid naphthalen-1-ylamide

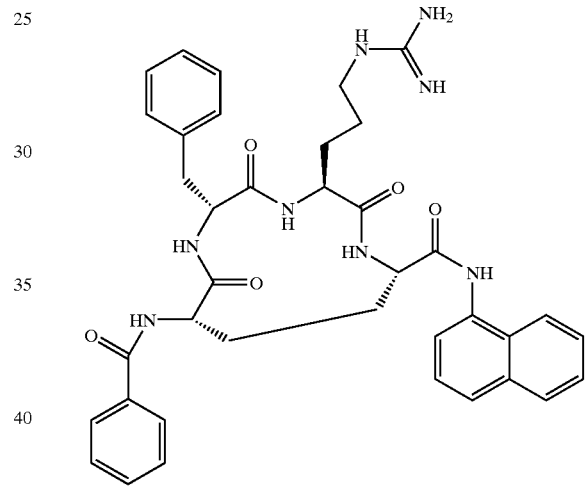

11-Benzoylamino-2-benzyl-5-(3-guanidino-propyl)-3,6,12-trioxo-1,4,7-triaza-cyclododecane-8-carboxylic acid naphthalen-1-ylamide

III. Synthesis of the Compounds

The compounds of the invention can be prepared using a variety of procedures. The starting materials used in preparing the compounds of the invention are known, made by known methods, or are commercially available. A general reaction for making the compounds is set forth below. Representative examples for synthesizing representative compounds of the present invention are disclosed in Examples 1–18.

According to one general scheme, the claimed peptides are synthesized using Fmoc (9-Fluorenylmethoxycarbonyl as protection group for alpha $NH_2$) chemistry followed by deprotection, solution phase cyclization and detailed characterization and purification. One general synthesis scheme for the claimed compounds is as follows:

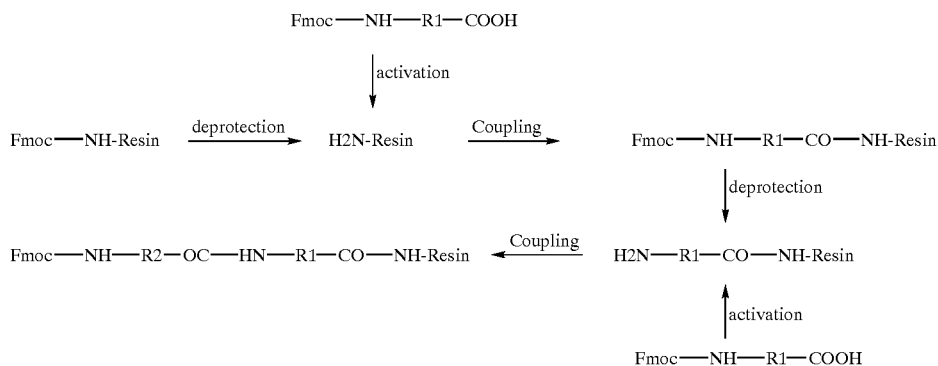

The R-group designations in the above scheme do not correspond to the R groups used to define the Formula (I) compounds.

Linear Peptide Synthesis: The linear version of the compounds are synthesized with a Perkin-Elmer Applied Biosystem Division (PE-ABD) Model 433 automated synthesizer. All the reagents used for peptide synthesis, Fmoc amino acids (except Fmoc-L-Arg-Pbf is from AnaSpec) and resins can be purchased from PE-ABD. Standard 0.1 mmole FastMoc chemistry with single coupling is used. The general Fmoc chemistry protocol for SPPS (solid phase peptide synthesis) includes: 1) cleavage of the Fmoc protection groups with piperidine; 2) activation of the carboxyl group of amino acids; and 3) coupling of the activated amino acids to the amino-terminal of the resin bound peptide chain to form peptide bonds. FastMoc cycles in which amino acids are activated with 2-(1H-benzotriazol-1-yl)-1,1,3,3-tetramethyluronium hexafluorophosphate (HBTU). 1.0 mmole of dry protected amino acid in a cartridge is dissolved in a solution of HBTU, N,N-diisopropylethylamine (DIEA), and 1-hydroxybenzotriazole (HOBt) in N,N-dimethylformamide (DMF) with additional N-methylpyrrolidone (NMP) added. The activated Fmoc amino acid is formed almost instantaneously and the solution is transferred directly to the reaction vessel. The step of Fmoc deprotection is monitored and controlled by conductivity measurement. The peptide chain is built on a Rink Amide resin since the C-terminal amide is needed. The acetyl group is added on the N-terminal side of the peptide after the full length of the peptide chain is made. It is accomplished by reaction of acetic anhydrite (4.75% V:V acetic anhydrite, 0.2% HOBt W:V, 2.25% DIEA in NMP) with the α-amino group on N-terminal side of residue. The final synthesis product is washed extensively with NMP and dichloromethane (DCM).

DeDrotection: The resins containing synthesized peptides are unloaded from the synthesizer and briefly air-dried. Using 1.5–2.0 ml of the cleavage cocktail (93% trifluoroacetic acid (TFA), 2.3% ethanodithiol in water) for 1.5–3.0 hours at room temperature, the peptides are cleaved off the resin and at the same time, the side chain protection groups [O-t-butyl (OtBu) for Asp, Glu, Tyr and Ser, pentamethyidihydrobenzofuran-5-sulfonyl (Pbf) for Arg, t-butoxycarbonyl (Boc) for Trp, Orn, Lys] are removed under the deprotection condition. The cleavage solution is separated from the resin by filtration. The filtrate is then diluted with 15 ml of water. Six rounds of ether extraction are performed to clean the peptide product. The peptide is lyophilized and stored at –20° C. before cyclization.

Solution Phase cyclization: The peptide is characterized by reversed phase high performance liquid chromatography (RP-HPLC) and mass spectrometry (MS) prior to cyclization process. The lyophilized peptide is dissolved in cold DMF with addition of dibasic potassium phosphate. Diphenylphosphoryl azide (DPPA, from Sigma), the cyclization reagent, to peptide molar ratio is 4:1. The reaction vessel is chilled with dry ice when the DPPA is introduced. The overall cyclization reaction is carried out in 4° C. for 24 hours with another DPPA addition in 4 hours after the reaction is started. Analytical RP-HPLC and electrospray MS is used to monitor the cyclization reaction. A HP 1090 HPLC system with a Vadyc C-8 column with 2.1 mm ID, 15 cm length, 300 Å pore size, and 10 μm particle size. A uv detector is used for detection of the cyclization process. With the described cyclization protocol, the reaction is completed within 24 hours.

Purification and Characterization: The cyclized peptide product is then lyophilized to remove DMF solvent. The peptide powder along with phosphate salt, DPPA and other by-products are re-dissolved in 50% acetic acid solution and injected onto a Vydac 1.0 cm I.D. 25 cm length C-8 column with 5 μm particle size, and 300 Å pore size for purification. A Beckman System Gold HPLC system with dual wavelength u.v. detector is used. Linear gradient of acetonitrile is programmed and introduced to the column to separate the cyclic peptide product from other substances. The elute is collected by a Pharmacia fraction collector, and the individual separation fractions are subjected to both analytical HPLC and electrospray MS for characterization to ensure the identity and purity.

A variety of additional compounds can be generated using the guidance of the scheme above.

It is recognized that it is preferable to use a protecting group for any reactive functionality such as a carboxyl, hydroxyl and the like. This is standard practice, well within the normal practice of the skilled artisan.

The indicated steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the above general description.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when potentially reactive functionalities on the molecule are masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids with reactive side chains used as starting materials are preferably blocked to prevent undesired side reactions.

IV. Melanocortin Functional Activity and Selectivity

Functional activity can be evaluated using various methods known in the art. Examples of such methods are measurement of second messenger responses, in particular cAMP, the use of modified cell systems yielding color reaction upon accumulation of second messenger elements such as cAMP, e.g. as described by Chen et al. 1995 (Anal Biochem. 1995, 226, 349–54), Cytosensor Microphysiometer techniques (see Boyfield et al. 1996), or the study of physiological effects caused by the compounds of the invention may be applied by using the compounds of the invention alone, or in combination with natural or synthetic MSH-peptides.

The compounds of the present invention will interact preferentially (i.e., selectively) to MC-4 and/or MC-3, relative to the other melanocortin receptors. Selectivity is particularly important when the compounds are administered to humans or other animals, to minimize the number of side effects associated with their administration. MC-3/MC-4 selectivity of a compound is defined herein as the ratio of the $EC_{50}$ of the compound for an MC-1 receptor ("$EC_{50}$-MC-1") over the $EC_{50}$ of the compound for the MC-3 ($EC_{50}$-MC-3)/MC-4 ($EC_{50}$-MC-4) receptor, the $EC_{50}$ values being measured as described above. The formulas are as follows:

MC-3 selectivity=[$EC_{50}$-MC-1]/[$EC_{50}$-MC-3]

MC-4 selectivity=[$EC_{50}$-MC-1]/[$EC_{50}$-MC-4]

A coumpound is defined herein as being "selective for the MC-3 receptor" when the above mentioned ratio "MC-3-selectivity" is at least about 10, preferably at least about 100, and more preferably at least about 500.

A coumpound is defined herein as being "selective for the MC-3 receptor" when the above mentioned ratio "MC-3selectivity" is at least about 10, preferably at least about 100, and more preferably at least about 500.

The fallowing data demostrate both erein as being selective for the representative compounds of the present invention.

The following data demostrate the lack of selectivity over the MC-1 receptor when the Tyr residue of the present compounds is replaced by His in the tetrapeptide

V. Methods of Use and Compositions

Based on their ability to agonize or antagonize the MC-4 and/or MC-3 receptor, the present inventions also relates to the use of the ligands of the present invention in methods for treating obesity as well as other body weight disorders, including anorexia and cachexia. The invention further relates to the treatment of disorders relating to behavior, memory (including learning), cardiovascular function, inflammation, sepsis and septic, cardiogenic and hypovolemic shock, sexual dysfunction, penile erection, muscle atrophy, nerve growth and repair, intrauterine fetal growth, and the like.

The terms treating and treatment are used herein to mean that, at a minimum, administration of a compound of the present invention mitigates a disease state by acting via the MC-3 or MC-4 receptor. Thus, the terms include: preventing a disease state from occurring in a mammal, particularly when the mammal is predisposed to acquiring the disease, but has not yet been diagnosed with the disease; inhibiting progression of the disease state; and/or alleviating or reversing the disease state.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition and *Peptide and Protein Drug Delivery*, Marcel Dekker, N.Y., 1991.

The compositions of the invention comprise:

a. a safe and effective amount of a compound of Formula (I); and b. a pharmaceutically-acceptable excipient.

A "safe and effective amount" of a Formula (I) compound is an amount that is effective to interact with the MC-4 and/or MC-3 receptor, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the excipient employed, the solubility of the Formula (I) compound therein, and the dosage regimen desired for the composition.

In addition to the subject compound, the compositions of the subject invention contain one or more pharmaceutically-acceptable excipients. The term "pharmaceutically-acceptable excipient", as used herein, means one or more compatible solid or liquid ingredients which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable excipients must, of course, be of sufficiently high purity and sufficiently low toxicity to render them suitable for administration to the animal, preferably a mammal, more preferably a human being treated.

Some examples of substances which can serve as pharmaceutically-acceptable excipients or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; vegetable oils, such as peanut oil, cottonseed oil, sesame oil, olive oil, corn oil and oil of theobroma; polyols such as propylene glycol, glycerin, sorbitol, mannitol, and polyethyleneglycol; agar; alginic acid; wetting agents and lubricants, such as sodium lauryl sulfate; coloring agents; flavoring agents; tableting agents, stabilizers; antioxidants; preservatives; pyrogen-free water; isotonic saline; and buffers, such as phosphate, citrate and acetate.

The choice of pharmaceutically-acceptable excipients to be used in conjunction with the subject compound is basically determined by the way the compound is to be administered. If the subject compound is to be injected, the preferred pharmaceutically-acceptable excipient is sterile water, physiological saline, or mixtures thereof, the pH of which has preferably been adjusted to about 4–10 with a pharmaceutical buffer; a compatible suspending agent may also be desirable.

In particular, pharmaceutically-acceptable excipients for systemic administration include sugars, starches, cellulose and its derivatives, malt, gelatin, talc, calcium sulfate, lactose, vegetable oils, synthetic oils, polyols, alginic acid, phosphate, acetate and citrate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 1 mg to about 750 mg, more preferably from about 3 mg to about 500 mg, still more preferably from about 5 mg to about 300 mg, of a Formula (I) compound.

The compositions of this invention may be in any of a variety of forms, suitable (for example) for oral, rectal, topical, nasal, ocular, transdermal, pulmonary or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of excipient employed in conjunction with the Formula (I) compound is sufficient to provide a practical quantity of material for administration per unit dose of the compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms. Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable excipient suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin, polyvinylpyrrolidone and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are seful adjuvants for chewable tablets. Capsules typically comprise one or more solid iluents disclosed above. The selection of excipient components depends on secondary onsiderations like taste, cost, and shelf stability, which are not critical for the purposes of he subject invention, and can be readily made by a person skilled in the art.

Peroral compositions also include liquid solutions, emulsions, suspensions, and the ike. The pharmaceutically-acceptable excipients suitable for preparation of such compositions are well known in the art. Typical components of excipients for syrups, ixirs, emulsions and suspensions include ethanol, glycerol, propylene glycol, lyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben, propyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Because the compounds of the present invention are peptidic in nature, a preferred mode of administration is parenteral (more preferably intravenous injection) or nasal administration, in the form of a unit dose form. Preferred unit dose forms include suspensions and solutions, comprising a safe and effective amount of a Formula 1 compound. When administered parenterally, the unit dose form will most preferably comprise from about 3 to about 300 mg of the Formula (I) compound.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

VI. Methods of Administration

As indicated, compositions of this invention can be administered topically or systemically. Systemic application includes any method of introducing a Formula (I) compound into the tissues of the body, e.g., intra-articular, intrathecal, epidural, intramuscular, transdermal, intravenous, intraperitoneal, subcutaneous, sublingual, rectal, nasal, pulmonary, and oral administration. The Formula (I) compounds of the present invention are preferably administered systemically, more preferably parenterally and most preferably via intravenous injection.

The specific dosage of compound to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 0.003 mg to about 300 mg, more preferably from about 0.03 mg to about 100 mg, of Formula (I) compound are administered per day for systemic administration. It is understood that these dosage ranges are by way of example only, and that daily administration can be adjusted depending on the factors listed above.

As is known and practiced in the art, all formulations for parenteral administration must be sterile. For mammals, especially humans, (assuming an approximate body weight of 70 kilograms) individual doses of from about 0.001 mg to about 100 mg are preferred.

A preferred method of systemic administration is intravenous delivery. Individual doses of from about 0.01 mg to about 100 mg, preferably from about 0.1 mg to about 100 mg are preferred when using this mode of delivery.

In all of the foregoing, of course, the compounds of the invention can be administered alone or as mixtures, and the compositions may further include additional drugs or excipients as appropriate for the indication.

The compound of the invention can be delivered to the preferred site in the body by using a suitable drug delivery system. Drug delivery systems are well known in the art. For example, a drug delivery technique useful for the compounds of the present invention is the conjugation of the compound to an active molecule capable of being transported through a biological barrier (see e.g. Zlokovic, B. V., *Pharmaceutical Research*, Vol. 12, pp. 1395–1406 (1995)). A specific example constitutes the coupling of the compound of the invention to fragments of insulin to achieve transport across the blood brain barrier (Fukuta, M., et al. *Pharmaceutical Res.*, Vol. 11, pp. 1681–1688 (1994)). For general reviews of technologies for drug delivery suitable for the compounds of the invention see Zlokovic, B. V., *Pharmaceutical Res.*, Vol. 12, pp. $13^95$–$1^{406}$ (1995) and Pardridge, W M, *Pharmacol. Toxicol.*, Vol. 71, pp. 3–10 (1992).

VII. Representative Examples

In the following examples the invention will be described in greater detail by reference to a number of preferred embodiments which are only given for purposes of illustration and should not be considered to limit the invention in any way.

The following abbreviations are used in the Examples:

OtBu: tert-butoxy [—O—C(CH$_3$)$_3$] tBu: tert-butyl [—C(CH$_3$)$_3$]

Pbf: penta fluorophenyl Boc: tert-butyloxycarbonyl

TFA: trifluoroacetic acid DMF: N,N-Dimethylformamide

Fmoc: 9-Fluorenylmethoxycarbonyl DPPA: Diphenylphosphoryl azide

HOAt: 1-hydroxy-7-azabenzotriazole HOBt: N-hydroxybenzotriazole

EDCI: 1-(3-dimethylam inopropyl)-3-ethylcarbodiimide hydrochloride

HATU: O-(7-azabenzotiazol-1-yl)-N,N,N',N'-tetramethyluronium hexafluorophosphate Pbf: 2,2,4,6,7-pentamethyl-dihydrobenzofuran-5-sulfonyl- Pmc: 2,2,5,7,8-pentamethyl-chroman-6-sulfonyl Trt: trityl A. Synthetic Examples

EXAMPLE 1

Synthesis of Ac-a[DYfRWGK]-NH$_2$[M+H]$^+$: 1065.2

Based on the 0.55 mmole/g substitution rate for the Rink Amide resin, 0.182 g of the resin is weighted out for 0.1 mmole scale synthesis. The performance of the PE-ABD 433 peptide synthesizer is checked before the run with various flow tests to ensure the accurate reagent delivery. Fmoc amino acids: Asp-OtBu, Tyr-OtBu, Arg-Pbf, Trp-Boc, Lys-Boc, and Gly are purchased commercially in 1 mmole cartridges. Fmoc-ala (311 mg, 1 mmole) and Fmoc-phe (387 mg, 1 mmole) is measured and added in the synthesis cartridges, respectively. The freshly made acetic anhydride solution is loaded on the instrument at 4 bottle position. Other synthesis reagents and solvents are purchased commercially and loaded on the instrument according to the instrument's instruction. A chemistry program called NAc-0.1 mmole MonPrePk is used for synthesizing this peptide. The Fmoc deprotection is monitored and controlled by conductivity measurement with set criteria of 5% or less conductivity comparing to previous deprotection cycle. The overall synthesis yield for this series of peptides (linear) is better than 90%, determined by analytical HPLC.

The resin is air-dried and transferred into a glass vial and a freshly prepared cleavage reagent (2 ml) is added. The deprotection reaction is carried out for 2 hours at room temperature with constant stirring. The supernatant is then separated from the resin by filtration. The resin is sequentially washed with TFA (2×2 ml) and double distilled water. The combined wash solutions are extracted with ether (3×20 ml). The upper (ether) layer is discarded after each extraction. The peptide solution is freeze-dried overnight. The identity of the linear peptide is determined by both MS and HPLC. Expected peptide molecular weight is detected. Analytical HPLC profile indicates that the peptide purity is over 90%.

The peptide powder is dissolved in DMF (15 ml) and K$_2$HPO$_4$ (60 mg) is added. The reaction mixture is cooled in dry-ice and treated with DPPA (70 μl), agitated for 20 min., and warmed up to 4° C. An additional, equal portion of DPPA is added after 2 hours. The total cyclization reaction proceeds for 24 hours. DMF is then removed by vacuum. Cyclic peptide is re-dissolved in 50% acetic acid and purified by a C8 reverse phase HPLC using a linear gradient of 0–70% solvent B with solvent A in 70 min at a flow rate 3 ml/min. The composition of solvents A and B are as follows: A: 0.1% TFA, 2% acetonitrile in water; B: 0.1% TFA in 95% acetonitrile. The fractions are collected at every 0.5 min. Aliquots of each fraction are analyzed by both MS and analytical RP-HPLC. The fractions that contain a single u.v. 220 nm absorbance peak with expected mass unit for the cyclized peptide ([M+H]$^+$: 1066.2) are combined and lyophilized. The final purity (95%) of the peptide is determined by an analytical RP-HPLC of the combined fractions.

The cyclic peptides listed below are readily synthesized according to the same protocol as Example 1, but with certain modifications as noted.

EXAMPLE 2

Synthesis of Ac-[DYfRWGK]-NH$_2$, [M+H]+: 995.1

Prepared according to Example 1, with the exception that Fmoc-D-Ala is not used.

EXAMPLE 3

Synthesis of Ac-a[DyfRWGK]-NH$_2$, [M+H]+: 1066.2

Prepared according to Example 1, with the exception that Fmoc-D-Tyr-OtBu is used instead of Fmoc-L-Tyr-OtBu.

EXAMPLE 4

Synthesis of Ac-a[EYfRWG(Orn)]-NH$_2$[M+H]$^+$: 1052.1

Prepared according to Example 1, except Fmoc-L-Glu-OtBu and Fmoc-L-Orn-Boc are used instead of Fmoc-Asp-OtBu and Fmoc-Lys-Boc, respectively.

EXAMPLE 5

Synthesis of Ac-a[EYfRWGK]-NH$_2$[M+H]$^+$: 1080.2

Prepared according to Example 1, except Fmoc-L-Glu-OtBu is used instead of Fmoc-L-Asp-OtBu.

EXAMPLE 6

Synthesis of Ac-a[DYyRWGK]-NH$_2$[M+H]$^+$: 1082.2

Prepared according to Example 1, except Fmoc-D-Tyr-OtBu is used instead of Fmoc-D-Phe.

EXAMPLE 7

Synthesis of Ac-a[DY(D-Phe(pCl))RWK]-NH$_2$[M+H]$^+$: 1061.7

Prepared according to Example 1, except Fmoc-D-Phe (pCl) is used instead of Fmoc-D-Phe.

EXAMPLE 8

Synthesis of Ac-SYSa[DYfRWGK]-NH$_2$[M+H]$^+$: 1403.5

Prepared according to Example 1, except three additional amino acid (Fmoc-L-Ser-OtBu, Fmoc-L-Tyr-OtBu and Fmoc-L-Ser-OtBu) are used at the N-terminus of the peptide of Example 1.

EXAMPLE 9

Synthesis of Ac-[EYfRWGK]-NH$_2$, [M+H]+: 1009.2

Prepared according to Example 1, except Fmoc-L-Glu-OtBu is used instead of Fmoc-L-Asp-OtBu and Fmoc-D-Ala is not used.

EXAMPLE 10

Synthesis of Ac-a[DY(D-Nal)RWK]-NH$_2$, [M+H]+: 1060.2

Prepared according to Example 1, except Fmoc-D-Nal is used instead of Fmoc-D-Phe and Fmoc-L-Gly is not used.

EXAMPLE 11

Synthesis of Ac-a[DYfRWK]-NH$_2$, [M+H]+: 1009.1

Prepared according to Example 1, except Fmoc-L-Gly is not used.

EXAMPLE 12

Synthesis of Ac-GGGa[DYfRWGK]-NH$_2$, [M+H]+: 1237.3

Prepared according to Example 1, except three additional amino acid (Fmoc-L-Gly, Fmoc-L-Gly and Fmoc-L-Gly) are used at the N-terminus of the peptide of Example 1.

EXAMPLE 13

Synthesis of Ac-[DY(D-Nal)RWGK]-NH$_2$, [M+H]+: 1045.1

Prepared according to Example 1, except Fmoc-D-Nal is used instead of Fmoc-D-Phe and Fmoc-D-Ala is not used.

The linear peptides described in Examples 14–17 below are synthesized according to the same protocol as Example 1, except without the cyclization steps.

EXAMPLE 14

Synthesis of Ac-aDYfRWK-NH$_2$, [M+H]+: 1010.0

Prepared according to Example 1, except Fmoc-L-Gly is not used.

EXAMPLE 15

Synthesis of Ac-aEYfRWGK-NH$_2$, [M+H]+: 1098.2

Prepared according to Example 1, except Fmoc-L-Glu-OtBu is used instead of Fmoc-L-Asp-OtBu.

EXAMPLE 16

Synthesis of Ac-aDYfRWGK-NH$_2$, [M+H]+: 1084.2

Compound is the same as example 1 without cyclization.

EXAMPLE 17

Synthesis of Ac-aDYfRWG(Orn)-NH$_2$, [M+H]+: 1070.1

Prepared according to Example 1, except Fmoc-L-Orn-Boc is used instead of Fmoc-Lys-Boc.

EXAMPLE 18

Synthesis of [(5-Ava)YfRW(5-Ava)], [M+H]$^+$: 851.5

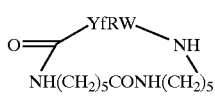

Prepared according to Example 1. The following Fmoc— protected amino acids were used: Y, f, R, W, 5-Ave; Fmoc— protected amino acids D, a, G, K were not used.

EXAMPLE 19

Synthesis of [(5-Ava)YfRW], [M+H]$^+$: 752.3

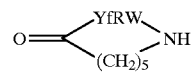

Prepared according to Example 1. The following Fmoc— protected amino acids were used: Y, f, R, W, 5-Ave; Fmoc— protected amino acids D, a, G, K were not used.

EXAMPLE 20

Synthesis of [(6-Ahx)YfRW], [M+H]$^+$: 766.3

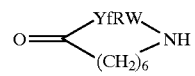

Prepared according to Example 1. The following Fmoc— protected amino acids were used: Y, f, R, W, 6-Ahx. Fmoc— protected amino acids D, a, G, K were not used.

EXAMPLE 21

Synthesis of Ac-[DYfRWG(Orn)]-NH$_2$[M+H]$^+$: 980.2

Prepared according to Example 1, except Fmoc-L-Orn-Boc is used instead of Fmoc-Lys-Boc and Fmoc-D-Ala is not used.

EXAMPLE 22

Synthesis of Ac-[DYf(homoArg)WGK]-NH$_2$[M+H]$^+$: 1008.6

Prepared according to Example 1, except Fmoc-homoArg-(Pmc) is used instead of moc-L-Arg-Pbf and Fmoc-D-Ala is not used.

EXAMPLE 23

Synthesis of [GGYfRWGGG] [M+H]$^+$: 938.5

Prepared according to Example 1, except Fmoc-D-Ala, Fmoc-Asp-OtBu, Fmoc-ys-Boc are not used, and two additional amino acids (Fmoc-Gly, Fmoc-Gly) are used at he N-terminus and C-terminus of the peptide, respectively.

EXAMPLE 24

Synthesis of Ac-[DYfHWGK]-NH$_2$[M+H]$^+$: 975.5

Prepared according to Example 1, except Fmoc-L-His-Trt is used instead of Fmoc-L-Arg-Pbf and Fmoc-D-Ala is not used

EXAMPLE 25

Synthesis of Ac-[DYfR(D-Nal)GK-NH$_2$[M+H]$^+$: 1043.4

Prepared according to Example 1, except Fmoc-D-Nal is used instead of Fmoc-L-Trp and Fmoc-D-Ala is not used.

EXAMPLE 26

Synthesis of Ac-Nle[DYfRWGK]-NH$_2$[M+H]$^+$: 1191.7

Prepared according to Example 1, except Fmoc-L-Nle is used instead of Fmoc-D-Ala.

EXAMPLE 27

Synthesis of Ac-a[DHfRWGK]-NH$_2$, [M+H]+: 1039.4

Prepared according to Example 1, except Fmoc-L-His-Trt is used instead of Fmoc-L-Tyr-OtBu.

EXAMPLE 28

Synthesis of Ac-a[D(homoTyr)fRWGK]-NH$_2$, [M+H]+: 1079.2

Prepared according to Example 1, except Fmoc-L-homoTyr-OtBu is used instead of Fmoc-L-Tyr-OtBu.

EXAMPLE 29

Synthesis of Ac-a[DFfRWGK]-NH$_2$, [M+H]+: 1049.5

Prepared according to Example 1, except Fmoc-L-Phe is used instead of Fmoc-L-Tyr-OtBu.

EXAMPLE 30

Synthesis of Ac-Nle[DHyRWK]-NH$_2$, [M+H]+: 1040.6

Prepared according to Example 1, except Fmoc-Nle is used instead of Fmoc-D-Ala, Fmoc-His-Trt is used instead of Fmoc-L-Tyr-OtBu, and Fmoc-L-Gly is not used.

EXAMPLE 31

Synthesis of Ac-a[DYfRWG(Orn)]-NH$_2$, [M+H]+: 1051.5

Prepared according to Example 1, except Fmoc-L-Orn-Boc is used instead of moc-L-Lys-Boc.

Many compounds of this invention, including those described in the specific examples above, can be made on a solid support with the aid of an automated peptide synthesizer such as PE-ABD 433. However, other structures may require methodology that cannot be easily accommodated by the synthesizer. For the latter products, the solution phase synthesis is more appropriate. The synthetic example described below illustrates application of both solid supported automated synthesis and preparation in solution.

EXAMPLE 32

Synthesis of N-{3-[9-Benzyl-12-(4-hydrxy-benzyl)-3-(1H-indol-3-ylmethyl)-2,5,8,11,14-pentaoxo-1,4,7,10,13-pentaaza-cyclopentacos-6-yl]-propyl}-guanidine (a)

Step 1:

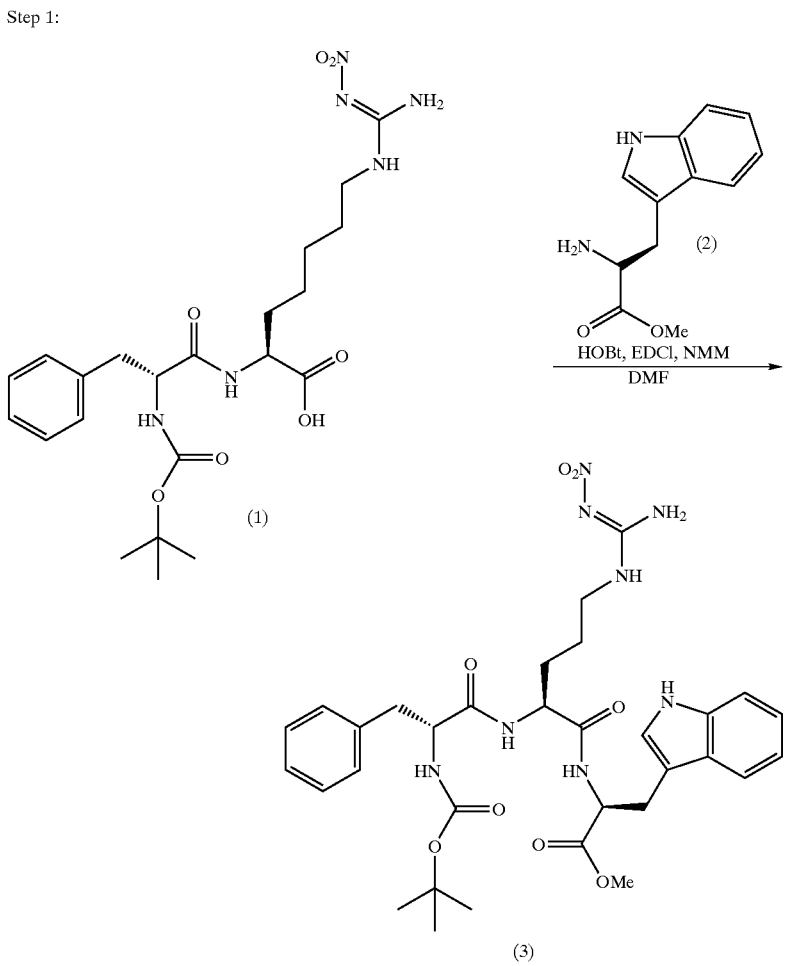

A mixture of dipeptide (1) (0.233 g, 0.5 mmol), L-tryptophan methyl ester (2) (0.127 g, 0.5 mmol), EOBt (0.135 g, 1.0 mmol), and N-methylmorpholine (0.17 ml, 1.5 mmol) in dimethylformamide (1 ml) is treated with EDCI (0.115 g, 0.6 mmol) and stirred overnight at room temperature. A treatment of the reaction mixture with water (30 ml) results in the precipitation of a crude product which is separated by decanting the liquid. The crude product is mixed again with water, filtered, washed with water and purified on a silica column with a 20:1 solution of dichloromethane and methanol as the eluant. The yield of tripeptide (3) is 0.26 g.

(b)

Step 2:

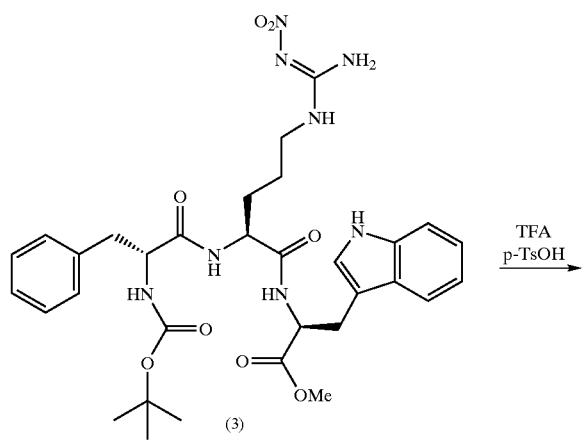

(3)

TFA
p-TsOH

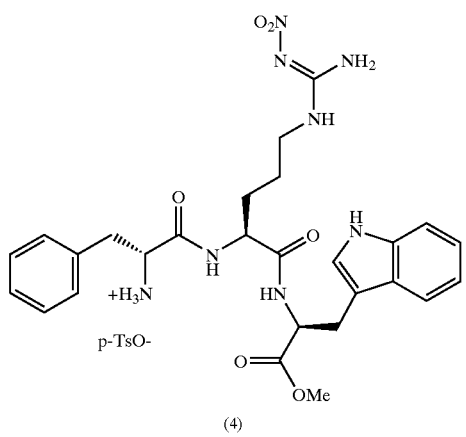

(4)

Tripeptide (3) (0.26 g) is treated with 25% (v/v) solution of trifluoroacetic acid in dichloromethane (2 ml) for 2 hr. at room temperature. The reaction mixture is diluted with 1,2-dichloroethane (10 ml), treated with p-toluenesulfonic acid hydrate (95 mg, 0.5 mmol) and evaporated under reduced pressure to give 0.34 g of the product (4).

(c)

Step 3:

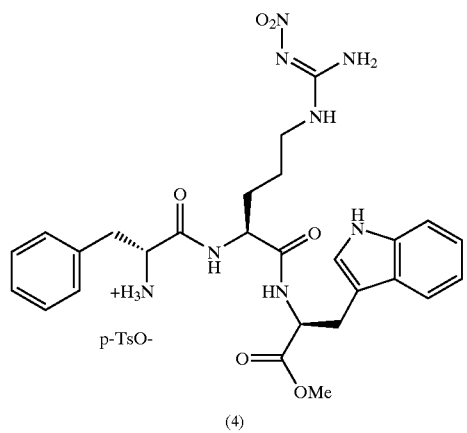

(4)

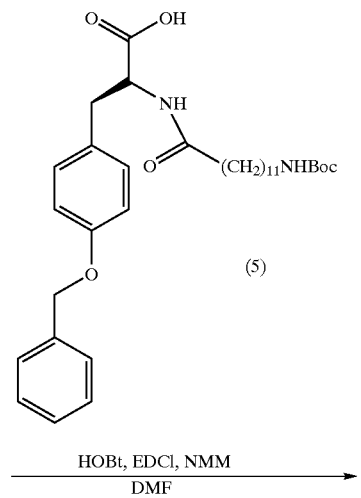

(5)

HOBt, EDCl, NMM
DMF

-continued
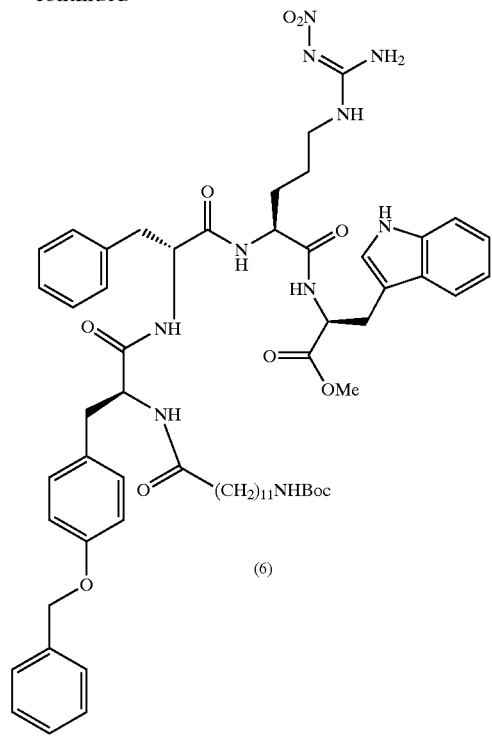
(6)
The procedure analogous to that applied for the preparation of (3) is applied for the reaction of (4) (0.344 g 0.46 mmol) with (5) (0.262 g, 0.46 mmol). The crude product is purified on a silica column using a 9:1 solution of ethyl acetate and methanol as the eluant to give 0.21 g of (6).
(d)
Step 4:
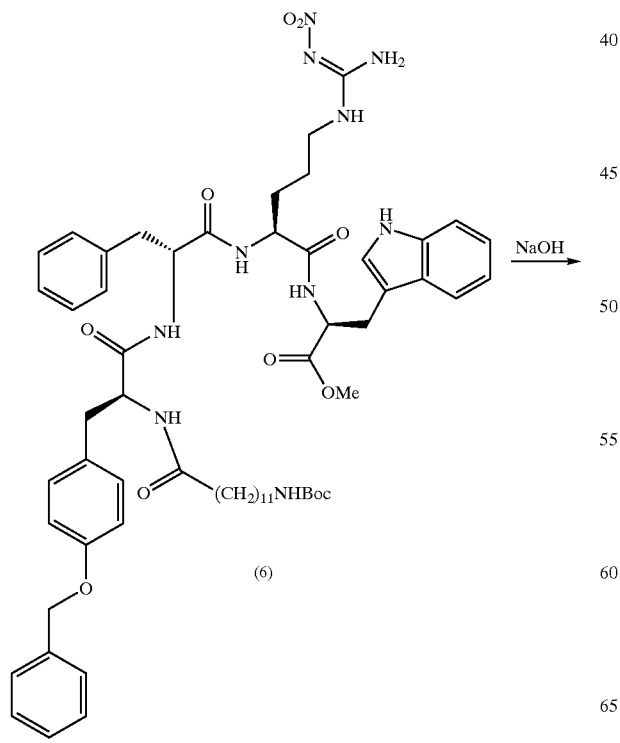
(6)
NaOH →

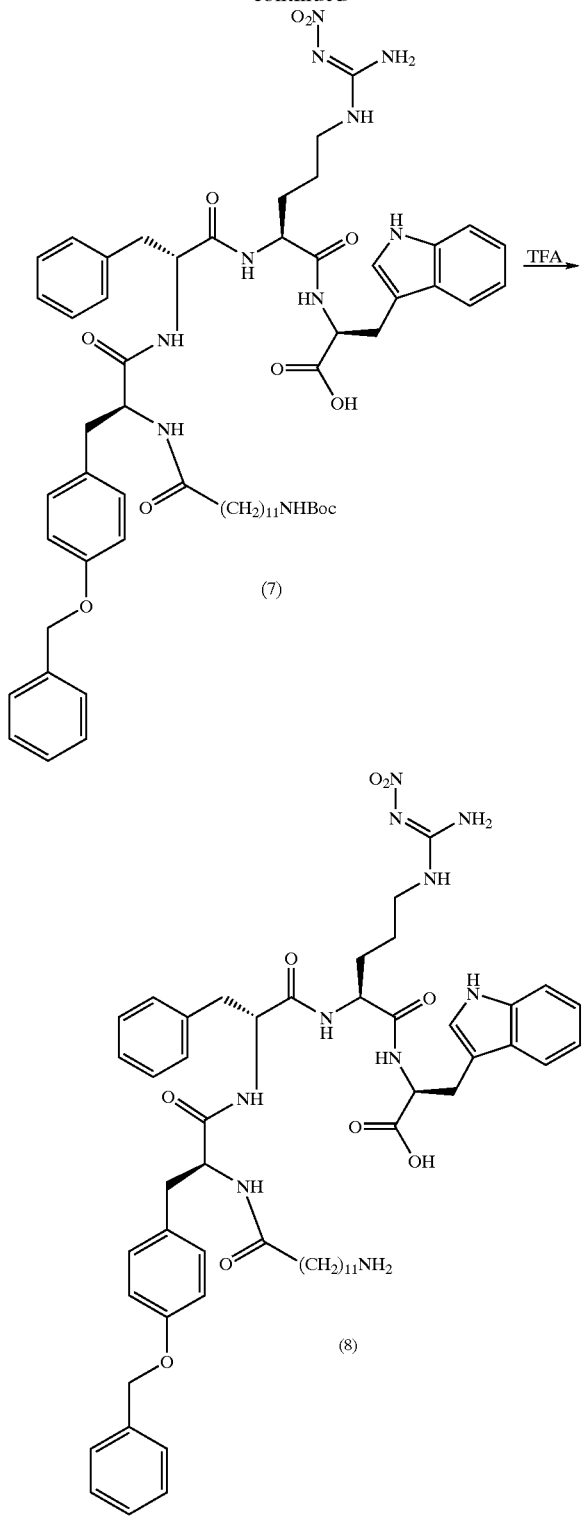

(7)

(8)

Tetrapeptide (6) (0.233 g, 0.21 mmol) in tetrahydrofuran (5 ml) is stirred with 1 N NaOH (0.5 ml) at room temperature for 3 hr. The reaction mixture is acidified with 1 N HCl to pH 2 and partitioned between water and ethyl acetate. The aqueous layer is repeatedly extracted with fresh ethyl acetate, combined organic extracts are washed with 0.1 N HCl, dried with anhydrous magnesium sulfate and filtered. Concentration under reduced pressure produced 0.226 g of the product (7).

The crude residue of (7) is stirred with 25% (v/v) solution of trifluoroacetic acid in dichloromethane (2 ml) for 2 hr. at room temperature. The reaction mixture is diluted with 1,2-dichloroethane (10 ml) and evaporated under reduced pressure. The residue is purified on HPLC C4 reverse phase column using a linear gradient of 0.1% aqueous trifluoroacetic acid and acetonitrile to give 0.155 g of (8).

(e)

Step 5:

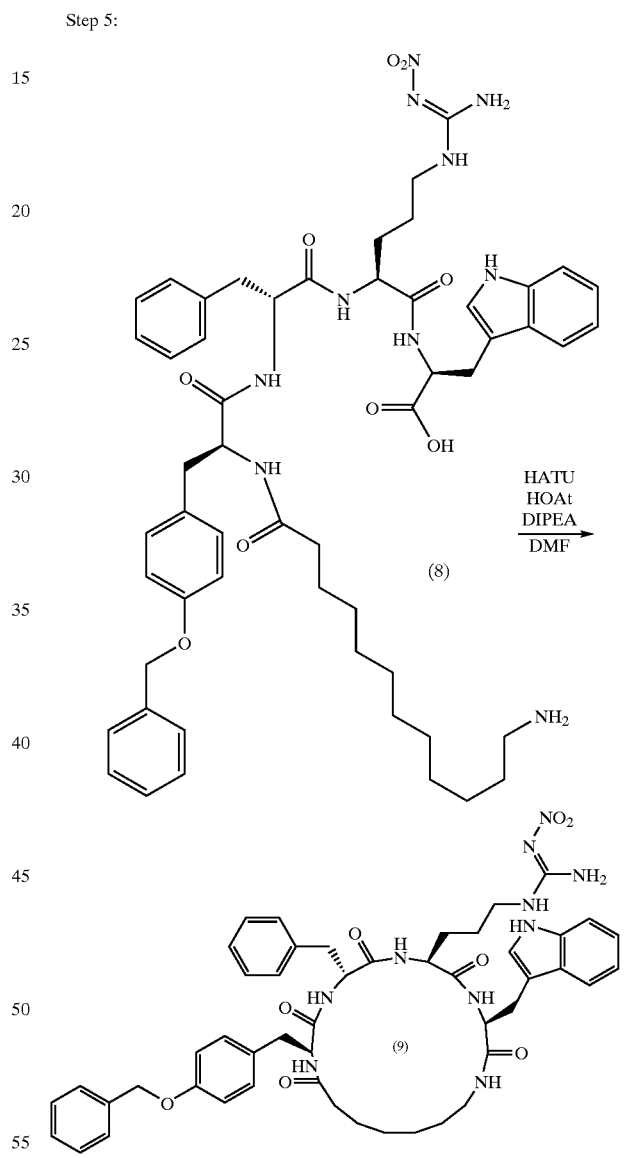

(8)

(9)

Tetrapeptide (8) (100 mg, 0.1 mmol), HATU (46 mg, 0.12 mmol) and HOAt (14 mg, 0.1 mmol) are placed in a dry flask under argon atmosphere. Dimethylformamide (100 ml) is added and the flask is cooled to about 0° C. in an ice bath. DIPEA (0.053 ml, 0.3 mmol) is added and the reaction mixture is stirred in the ice bath for 3 hr. After solvent evaporation under reduced pressure, the crude material is separated on a silica column using a 15:1 solution of dichloromethane and methanol as the eluant to give 90 mg of the macrocyclic product (9).

Step 6:

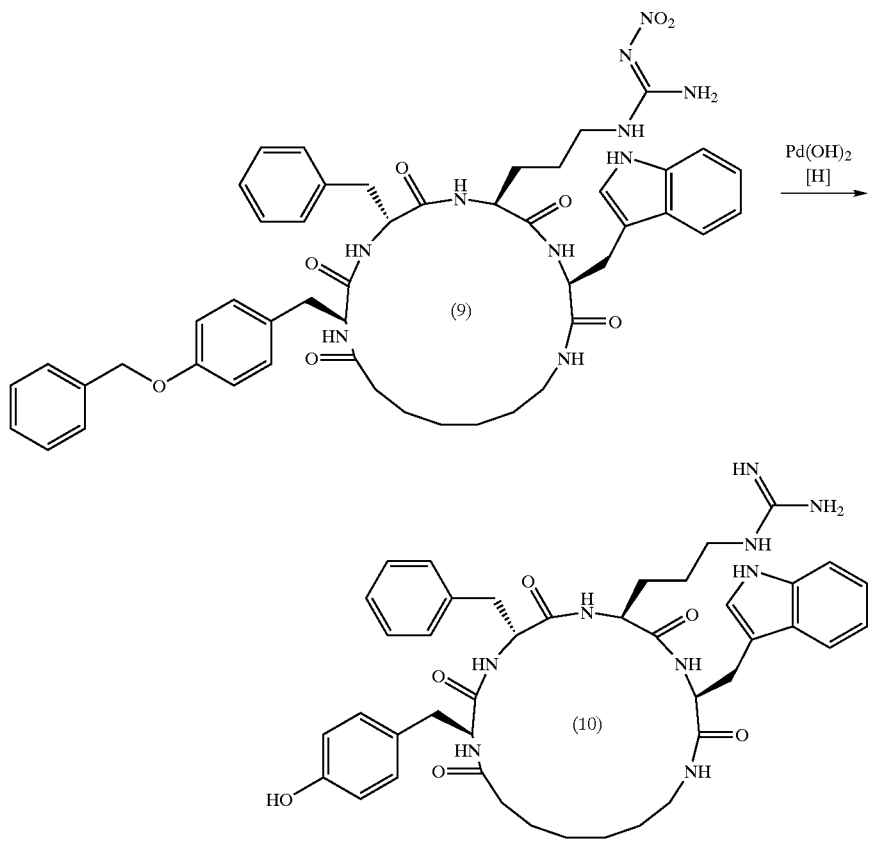

The macrocylic compound (9) (0.09 g) is hydrogenated in ethanol (20 ml) with 20% Pd(OH)$_2$ at 45 psi. for 48 hr. The catalyst is removed by filtration through Celite. After evaporation of the filtrate, the crude product is purified on HPLC using a C4 reverse phase column and a linear gradient of 0.1% aqueous trifluoroacetic acid and acetonitrile to give final product N-{3-[9-Benzyl-12-(4-hydroxy-benzyl)-3-(1H-indol-3-ylmethyl)-2,5,8,11,14-pentaoxo-1,4,7,10,13-pentaaza-cyclopentacos-6-yl]-propyl}-guanidine (10).

EXAMPLE 33

Synthesis of 12-Benzoylamino-9-benzyl-6-(3-guanidinopropyl)-5,8,11-trioxo-1,14-dioxa-4,7,10-triaza-cyclooctadecane-3-carboxylic Acid Naphthalen-1-ylamide Step 1:

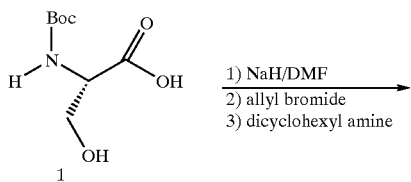

-continued

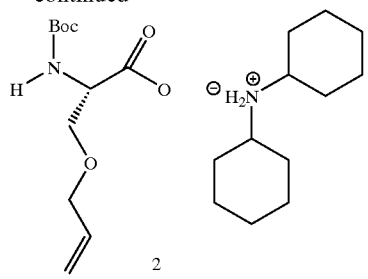

A solution of Boc-Ser-OH (1, 2.05 g, 10 mmol) in DMF (30 ml) is added to a stirred suspension of sodium hydride (60 wt % in mineral oil, 880 mg, 22 mmol) in DMF (30 ml) at 0° C. After the evolution of hydrogen gas ceased, allyl bromide (0.95 ml, 11 mmol) is added to the milk-colored solution. The resulting mixture is stirred at room temperature for 5 h to give a clear solution. The solvent is removed in vacuo, water (50 ml) is added, and the aqueous solution is extracted with ether (2×20 ml.) The aqueous solution is then acidified to pH 3.0 with 1.0 N HCl and extracted further with ethyl acetate (5×20 ml.) The combined ethyl acetate extracts are washed with water (20 ml), brine (20 ml), dried over anhydrous magnesium sulfate, and concentrated to give crude Boc-Ser(allyl)-OH (1.96 g) as a light yellow oil. A solution of this oil in ether (30 ml) is treated with dicyclohexylamine (1.594 ml, 8.0 mmol), the solvent removed, and the residue triturated with 1:9 ethyl acetate/hexane to yield 2 (2.26 g) as a colorless solid. An additional amount of 2 (0.58 g) is isolated from the trituration solution also as a colorless solid.

Step 2:

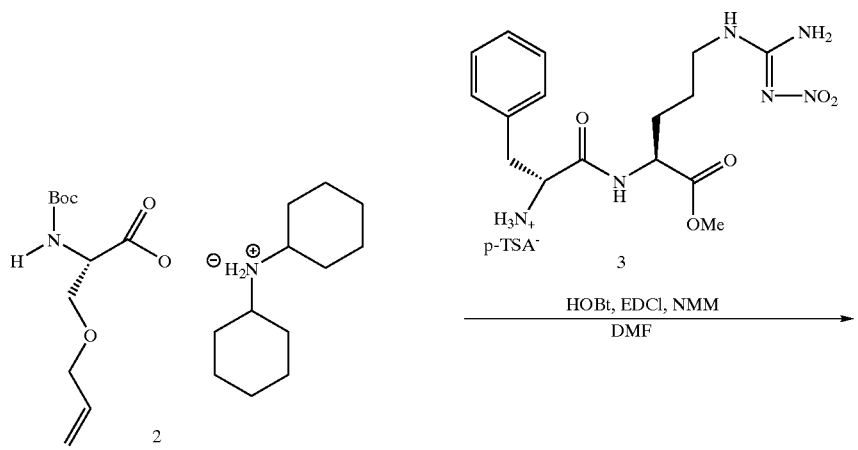

A mixture of dipeptide (3, 1.382 g, 2.5 mmol), Boc-Ser(allyl)-OH.DCA salt (2, 1.067 g, 2.5 mmol), HOBt (0.338 g, 2.5 mmol), and N-methylmorpholine (0.6 ml, 5.5 mmol) in DMF (40 ml) is treated with EDCI (0.527 g, 2.75 mmol) and stirred at room temperature 16 h. The reaction mixture is diluted with ethyl acetate (300 ml) and washed successively with water (50 ml), 5% aqueous citric acid (2×25 ml), 5% aqueous sodium bicarbonate (2×25 ml), and brine (25 ml.) The ethyl acetate solution is dried over a combination of anhydrous sodium and magnesium sulfates and is concentrated to yield 4 (1.519 g) as a colorless syrup.

Step 3:

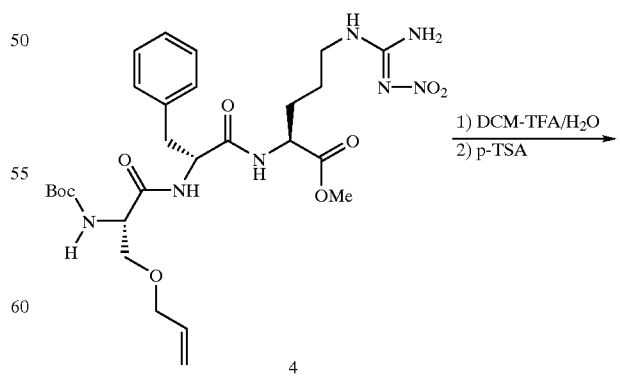

-continued

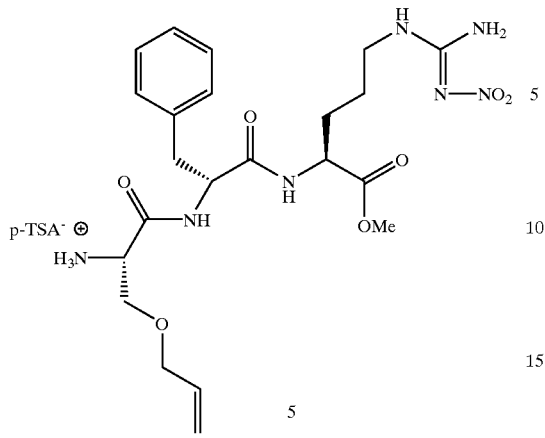

5

Trifluoroacetic acid (6.0 ml) is added at room temperature to a well-stirred mixture of Boc-Ser(allyl)-D-Phe-Arg(NO₂)-OMe (4, 1.519 g, 2.5 mmol), dichloromethane (30 ml) and water (0.6 ml.) After stirring at room temperature for 3 h, p-toluenesulfonic acid hydrate (0.380 g, 2.00 mmol) is added and the volatiles are removed in vacuo. Trituration of the residue with ether (50 ml) afforded 5 (1.46 g) as an off-white solid.

(d)

Step 4:

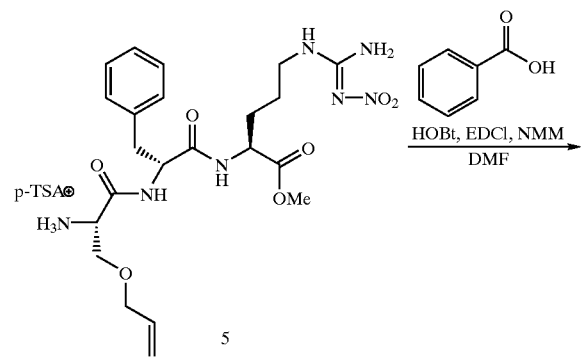

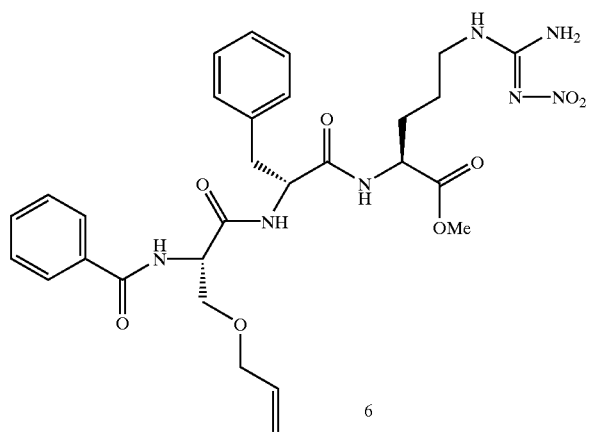

6

A mixture of tripeptide (5, 1.46 g, 2.15 mmol), benzoic acid (0.263 g, 2.15 mmol), HOBt (0.291 g, 2.15 mmol), and N-methylmorpholine (0.52 ml, 4.7 mmol) in DMF (22 ml) is treated with EDCI (0.454 g, 2.37 mmol) and stirred at room temperature 16 h. The reaction mixture is diluted with ethyl acetate (220 ml) and washed successively with water (50 ml), 1 N HCl (2×25 ml), 1 N aqueous sodium bicarbonate (2×25 ml), and brine (25 ml.) The ethyl acetate solution is dried over a combination of anhydrous sodium and magnesium sulfates and is concentrated to yield 6 (1.10 g) as a colorless solid.

(e)

Step 5:

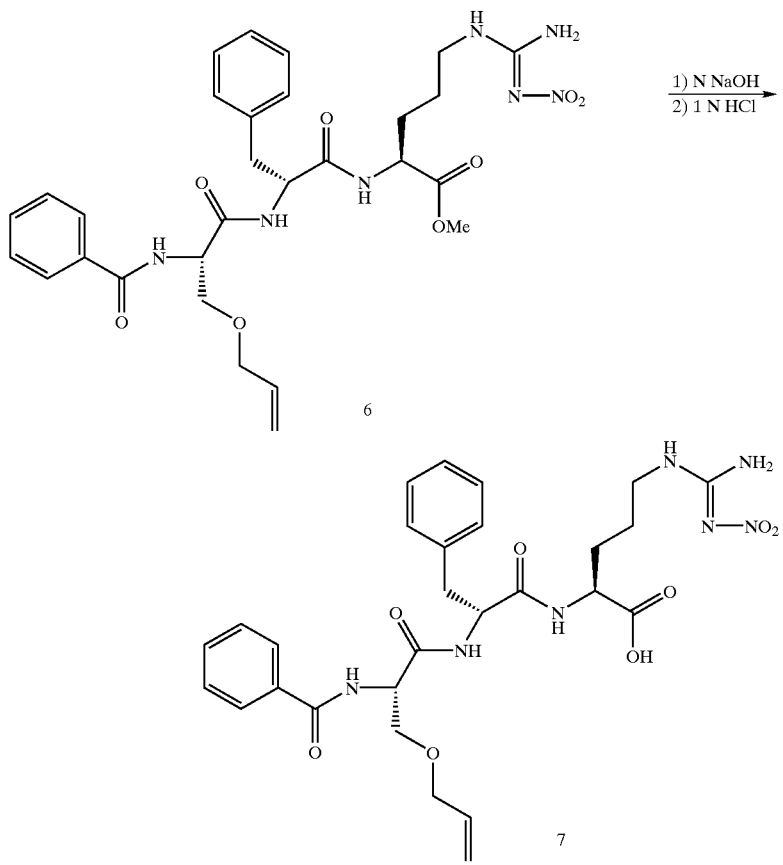

Aqueous sodium hydroxide (1.0 N. 3.0 ml, 3.0 mmol) is added to a well-stirred solution of the benzoyl-tripeptide ester (6, 1.10 g, 1.80 mmol) in methanol (18 ml) at room temperature. The resulting mixture is stirred at room temperature for 2.5 h and the volatiles are removed by rotary evaporation. The residue is dissolved in water (20 ml), the solution acidified to pH 3 with 1 N HCl (3.2–3.5 ml), and the solution extracted with ethyl acetate (1×70 ml, 2×25 ml.) The combined ethyl acetate extracts are dried over anhydrous sodium sulfate and concentrated in vacuo. Trituration of the residue with ether gives 7 (0.884 g) as a colorless solid.

Step 6:

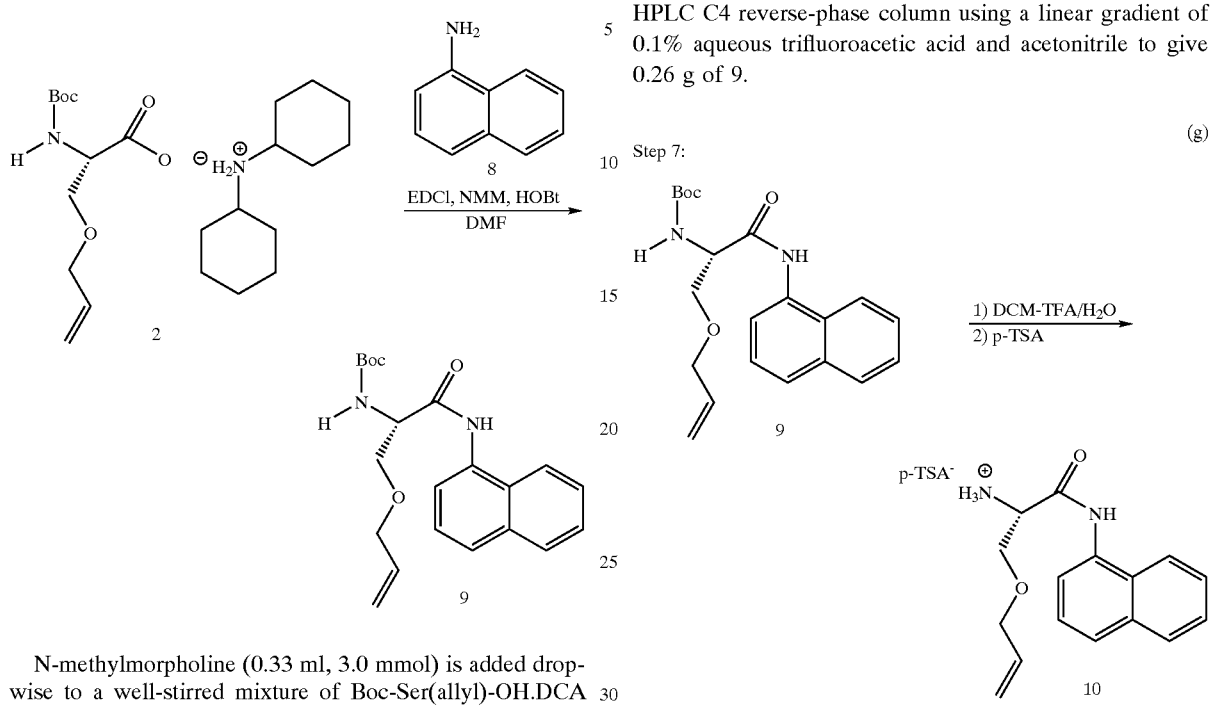

N-methylmorpholine (0.33 ml, 3.0 mmol) is added dropwise to a well-stirred mixture of Boc-Ser(allyl)-OH.DCA salt (2, 1.067 g, 2.5 mmol), ]-naphthylamine (8, 0.358 g, 2.5 mmol), HOBt (0.338 g, 2.5 mmol), and EDCI (0.527 g, 2.75 mmol) in DMF (28 ml) at 0° C. The resulting mixture is stirred at 0° C. for 0.5 h and then at room temperature for 16 h. The reaction mixture is then diluted with ethyl acetate (200 ml) and washed successively with water (50 ml), 1 N HCl (2×25 ml), 1 N aqueous sodium bicarbonate (2×25 ml), and brine (20 ml.) The ethyl acetate solution is dried over anhydrous sodium sulfate and is concentrated to a brown oil which is shown by HPLC/MS analysis to consist of a mixture of 8 and 9. This crude product is purified on an HPLC C4 reverse-phase column using a linear gradient of 0.1% aqueous trifluoroacetic acid and acetonitrile to give 0.26 g of 9.

Step 7:

Trifluoroacetic acid (1.0 ml) is added at room temperature to a well-stirred mixture of Boc-Ser(allyl)-1-naphthamide (9, 0.26 g, 0.702 mmol), dichloromethane (5.0 ml), and water (0.1 ml.) After stirring at room temperature for 88 h, p-toluenesulfonic acid hydrate (0.133 g, 0.7 mmol) is added and the volatiles are removed in vacuo. Trituration of the residue with ether/hexane (1:1, 25 ml) afforded 10 (0.311 g) as a brown solid.

Step 8:

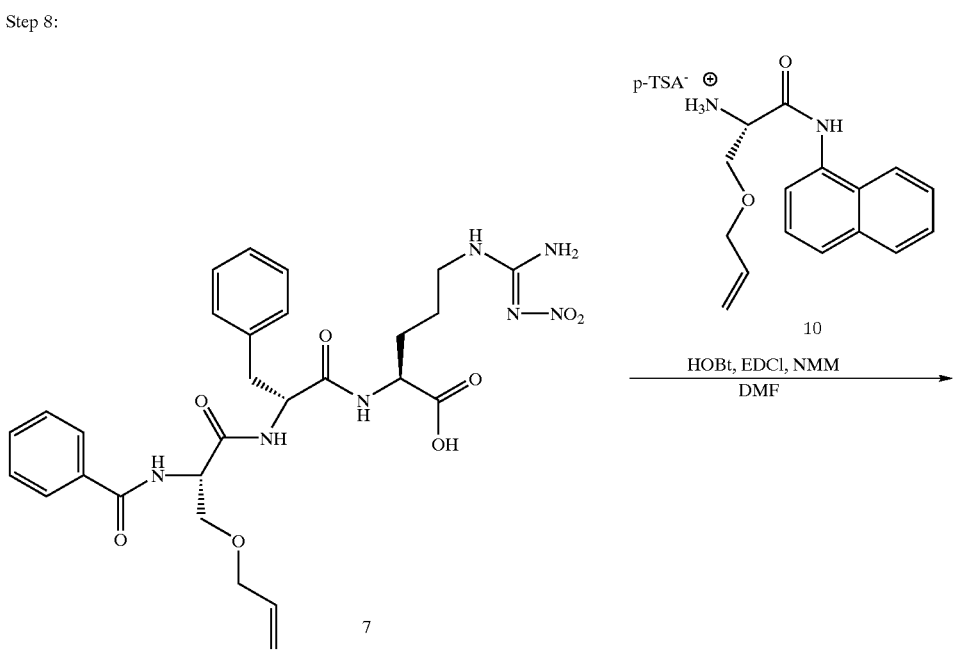

-continued

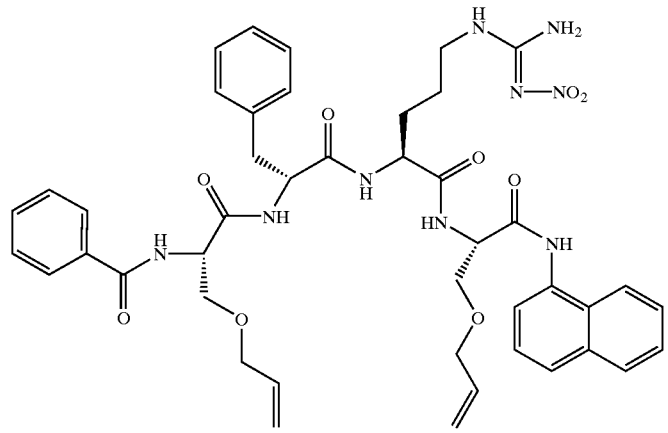

11

N-methylmorpholine (0.18 ml, 1.61 mmol) is added dropwise to a well-stirred mixture of the benzoyl-tripeptide acid (7, 0.436 g, 0.73 mmol), the p-TSA salt of H-Ser(allyl)-1-naphthamide (10, 0.322 g, 0.73 mmol), HOBt (0.099 g, 0.73 mmol), and EDCI (0. 154 g, 0.803 mmol) in DMF (6 ml) at 0° C. The resulting mixture is stirred at 0° C. for 0.5 h and then at room temperature for 16 h. The reaction mixture is then diluted with ethyl acetate (100 ml) and washed successively with water (15 ml), 1 N HCl (2×10 ml), water (15 ml), 1 N aqueous sodium bicarbonate (2×10 ml), and brine (2×10 ml.) The ethyl acetate solution is dried over a combination of anhydrous sodium and magnesium sulfates, is concentrated in vacuo, and then the residue triturated with ether (50 ml) to yield 11 (0.531 g) as a light brown solid.

(i)

Step 9:

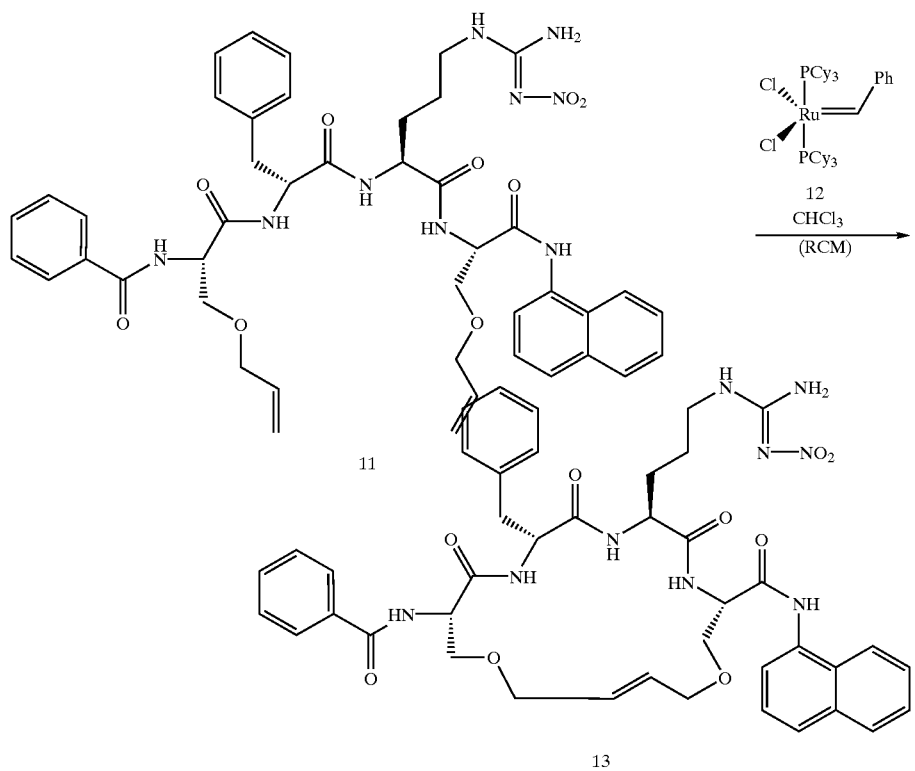

A degassed solution of Grubb's catalyst (12, 0.0504 g, 0.061 mmol) in chloroform (5.0 ml) is added to a well-stirred and degassed solution of the diene (11, 0.260 g, 0.306 mmol) in chloroform (20 ml) at room temperature. The resulting purple solution is stirred at room temperature under argon for 22 h. More catalyst (0.0504 g) in chloroform (5.0 ml) is added, the mixture is stirred at room temperature for 5 h, and more catalyst (0.0504 g) in chloroform (5.0 ml) is again added. After stirring 60 h at room temperature, triethylamine (3.0 ml) is added and the solution is concentrated by rotary evaporation. The residue is chromatographed on silica gel using ethyl acetate and 1:9 ethyl acetate/methanol as eluants to afford a crude product (0.125 g) which is purified further on an HPLC C4 reverse-phase column using a linear gradient of 0.1% aqueous trifluoracetic acid and acetonitrile to yield 13 (8 mg) as a 1:1 mixture of E and Z isomers.

Step 10:

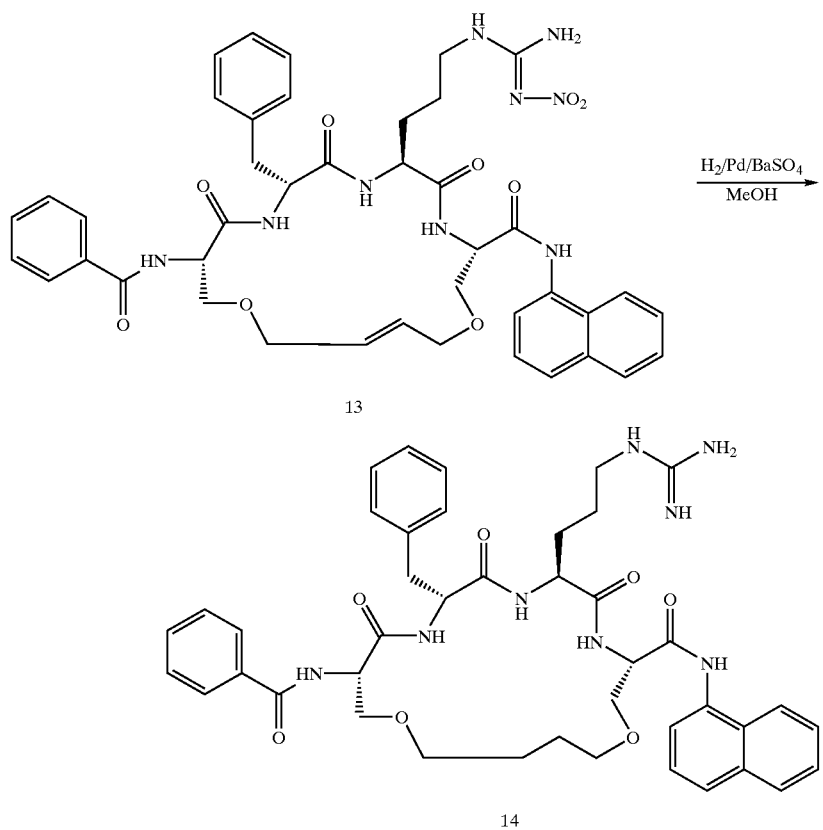

A solution of the macrocycle (13, 8 mg, 0.097 mmol) in methanol (10 ml) is treated with 10% palladium on barium sulfate (unreduced, 1 mg) and shaken under a hydrogen atmosphere (40 psi) for 48 h. The catalyst is removed by filtration through Celite and the solvent is removed in vacuo to give 14 as a colorless glass. Treatment of this glass in methanol with trifluoroacetic acid followed by removal of the volatiles and lyophilization of the residue from a 5% acetonitrile/water mixture gives the TFA salt of 14 (8 mg) as an off-white powder.

B. Composition and Method Examples

EXAMPLE A

An obese human female subject weighing 130 kg is treated by this method to incur weight loss. Specifically, once each day for a period of 6 months, the subject is administered, via intravenous injection, 15 ml of an aqueous solution comprising the following:

| Component | Concentration (mg/ml) |
| --- | --- |
| Compound of Ex. 1 | 5 |
| Sodium bisulfate | 1 |
| Sodium chloride | 7 |
| Chlorobutanol | 5 |
| Citric acid | 10 |

(j)

-continued

| Component | Concentration (mg/ml) |
| --- | --- |
| Sterile water | qs to 1 mL |
| Sodium Hydroxide | adjust to pH 5 |

At the end of the treatment period, the patient exhibits measurable weight loss.

EXAMPLE B

An obese human male subject weighing 150 kg is subjected to a weight-reduction program that achieves weight loss with reduced adiposity through a combination of a restricted diet and increased exercise. Specifically, once each day for a period of 6 months after weight loss, the subject is administered, via intravenous injection, 15 ml of an aqueous solution comprising the following:

| Component | Concentration (mg/ml) |
|---|---|
| Compound of Ex. 1 | 5 |
| Sodium bisulfate | 1 |
| Sodium chloride | 7 |
| Chlorobutanol | 5 |
| Citric acid | 10 |
| Sterile water | qs to 1 mL |
| Sodium Hydroxide | adjust to pH 5 |

At the end of the treatment period, the patient exhibits a maintenance of weight loss and reduced adiposity.

wherein B is a bridge moiety selected from:

i)

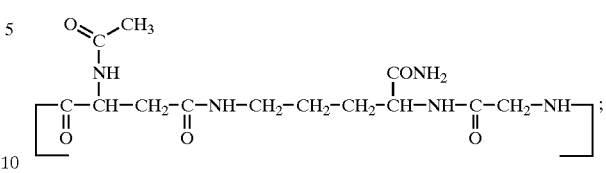

ii)

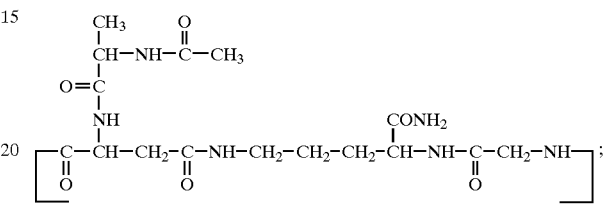

What is claimed is:

1. A cyclic peptide having the formula:

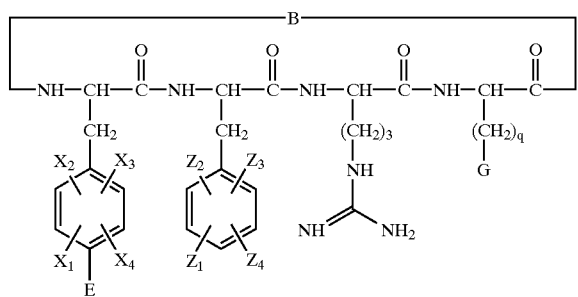

iii)

-continued

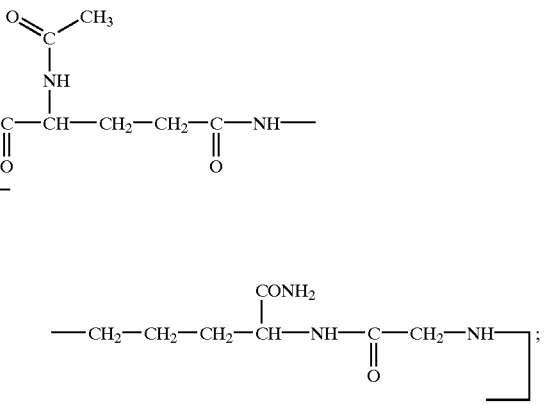

iv)

v)

vi)

vii)

viii)

E is selected from the group consisting of hydrogen; halo; —$OR^{13}$; —$SR^{13}$; —$NR^{13}R^{13'}$; —$N(R^{13})SO_2R^{13''}$; —$SO_2R^{13''}$; —$SO_2$—$NR^{13}R^{13'}$; and —$(CH_2)_rP(O)(OH)R^{15}$; r is 0 to 10; $R^{15}$ is selected from the group consisting of —OH, hydrogen; alkyl; alkenyl; alkynyl; cyano; nitro; $CF_3$; aryl; heteroaryl; cycloalkyl; and heterocycloalkyl; provided that when each X is hydrogen, E is not hydrogen; each $R^{13}$ and $R^{13'}$ is independently selected from the group consisting of hydrogen, alkyl, acyl, heteroalkyl, aryl, heteroaryl, cycloalkyl, and heterocycloalkyl; and $R^{13''}$ is selected from the group consistinig of hydrogen, alkyl, heteroalkyl, aryl, heteroaryl, cycloalkyl, and heterocycloalkyl; $X_1$, $X^2$, $X_3$, and $X_4$ which each represents the four substituents on the phenyl ring other than E, is independently selected from hydrogen; halo; $OR^8$; —$SR^8$; —$NR^8R^{8'}$; —$N(R^8)SO_2R^{8''}$; —$SO_2R^{8''}$; —$SO_2$—$NR^8R^{8'}$; and —$(CH_2)_rP(O)(OH)R^{14}$ r is 0 to 10 and $R^{14}$ is selected from the group consisting of —OH, hydrogen and alkyl; alkenyl; alklynyl; cyano; nitro, $CF_3$; aryl, heteroaryl; cycloalkyl; and heterocycloalkyl; each $R^8$ and $R^{8'}$ is independently selected from the group consisting of hydrogen, alkyl, acyl, heteroalkyl, aryl, heteroaryl, cycloalkyl, and heterocycloalkyl and $R^{8''}$ is selected from the group consisting of hydrogen, alkyl, heteroalkyl, aryl, heteroaryl, cycloalkyl, and heterocycloalkyl;

$Z_1$, $Z_2$, $Z_3$, and $Z_4$ is one or more substituents independently selected from the group consisting of hydrogen, hydroxy, halo, thiol, —O—$R^9$, —$SR^9$, —$NR^9R^{9'}$, alkyl, acyl, alkenyl, alkynyl, cyano, nitro, aryl, heteroaryl, cycloalkyl, and heterocycloalkyl; each $R^9$ and $R^{9'}$ is independently selected from hydrogen, alkyl, acyl, heteroalkyl, aryl, heteroaryl, cycloalkyl, and heterocycloalkyl;

G is selected from a substituted or unsubstituted aryl or heteroaryl ring, the index q is from 1 to 3.

2. A compound according to claim 1 having the following stereochemical formula:

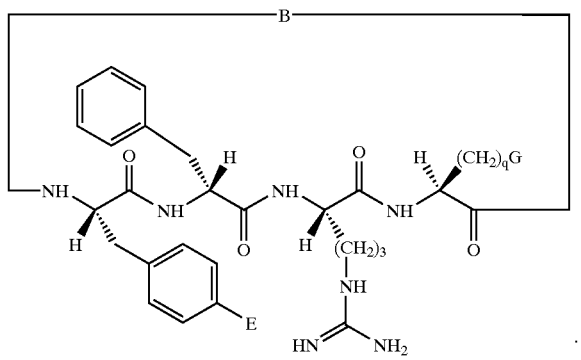

3. A compound according to claim 2 wherein B is a unit having the following stereochemical formula:

i)

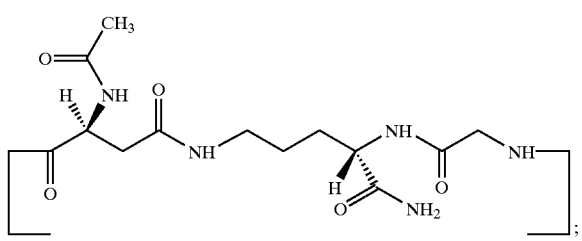

ii)

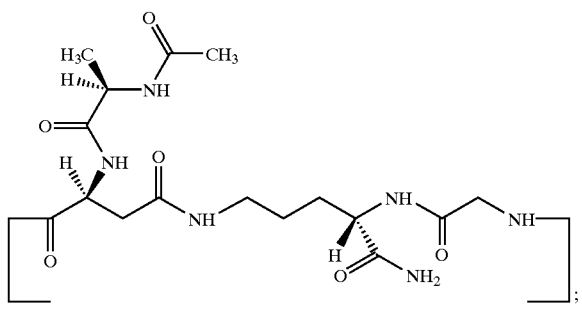

iii)

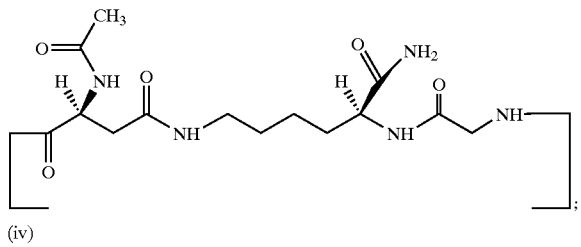

iv)

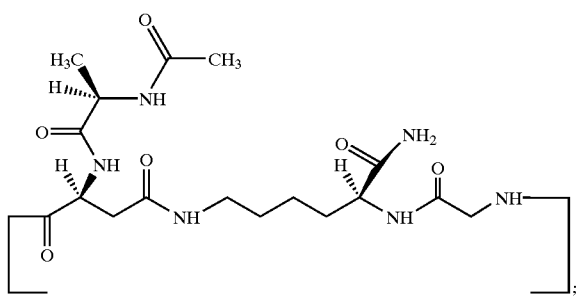

v)

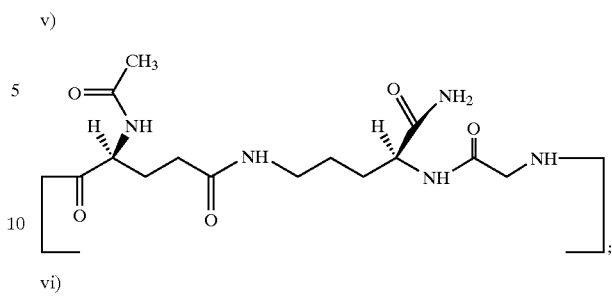

vi)

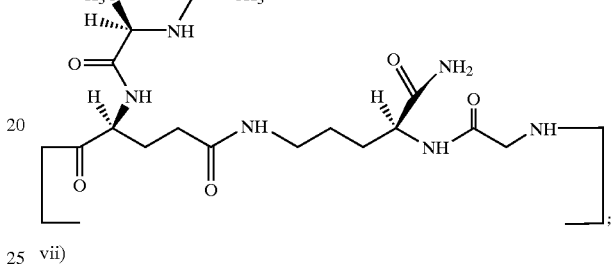

vii)

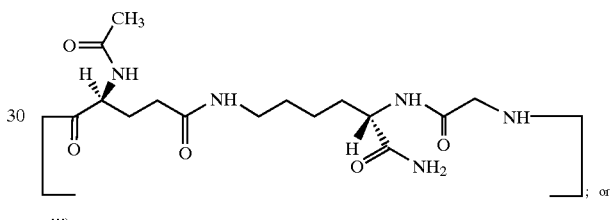

; or viii)

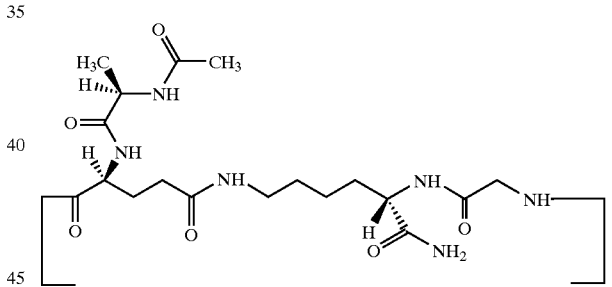

.

4. A compound according to claim 1 wherein E and $X_1$, $X_2$, $X_3$, and $X_4$ are taken together to form an aryl unit selected from the group consisting of 3-hydroxyphenyl, 4-hydroxyphenyl, 2.5-dihydroxyphenyl, 3-aminophenyl, 4-fluorophenyl, 4-chlorophenyl, 4-iodophenyl, 4-methylphenyl, 2-bromophenyl, 3-iodophenyl, 3-nitrophenyl, 4-nitrophenyl, and 3-methoxyphenyl.

5. A compound according to claim 1 wherein $Z_1$, $Z_2$, $Z_3$, and $Z_4$ have the value such that an aryl unit is formed selected from the group consisting of phenyl, 3-hydroxyphenyl, 4-hydroxyphenyl, 2,5-dihydroxyphenyl, 3-aminophenyl, 4-fluorophenyl, 4-chlorophenyl, 4-iodophenyl, 4-methylphenyl, 2-bromophenyl, 3-iodophenyl, 3-nitrophenyl, 4-nitrophenyl, and 3-methoxyphenyl.

6. A compound according to claim 1 wherein E is hydrogen, halogen, —$NO_2$, —$NR^8R^{8'}$, or —$OR^{13}$; $R^8$ and $R^{8'}$ are each independently hydrogen or methyl; $R^{13}$ is hydrogen or methyl; $X_1$, $X_2$, $X_3$, and $X_4$ represent phenyl ring substituents, said substituents each independently selected from hydrogen, halogen, —$NO_2$, or —$OR^8$; each $R^8$ is hydrogen or methyl; $Z_1$, $Z_2$, $Z_3$, and $Z_4$ represent phenyl ring substituents, said substituents independently selected from hydrogen, halogen, —$OR^9$; $R^9$ is hydrogen or methyl; G is selected from a substituted or unsubstituted aryl or heteroaryl ring, the index q is from 1 to 3.

7. A compound according to claim 1 wherein G has the formula:

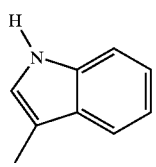

wherein the index q is equal to 3.

8. A compound according to claim 1 having the formula:

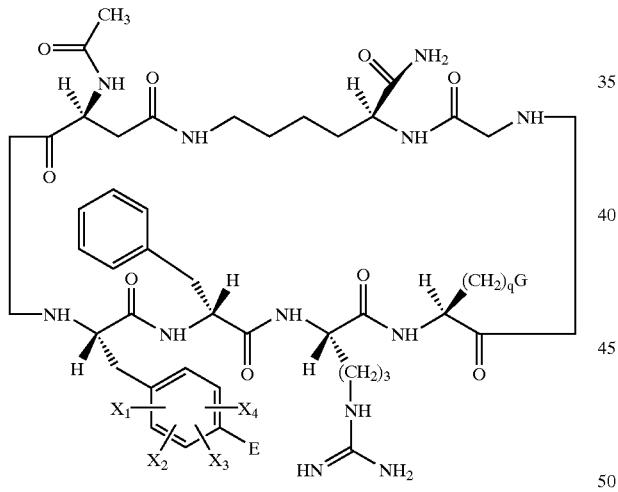

wherein E and $X_1$, $X_2$, $X_3$, and $X_4$ are taken together to form an aryl unit selected from the group consisting of phenyl, 3-hydroxyphenyl, 4-hydroxyphenyl, 2.5-dihydroxyphenyl, 3-aminophenyl, 4-fluorophenyl, 4-chlorophenyl, 4-iodophenyl, 4-methylphenyl, 2-bromophenyl, 3-iodophenyl, 3-nitrophenyl, 4-nitrophenyl, and 3-methoxyphenyl; and Z has the value such that an aryl unit is formed selected from the group consisting of phenyl, 3-hydroxyphenyl, 4-hydroxyphenyl, 2,5-dihydroxyphenyl, 3-aminophenyl, 4-fluorophenyl, 4-chlorophenyl, 4-iodophenyl, 4-methylphenyl, 2-bromophenyl, 3-iodophenyl, 3-nitrophenyl, 4-nitrophenyl, and 3-methoxyphenyl.

9. A compound according to claim 8 having the formula:

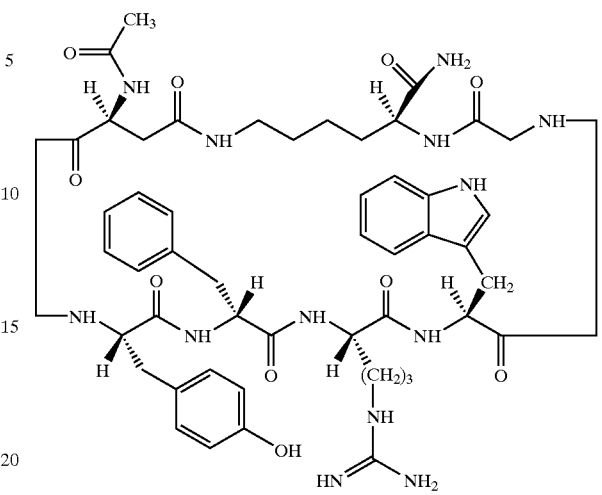

10. A cyclic peptide having the formula:

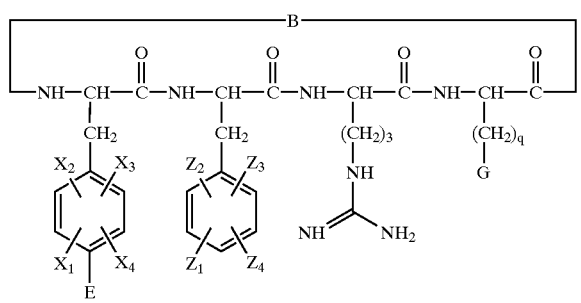

wherein B is a bridge moiety selected from:

i)
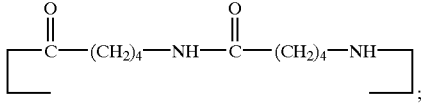

ii)
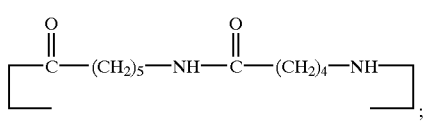

iii)
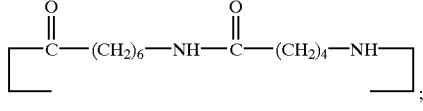

iv)
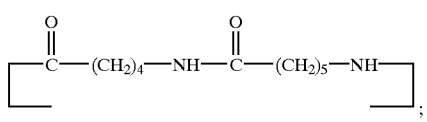

-continued v)
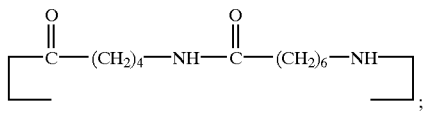

vi)
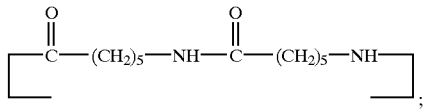

vii)
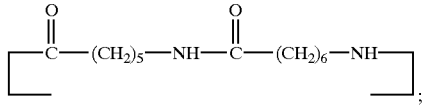

viii)
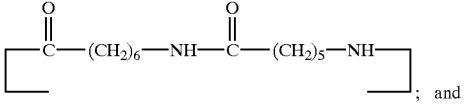

ix)
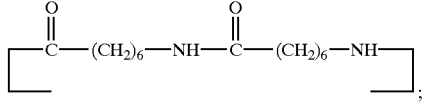

E is selected from hydrogen; halo; —OR$^{13}$; —SR$^{13}$; —NR$^{13}$R$^{13'}$; —N(R$^{13}$)SO$_2$R$^{13''}$; —SO$_2$R$^{13''}$; —SO$_2$—NR$^{13}$R$^{13'}$; —(CH$_2$)$_r$P(O)(OH)R$^{15}$; r is 0 to 10 and R$^{15}$ is selected from the group consisting of —OH, hydrogen; alkyl; alkenyl; alkynyl; cyano; nitro; CF$_3$; aryl; heteroaryl; cycloalkyl; and heterocycloalkyl; provided that when each X is hydrogen, E is not hydrogen; where each R$^{13}$ and R$^{13'}$ is independently selected from the group consisting of hydrogen, alkyl, acyl, heteroalkyl, aryl heteroaryl, cycloalkyl, and heterocycloalkyl and R$^{13''}$ is selected from the group consisting of hydrogen, alkyl, heteroalkyl, aryl, heteroaryl, cycloalkyl, and heterocycloalkyl;

X$_1$, X$_2$, X$_3$, and X$_4$ which represents the four substituents on the phenyl ring other than E and —(CH$_2$)—$_m$, is independently selected from hydrogen; halo; OR$^8$; —SR$^8$; —NR$^8$ R$^{8'}$; —N(R$^8$)SO$_2$R$^{8''}$; —SO$_2$R$^{8''}$; —SO$_2$—NR$^8$R$^{8'}$; —(CH$_2$)$_r$P(O)(OH)R$^{14}$; r is 0 to 10:R$^{14}$ is selected from the group consisting of —OH, hydrogen and alkyl; alkyl; alkene; alkyne; cyano; nitro; CF$_3$; aryl; heteroaryl; cycloalkyl; and heterocycloalkyl; each R$^8$ and R$^{8'}$ is independently selected from the group consisting of hydrogen, alkyl, acyl, heteroalkyh, aryl, heteroaryl, cycloalkyl, and heterocycloalkyl; R$^{8''}$ is selected from the group consisting of hydrogen, alkyl, heteroalkylh aryl, heteroaryl, cycloalkyl, and heterocycloalkyl;

each of Z$_1$, Z$_2$, Z$_3$, and Z$_4$ is one or more substituents independently selected from the group consisting of hydrogen, hydroxy, halo, thiol, —OR$^9$, —SR$^9$, —NR$^9$R$^{9'}$, alkyl, acyl, alkenyl, alkynyl, cyano, nitro, aryl, heteroaryl, cycloalkyh, and hetelocycloalkyl; each R$^9$ and R$^{9'}$ is independently selected from the group consisting of hydrogen, alkyl, acyl, heteroalkyl, aryl, heteroaryl, cycloalkyl, and heterocycloalkyl; and the amino acid formed by the aryl unit to which Z$_1$, Z$_2$, Z$_3$, and Z$_4$ are bonded is an amino acid in the D-configuration; G is selected from a substituted or unsubstituted aryl or heteroaryl ring, the index q is from 1 to 3.

11. A cyclic peptide analog selected from the group consisting of:

N-{3-[9-Benzyl-12-(4-hydroxy-benzyl)-3-(1H-indol-3-ylmethyl)-2,5,8,11-tetraoxo-1-oxa-4,7,10-triaza-cyclononadec-6-yl]-propyl}-guanidine;

N-{3-[9-Benzyl-12-(4-hydroxy-benzyl)-3-(1H-indol-3-ylmethyl)-2,5,8,11-tetraoxo-1-4,7,10-triaza-cyclohexadec-6-yl]-propyl}-guanidine;

N-{3-[2-Benzyl-24-(4-hydroxy-benzyl)-8-(1H-indol-3-ylmethyl)-10-methyl-3,6,11,25-tetraoxo-1,4,7,10-tetraaza-cyclopentacos-5-yl]-propyl}-guanidine;

N-{3-[2-Benzyl-24-(4-hydroxy-benzyl)-10-methyl-8-naphthalen-1-ylmethyl-3,6,11,25-tetraoxo-1,4,7,10-tetraaza-cyclopentacos-5-yl]-propyl}-guanidine;

N-{3-[2-Benzyl-24-(4-hydroxy-benzyl)-10-methyl-8-naphthalen-2-ylmethyl-3,6,11,25-tetraoxo-1,4,7,10-tetraaza-cyclopentacos-5-yl]-propyl}-guanidine;

N-{3-[9-Benzyl-12-(4-hydroxy-benzyl)-3-naphthalen-2-ylmethyl-2,5,8,11-tetraoxo-1-oxa-4,7,10-triaza-cyclopentacos-6-yl]-propyl}-guanidine;

9-Benzyl-6-(3-guanidino-propyl)-12-(4-hydroxy-benzyl)-5,8,11-trioxo-1-oxa-4,7,10-triaza-cyclohexadecane-3-carboxylic acid naphthalen-1-ylamide;

10-Benzyl-7-(3-guanidino-propyl)-13-(4-hydroxy-benzyl)-6,9,12-trioxo-1-oxa-5,8,11-triaza-cycloheptadecane-4-carboxylic acid naphthalen-1-ylamide;

2-Benzyl-5-(3-guanidino-propyl)-13-(4-hydroxy-benzyl)-3,6,14-trioxo-1,4,7-triaza-cyclotetradecane-8-carboxylic acid naphthalen-1-ylamide;

2-Benzyl-5-(3-guanidino-propyl)-12-(4-hydroxy-benzyl)-3,6,13-trioxo-1,4,7-triaza-cyclotridecane-8-carboxylic acid naphthalen-1-ylamide;

12-Benzoylamino-9-benzyl-6-(3-guanidino-propyl)-5,8,11-trioxo-1-oxa-4,7,10-triaza-cyclopentadecane-3-carboxylic acid naphthalen-1-ylamide;

3-Benzoylamino-6-benzyl-9-(3-guanidino-propyl)-4,7,10-trioxo-1-oxa-5,8,11-triaza-cyclopentadecane-12-carboxylic acid naphthalen-1-ylamide;

12-Benzoylamino-9-benzyl-6-(3-guanidino-propyl)-5,8,11-trioxo-114-dioxa4,7,10-triaza-cyclooctadecane-3-carboxylic acid naphthalen-1-ylamide;

12-Benzoylamino-9-benzyl-6-(3-guanidino-propyl)-5,8,11-trioxo-1,15-dioxa-4,7,10-triaza-cyclononadecane-3-carboxylic acid naphthalen-1-ylamide;

13-Benzoylamino-10-benzyl-7-(3-guanidino-propyl)-6,9.12-trioxo-1,16-dioxa-5,8,11-triaza-cycloeicosane-4-carboxylic acid naphthalen-1-ylamide;

13-Benzoylamino-2-benzyl-5-(3-guanidino-propy)-3,6,14-trioxo-1,4,7-triaza-cyclotetradecane-8-carboxylic acid naphthalen-1-ylamide;

13-Benzoylamino-10-benzyl-7-(3-guanidino-propyl)-6,9,12-trioxo-1,15-dioxa-5,8,11-triaza-cyclononadecane-4-carboxylic acid naphthalen-1-ylamide;

12-Benzoylamino-2-benzyl-5-(3-guanidino-propyl)-3,6,13-trioxo-1,4,7-triaza-cyclotridecane-8-carboxylic acid naphthalen-1-ylamide; and 11-Benzoylamino-2-benzyl-5-(3-guanidino-propyl)-3,6,12-trioxo-1,4,7-triaza-cyclododecane-8-carboxylic acid naphthalen-1-ylamide.

12. A cyclic peptide having the formula:
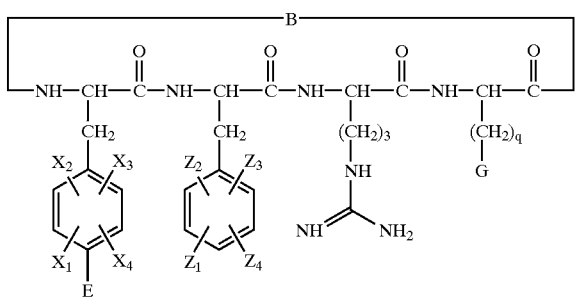
wherein B is a bridge moiety selected from:
i)
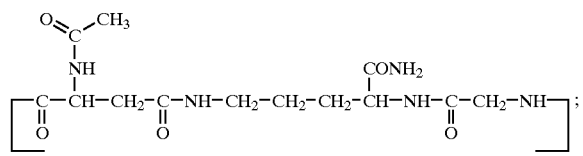
ii)
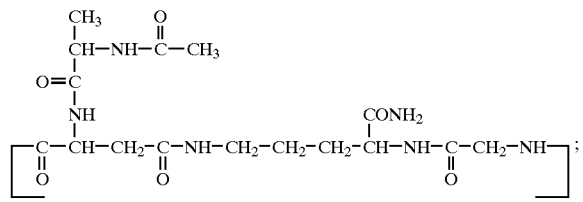
iii)
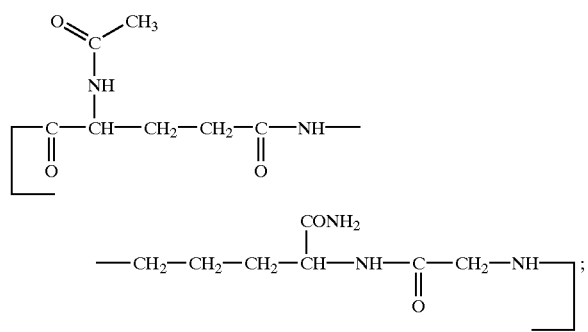
iv)
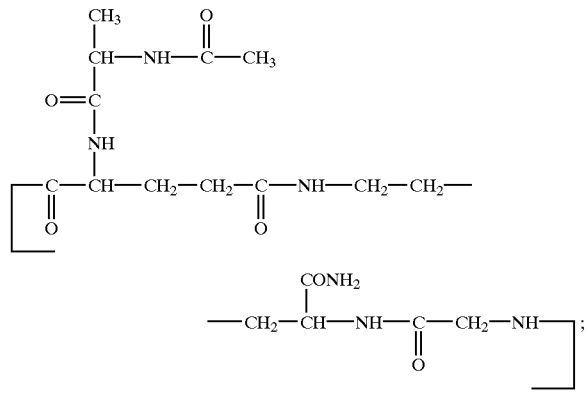
v)
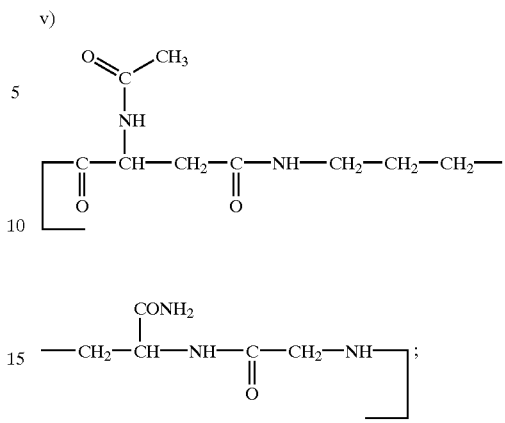
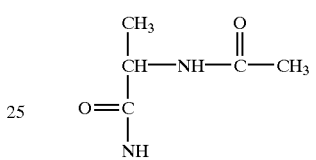
vi)
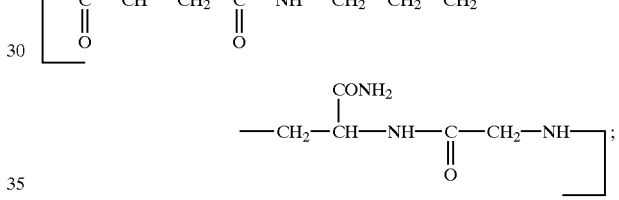
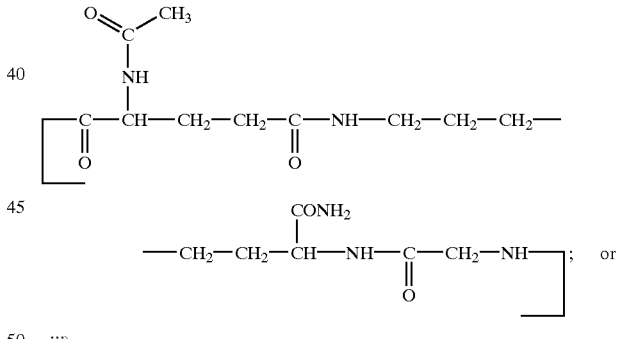
vii)
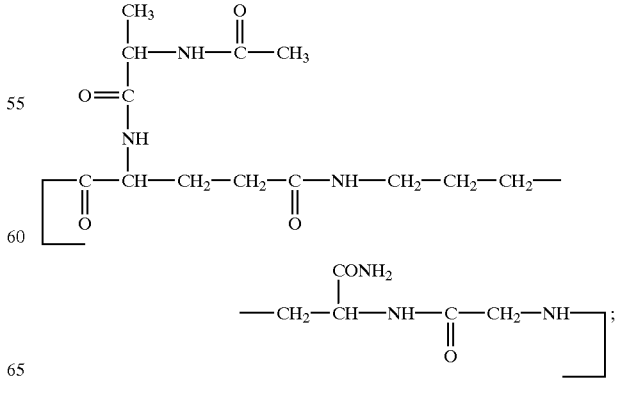 or
viii)

E is hydrogen, halogen, —NO$_2$, —NR$^8$R$^{8'}$ or —OR$^{13}$; R$^8$ and R$^{8'}$ are each independently hydrogen or methyl; R$^{13}$ is hydrogen or methyl;

X$_1$, X$_2$, X$_3$, and X$_4$ represent phenyl ring substituents, said substituents each independently selected from hydrogen, halogen, —NO$_2$, or —OR$^8$; each R$^8$ is hydrogen or methyl;

Z$_1$, Z$_2$, Z$_3$, and Z$_4$ represent phenyl ring substituents, said substituents independently selected from hydrogen, halogen, —OR$^9$; R$^9$ is hydrogen or methyl;

G is selected from a substituted or unsubstituted aryl or heteroaryl ring, the index q is from 1 to 3.

13. A composition comprising:

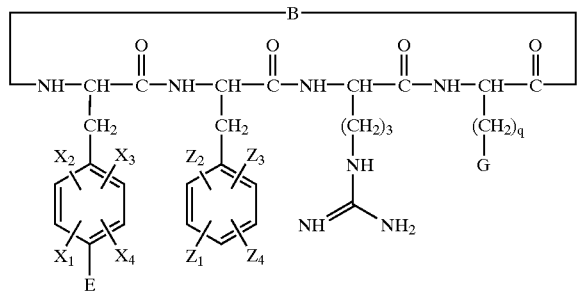

wherein B is a bridge moiety selected from:

i)
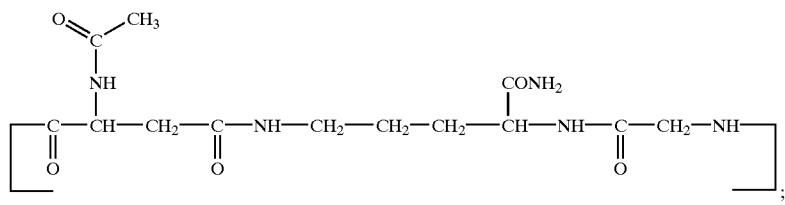

ii)
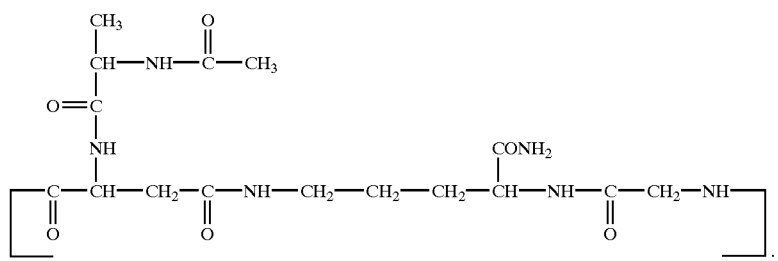

iii)
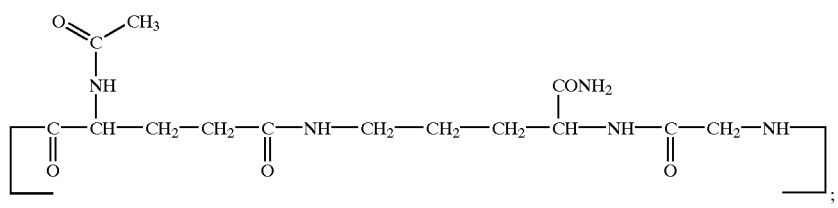

iv)
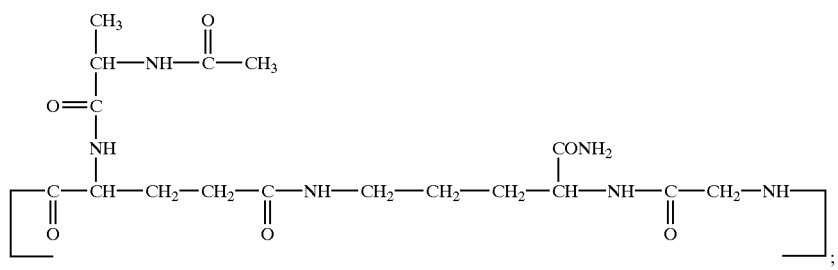

v)
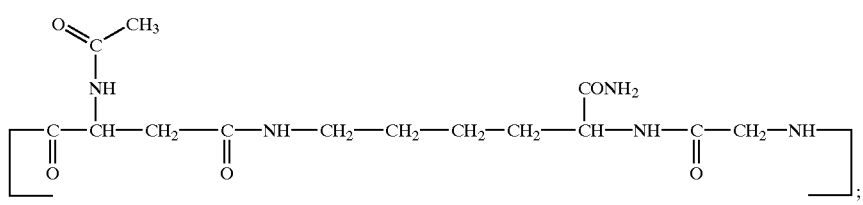
vi)
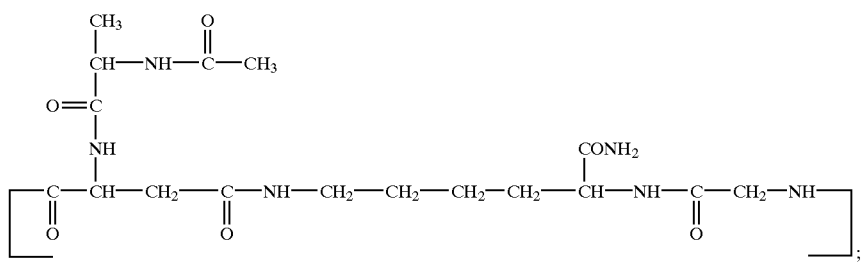
vii)
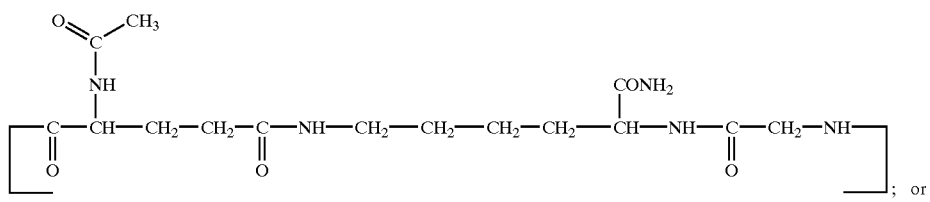
; or
viii)
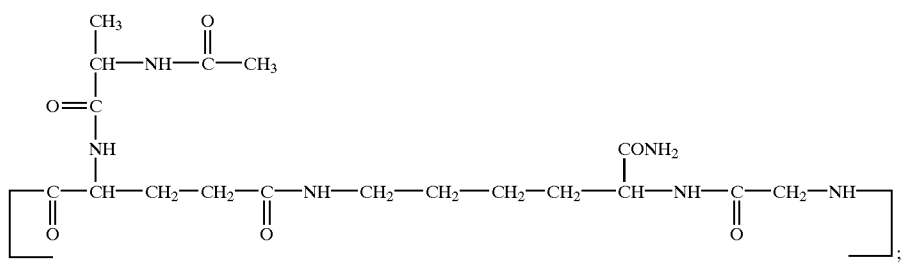
ix)
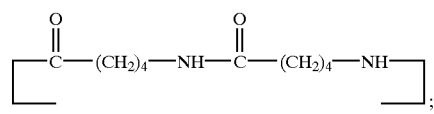
x)
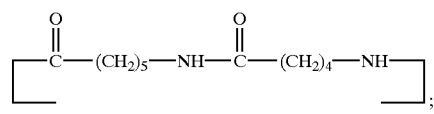
xi)
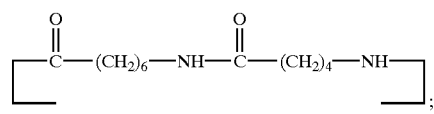
xii)
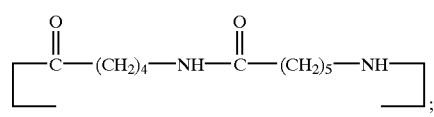

xiii)

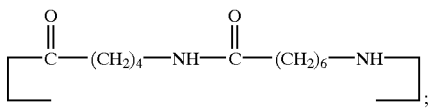

xiv)

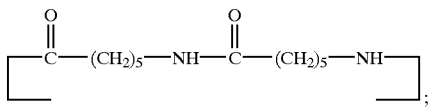

xv)

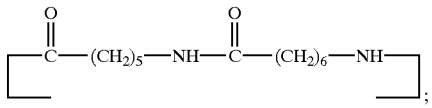

xvi)

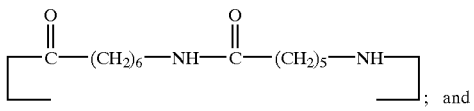

; and xvii)

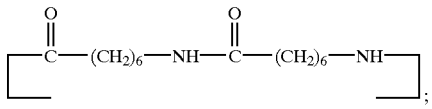

E is selected from the group consisting of hydrogen; halo; —$OR^{13}$; —$SR^{13}$; —$NR^{13}R^{13'}$; —$N(R^{13})SO_2R^{13"}$; —$SO_2R^{13"}$; —$SO_2$—$NR^{13}$ $R^{13'}$; —$(CH_2)_rP(O)(OH)R^{15}$; r is 0 to 10 and $R^{15}$ is selected from the group consisting of —HO, hydrogen; alkyl; alkenyl; alkynyl; cyano; nitro; $CF_3$; aryl; heteroaryl; cycloalkyl; and heterocycloalkyl; provided that when each X is hydrogen, E is not hydrogen; where each $R^{13}$ and $R^{13'}$ is independently selected from the group consisting of hydrogen, alkyl, acyl, heteroalkyl, aryl, heteroaryl, cycloalkyl, and heterocycloalkyl and $R^{13"}$ is selected from the group consisting of hydrogen, alkyl, heteroalkyl, aryl, heteroaryl, cycloalkyl, and heterocycloalkyl; $X_1$, $X_2$, $X_3$, and $X_4$ which represents the four substituents on the phenyl ring other than E is independently selected from hydrogen; halo: $OR^8$; —$SR^8$; —$NR^8R^{8'}$; —$N(R^8)SO_2R^{8"}$; —$SO_2R^{8"}$; —$SO_2$—$NR^8R^{8'}$; —$(CH_2)_rP(O)(OH)R^{14}$; r is 0 to 10; $R^{14}$ is selected from the group consisting of —OH, hydrogen and alkyl; alkyl; alkene: alkyne; cyano; nitro; $CF_3$; aryl; heteroaryl; cycloalkyl; and heterocycloalkyl; each $R^8$ and $R^{8'}$ is independently selected from the group consisting of hydrogen, alkyl, acyl, heteroalkyl, aryl, heteroaryl, cycloalkyl, and heterocycloalkyl; $R^{8"}$ is selected from the group consisting of hydrogen, alkyl, heteroalkyl, aryl, heteroaryl, cycloalkyl, and heterocycloalkyl;

each of $Z_1$, $Z_2$, $Z_3$, and $Z_4$ is one or more substituents independently selected from the group consisting of hydrogen, hydroxy, halo, thiol, —$OR^9$, —$SR^9$, —$NR^9R^{9'}$, alkyl, acyl, alkenyl, alkynyl, cyano, nitro, aryl, heteroaryl, cycloalkyl, and heterocycloalkyl; each $R^9$ and $R^{9'}$ is independently selected from the group consisting of hydrogen, alkyl, acyl, heteroalkyl, aryl, heteroaryl, cycloalkyl, and heterocycloalkyl;

G is selected from a substituted or unsubstituted aryl or heteroaryl ring, the index q is from 1 to 3;

in and amount sufficient to stimulate one or more melanocortin receptors; and (b) the balance one or more excipients.

14. A cyclic peptide having the formula:

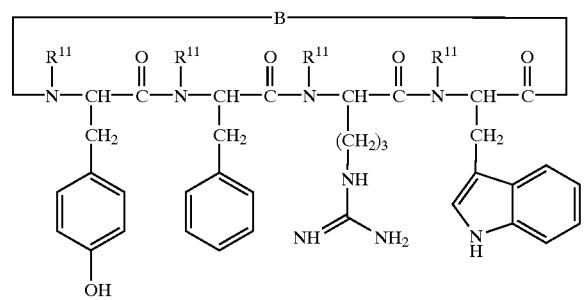

wherein $R^{11}$ is hydrogen and B is a bridge moiety selected from:

i)

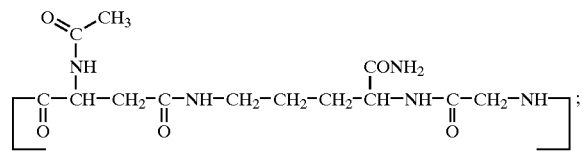

ii) 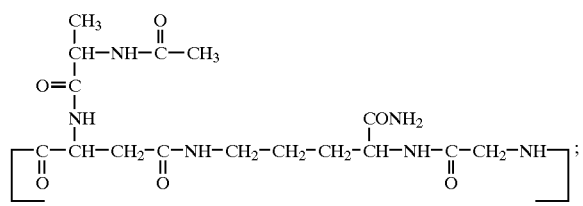
iii) 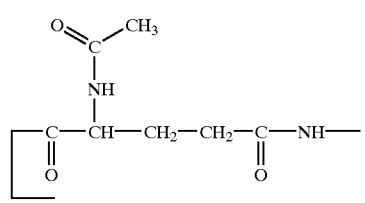
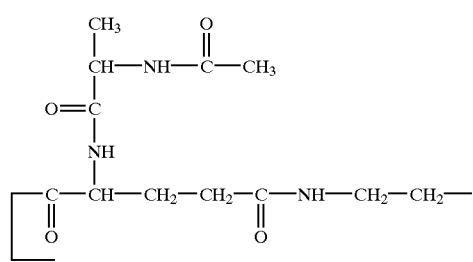
iv) 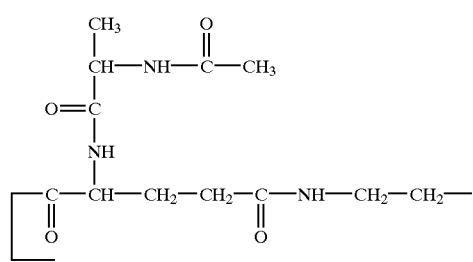
v) 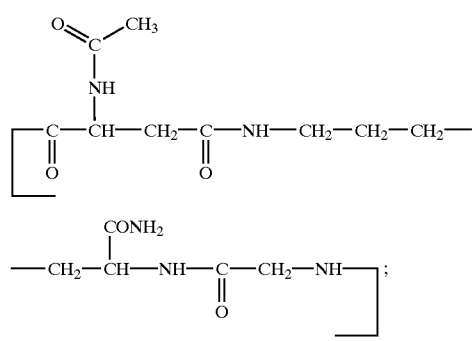
vi) 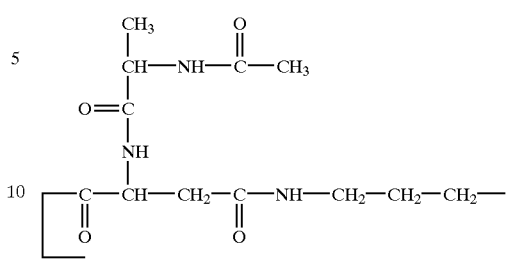
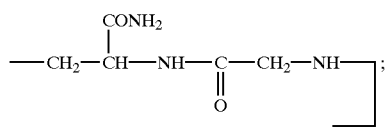
vii) 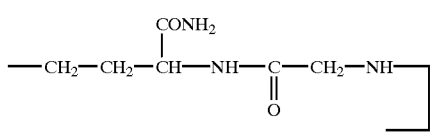
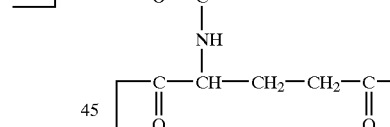; or
viii) 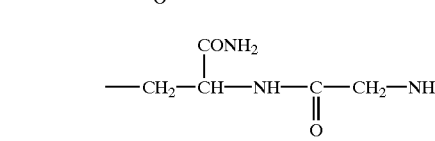
.
* * * * *

UNITED STATES PATENT AND TRADEMARK OFFICE
CERTIFICATE OF CORRECTION

PATENT NO. : 6,613,874 B1
DATED : September 2, 2003
INVENTOR(S) : Adam Wieslaw Mazur et al.

It is certified that error appears in the above-identified patent and that said Letters Patent is hereby corrected as shown below:

Column 3,
Line 41, delete "$R^5$" and insert -- $R^{15}$ --.
Line 62, delete "$r^3$" and insert -- $R^3$ --.
Line 63, delete "bondded, joint " and insert -- bonded, join --.
Line 66, delete "joint" and insert -- join --.

Column 4,
Line 1, delete "joint" and insert -- join --.
Line 65, delete "1x10-8" and insert -- $1 \times 10^{-8}$ --.

Column 5,
Line 22, delete "Ac-a[DYtRWG(Orn)]-$NH_2$" and insert -- Ac-a[DYfRWG(Orn)]-$NH_2$ --.
Line 35, delete "Ac-DYtRWGK-$NH_2$" and insert -- Ac-[DYfRWGK]-$NH_2$ --.
Line 58, delete "leucinc" and insert -- leucine --.

Column 6,
Line 62, start new paragraph with ""Alkylthio" is a buffer..."

Column 7,
Line 43, delete "thereof"; and insert -- thereof. --.

Column 10,
Line 18, delete "$\geqq$" and insert -- $\geq$ --.
Line 60, delete "Flonig" and insert -- Honig --.

Column 33,
Line 60, delete "DeDrotection" and insert -- Deprotection --.
Line 67, delete "pentamethyidihydrobenzofuran" and insert
-- pentamethyldihydrobenzofuran --.

Column 38,
Line 56, delete "iluents" and insert -- diluents --.
Line 57, delete "onsiderations" and insert -- considerations --.
Line 66, delete "ixirs" and insert -- elixirs --.
Line 67, delete "lyethylene" and insert -- polyethylene --.

Column 40,
Line 39, delete "$13^95$-$1^{406}$" and insert -- 1395-1406 --.

UNITED STATES PATENT AND TRADEMARK OFFICE
CERTIFICATE OF CORRECTION

PATENT NO. : 6,613,874 B1
DATED : September 2, 2003
INVENTOR(S) : Adam Wieslaw Mazur et al.

It is certified that error appears in the above-identified patent and that said Letters Patent is hereby corrected as shown below:

Column 44,
Line 45, delete "Fmoc-ys-Boc" and insert -- Fmoc-Lys-Boc --.

Column 47,
Line 2, delete "EOBt" and insert -- HOBt --.

Column 57,
Lines 1-18, delete

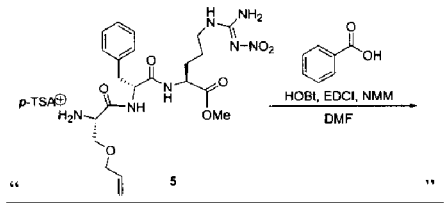

and insert

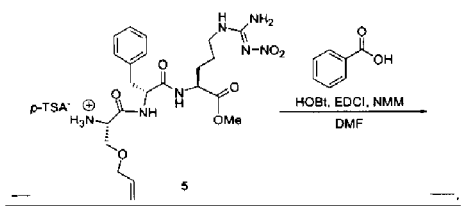

Column 61,
Line 6, delete "]-naphthylalmine" and insert -- 1-naphthylalmine --.

Column 69,
Lines 55-66, delete

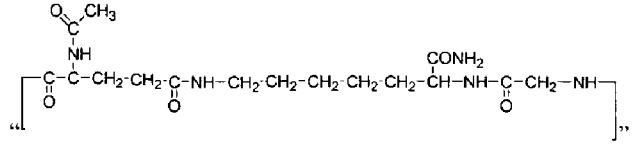

and insert

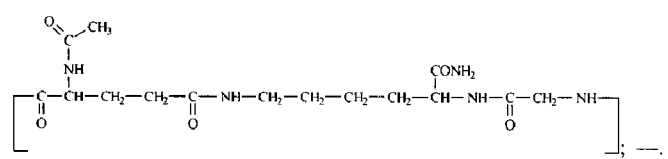

Column 70,
Line 38, delete "$X^2$" and insert -- $X_2$ --.
Line 56, delete "-O-$R^9$ " and insert -- -O$R^9$ --.

UNITED STATES PATENT AND TRADEMARK OFFICE
CERTIFICATE OF CORRECTION

PATENT NO. : 6,613,874 B1
DATED : September 2, 2003
INVENTOR(S) : Adam Wieslaw Mazur et al.

It is certified that error appears in the above-identified patent and that said Letters Patent is hereby corrected as shown below:

Column 75,
Line 54, delete "heteroalkyh" and insert -- heteroalkyl --.
Line 57, delete "heteroalkylh" and insert -- heteroalkyl --.

Column 76,
Line 47, delete "11-trioxo-114-dioxa4,7,10-triaza-cyclooctadecane-3- " and insert -- 11-trioxo-1,14-dioxa4,7,10-triaza-cyclooctadecane-3- --.
Line 53, delete "9.12-trioxo-1,16-dioxa-5,8,11-triaza-cycloeicosane-4-" and insert -- 9,12-trioxo-1,16-dioxa-5,8,11-triaza-cycloeicosane-4- --.

Column 78,
Lines 37-48, delete 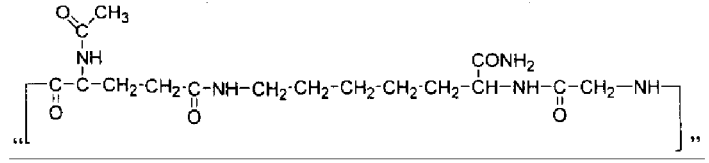

and insert 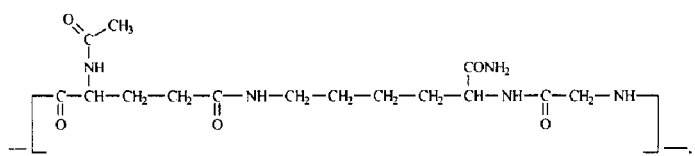

Column 80,
Line 2, please insert missing text -- (a) acyclic peptide analog having the formula: --.

UNITED STATES PATENT AND TRADEMARK OFFICE
CERTIFICATE OF CORRECTION

PATENT NO. : 6,613,874 B1
DATED : September 2, 2003
INVENTOR(S) : Adam Wieslaw Mazur et al.

It is certified that error appears in the above-identified patent and that said Letters Patent is hereby corrected as shown below:

Column 86,
Lines 23-34, delete and insert

Signed and Sealed this

Eleventh Day of January, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 4
<212> TYPE: PRT
<213> ORGANISM: synthetic construct

<400> SEQUENCE: 1

His Phe Arg Trp
1

<210> SEQ ID NO 2
<211> LENGTH: 4
<212> TYPE: PRT
<213> ORGANISM: synthetic construct

<400> SEQUENCE: 2

Tyr Phe Arg Trp
1